(12) United States Patent
Lin et al.

(10) Patent No.: US 11,462,305 B2
(45) Date of Patent: Oct. 4, 2022

(54) BIOMARKERS FOR DETECTING COLORECTAL CANCER OR ADENOMA AND METHODS THEREOF

(71) Applicant: PRECOGIFY PHARMACEUTICAL CHINA CO., LTD., Beijing (CN)

(72) Inventors: Kai Lin, Beijing (CN); Xudong Dai, Beijing (CN); Yu Tian, Beijing (CN); Guan Wang, Beijing (CN)

(73) Assignee: PRECOGIFY PHARMACEUTICAL CHINA CO., LTD., Beijing (CN)

( * ) Notice: Subject to any disclaimer, the term of this patent is extended or adjusted under 35 U.S.C. 154(b) by 0 days.

(21) Appl. No.: 17/451,013

(22) Filed: Oct. 15, 2021

(65) Prior Publication Data
US 2022/0108777 A1 Apr. 7, 2022

Related U.S. Application Data

(63) Continuation of application No. PCT/CN2020/140431, filed on Dec. 28, 2020.

(60) Provisional application No. 62/954,483, filed on Dec. 28, 2019.

(51) Int. Cl.
*G16H 10/40* (2018.01)
*G16H 20/40* (2018.01)
*G16H 20/10* (2018.01)

(52) U.S. Cl.
CPC ............. *G16H 10/40* (2018.01); *G16H 20/10* (2018.01); *G16H 20/40* (2018.01)

(58) Field of Classification Search
CPC ......... G16H 10/40; G16H 20/40; G16H 20/10
See application file for complete search history.

(56) References Cited

U.S. PATENT DOCUMENTS

| 7,349,809 B2 | 3/2008 | Goodenowe |
| 2008/0255764 A1 | 10/2008 | Ritchie et al. |
| 2018/0164320 A1 | 6/2018 | Kim et al. |

FOREIGN PATENT DOCUMENTS

| CN | 110376315 A | 10/2019 |
| WO | 2012023254 A1 | 2/2012 |
| WO | 2013040099 A2 | 3/2013 |

OTHER PUBLICATIONS

Chyke A Doubeni et al., Effectiveness of Screening Colonoscopy in Reducing the Risk of Death From Right and Left Colon Cancer: A Large Community-based Study, Gut, 67: 291-298, 2018.
Medical Advisory Secretariat, Fecal Occult Blood Test for Colorectal Cancer Screening: An Evidence-based Analysis, Ontario Health Technology Assessment Series, 9(10): 1-40, 2009.
N. Manoukian Forones et al., CEA and CA 19-9 as Prognostic Indexes in Colorectal Cancer, Hepato Gastroenterology, 1999, 2 pages.
Snover Dc et al., Reducing Mortality from Colorectal Cancer by Screening for Fecal Occult Blood, New England Journal of Medicine, 328(19): 1365-1371, 1993.
Nam Hee Kim et al., Serum CEA and CA 19-9 Levels are Associated with the Presence and Severity of Colorectal Neoplasia, Yonsei Medical Journal, 58(5): 918-924, 2017.
Laurence Zitvogel et al., Cancer and the Gut Microbiota: An Unexpected Link, Science Translational Medicine, 7(271): 1-10, 2015.
Aurélie Gagnaire et al., Collateral Damage: Insights into Bacterial Mechanisms that Predispose Host Cells to Cancer, Nature Reviews Microbiology, 15: 109-128, 2017.
Alina Janney et al., Host-microbiota Maladaptation in Colorectal Cancer, Nature, 585: 509-517, 2020.
Wendy S. Garrett, The Gut Microbiota and Colon Cancer, Science, 364(6446): 1133-1135, 2019.
Shinichi Yachida et al., Metagenomic and Metabolomic Analyses Reveal Distinct Stage-specific Phenotypes of the Gut Microbiota in Colorectal Cancer, Nature Medicine, 25: 968-976, 2019.
Christine M. Dejea et al., Patients with Familial Adenomatous Polyposis Harbor Colonic Biofilms Containing Tumorigenic Bacteria, Science, 2018, 14 pages.
Thergiory Irrazábal et al., The Multifaceted Role of the Intestinal Microbiota in Colon Cancer, Molecular Cell, 54: 309-320, 2014.
Ting Fu et al., FXR Regulates Intestinal Cancer Stem Cell Proliferation, Cell, 2019, 34 pages.
Matthew R. Wilson et al., The Human Gut Bacterial Genotoxin Colibactin Alkylates DNA, Science, 363(7785): 709-716, 2019.
Cayetano Pleguezuelos-Manzano et al., Mutational Signature in Colorectal Cancer Caused By Genotoxic Pks + E. Coli, Nature, 2020, 19 pages.
Aleksandar D. Kostic et al., Fusobacterium Nucleatum Potentiates Intestinal Tumorigenesis and Modulates the Tumor-immune Microenvironment, Cell Host & Microbe, 14: 207-215, 2013.
Wael Al-Zhoughbi et al., Tumor Macroenvironment and Metabolism, Seminars in Oncology, 41(2): 281-293, 2014.
Matthew G. Vander Heiden et al., Understanding the Intersections Between Metabolism and Cancer Biology, Cell, 2017, 28 pages.
Seema Patel et al., Emerging Field Of Metabolomics: Big Promise for Cancer Biomarker Identification and Drug Discovery, Journal of Pharmaceutical & Biomedical Analysis, 107: 63-74, 2015.
Valentina Tremaroli et al., Functional Interactions Between the Gut Microbiota and Host Metabolism, Nature, 489: 242-249, 2012.

(Continued)

*Primary Examiner* — Jerry Lin
(74) *Attorney, Agent, or Firm* — Metis IP LLC

(57) ABSTRACT

The present disclosure provides a group of diagnostic biomarkers usable for diagnosis of colorectal cancer or colorectal adenoma. A method for detecting colorectal cancer or colorectal adenoma using the group of diagnostic biomarkers is also provided. For example, the method provided by the present disclosure is a non-invasive approach that may utilize serum samples for detecting colorectal cancer. Moreover, the method for detecting colorectal cancer may detect colorectal cancer of different stages (e.g., pre-cancer stage, early stage, middle stage, late stage).

20 Claims, 28 Drawing Sheets

(56) References Cited

OTHER PUBLICATIONS

Gil Sharon et al., Specialized Metabolites From the Microbiome in Health and Disease, Cell Metabolism, 2014, 23 pages.
Dylan Dodd et al., A Gut Bacterial Pathway Metabolizes Aromatic Amino Acids into Nine Circulating Metabolites, Nature, 2017, 21 pages.
Alessia Visconti et al., Interplay Between the Human Gut Microbiome and Host Metabolism, Nature Communications, 2019, 16 pages.
Tiffany L. Weir et al., Stool Microbiome and Metabolome Differences Between Colorectal Cancer Patients and Healthy Adults, Plos One, 8(8): e70803-1-e70803-10, 2013.
Shin Nishiumi et al., A Novel Serum Metabolomics-based Diagnostic Approach for Colorectal Cancer, Plos One, 7(7): e40459-1-e40459-10, 2012.
Aihua Zhang et al., Metabolomics in Diagnosis and Biomarker Discovery of Colorectal Cancer, Cancer Letters, 345:17-20, 2014.
Farshad Farshidfar et al., Serum Metabolomic Profile as a Means to Distinguish Stage of Colorectal Cancer, Genome Medicine, 4(42): 1-13, 2012.
Yunping Qiu et al., Serum Metabolite Profiling of Human Colorectal Cancer Using GC-TOFMS and UPLC-QTOFMS, Journal of Proteome Research, 8: 4844-4850, 2009.
James J. Goedert et al., Fecal Metabolomics: Assay Performance and Association with Colorectal Cancer, Carcinogenesis, 35(5): 2089-2096, 2014.
Liang Liang et al., Metabolic Dynamics and Prediction of Gestational Age and Time to Delivery in Pregnant Women, Cell, 181: 1680-1692, 2020.
Junjie Qin et al., A Human Gut Microbial Gene Catalogue Established by Metagenomic Sequencing, Nature, 464:59-65, 2010.
Fujian Zheng et al., Development of a Plasma Pseudotargeted Metabolomics Method Based on Ultra-high-performance Liquid Chromatography-mass Spectrometry, Nature Protocols, 15: 2519-2537, 2020.
Chenglong Sun et al., Spatially Resolved Metabolomics to Discover Tumor-associated Metabolic Alterations, Proceedings of the National Academy of Sciences, 116(1): 52-57, 2019.
Tomasz Wilmanski et al., Blood Metabolome Predicts Gut Microbiome α-diversity in Humans, Nature Biotechnology, 37: 1217-1228, 2019.
Charlotte A. Huber et al., Bacterial Identification Using an Absciex 5800 TOF/TOF MALDI Research Instrument and an External Database, Journal of Microbiological Methods, 2019, 3 pages.
Long H. Nguyen et al., Association Between Sulfur-metabolizing Bacterial Communities in Stool and Risk of Distal Colorectal Cancer in Men, Gastroenterology, 158(5): 1313-1325, 2020.
Cemal Yazici et al., Race-dependent Association of Sulfidogenic Bacteria with Colorectal Cancer, Gut, 66: 1983-1994, 2017.
Garyee Koh et al., Parabacteroides Distasonis Attenuates Toll-like Receptor 4 Signaling and Akt Activation and Blocks Colon Tumor Formation in High-fat diet-fed Azoxymethane-treated Mice, International Journal of Cancer, 143: 1797-1805, 2018.
Almut Heinken et al., Systematic Assessment of Secondary Bile Acid Metabolism in Gut Microbes Reveals Distinct Metabolic Capabilities in Inflammatory Bowel Disease, Microbiome, 7(75): 1-18, 2019.
Suzanne Devkota et al., Dietary-fat-induced Taurocholic Acid Promotes Pathobiont Expansion and Colitis in IL10-/- Mice, Nature, 2012, 14 pages.
Norbert Wild et al., A Combination of Serum Markers for the Early Detection of Colorectal Cancer, Clinical Cancer Research, 16: 6111-6121, 2010.
Tobias Niedermaier et al., Stage-specific Sensitivity of Fecal Immunochemical Tests for Detecting Colorectal Cancer: Systematic Review and Meta-analysis, The American journal of gastroenterology, 115: 56-69, 2020.
Julia Mayerle et al., Metabolic Biomarker Signature to Differentiate Pancreatic Ductal Adenocarcinoma From Chronic Pancreatitis, Gut, 67: 128-137, 2018.
Baowen Yuan et al., A Plasma Metabolite Panel as Biomarkers for Early Primary Breast Cancer Detection, International Journal of Cancer, 144: 2833-2842, 2019.
Joshua D. Cohen et al., Detection and Localization of Surgically Resectable Cancers with a Multi-analyte Blood Test, Science, 359: 926-930, 2018.
Song Wu et al., Substantial Contribution of Extrinsic Risk Factors to Cancer Development, Nature, 2016, 22 pages.
Andrew C. Goodwin et al., Polyamine Catabolism Contributes To Enterotoxigenic Bacteroides Fragilis-induced Colon Tumorigenesis, Proceedings of the National Academy of Sciences, 108(37): 15354-15359, 2011.
Harris Bernstein et al., Bile Acids as Endogenous Etiologic Agents in Gastrointestinal Cancer, World Journal of Gastroenterology, 15(27): 3329-3340, 2009.
Yuanqi Wu et al., Identification of Microbial Markers Across Populations in Early Detection of Colorectal Cancer, Nature Communications, 2021, 13 pages.
M. Poyet et al., A Library of Human Gut Bacterial Isolates Paired with Longitudinal Multiomics Data Enables Mechanistic Microbiome Research, Nature Medicine, 2019, 27 pages.
Jason Lloyd-Price et al., Multi-omics of the Gut Microbial Ecosystem in Inflammatory Bowel Diseases, Nature, 569: 655-662, 2019.
James T. Morton et al., Learning Representations of Microbe-metabolite Interactions, Nature Methods, 2019, 15 pages.
Anthony M. Bolger et al., Trimmomatic: A Flexible Trimmer for Illumina Sequence Data, Bioinformatics, 30(15): 2114-2120, 2014.
Ben Langmead et al., Fast Gapped-read Alignment with Bowtie 2, Nature Methods, 2012, 8 pages.
Duy Tin Truong et al., MetaPhlAn2 for Enhanced Metagenomic Taxonomic Profiling, Nature Methods, 2015, 2 pages.
Xavier Domingo-Almenara et al., Annotation: A Computational Solution for Streamlining Metabolomics Analysis, Analytical Chemistry, 2018, 21 pages.
International Search Report in PCT/CN2020/140431 dated Mar. 29, 2021, 7 pages.
Written Opinion in PCT/CN2020/140431 dated Mar. 29, 2021, 6 pages.
Yang, Yongzhi et al., Integrated Microbiome and Metabolome Analysis Reveals a Novel Interplay Between Commensal Bacteria and Metabolites in Colorectal Cancer, Theranostics, 9(14): 4101-4114, 2019.
Yang, Jun et al., Postprandial Effect to Decrease Soluble Epoxide Hydrolase Activity: Roles of Insulin and Gut Microbiota, The Journal of Nutritional Biochemistry, 49: 8-14, 2017.
Hong, Yongfu et al., A New Cerebroside from Lens Culinaris Medic, Journal of Chinese Pharmaceutical Sciences, 8(1): 8-10, 1999.

BIOMARKERS FOR DETECTING COLORECTAL CANCER OR ADENOMA AND METHODS THEREOF

CROSS-REFERENCE TO RELATED APPLICATIONS

This application is a continuation of International Application No. PCT/CN2020/140431, filed on Dec. 28, 2020, which claims priority of U.S. provisional patent application No. 62/954,483, filed on Dec. 28, 2019, the entire contents of each of which are incorporated herein by reference.

TECHNICAL FIELD

The present disclosure generally relates to detection of colorectal abnormality, and in particular, to biomarkers for detecting colorectal cancer or adenoma and methods thereof.

BACKGROUND

Colorectal cancer (CRC) usually refers to a cancer developed from the colon or rectum (parts of the large intestine). CRC has become a growing clinical challenge worldwide, while early diagnosis is recognized as an effective way to improve the survival rate for CRC patients. Adenoma usually refers to a benign tumor of epithelial tissue. Adenoma of the colon, also referred to as "colorectal adenoma (CRA)" or "adenomatous polyp", tends to become malignant and leads to CRC. Thus, the diagnosis of CRA or CRC is important in evaluating the colorectal health of a patient.

Several approaches have been adopted clinically for the diagnosis of CRC and/or CRA, including non-invasive approaches and invasive approaches. For example, the non-invasive approaches include a fecal occult blood test (FOBT), using tumor biomarkers such as carcinoembryonic antigen (CEA)), etc. As another example, the invasive approaches include using a colonoscope to determine whether there are visible tumor lesions or adenomatous polyps, a biopsy test, etc. While the invasive approaches remain the gold standard for CRC/CRA diagnosis, they often cause discomfort, pain, or even tissue damage to the patient. As a result, the non-invasive approaches are sometimes preferred. However, many conventional non-invasive approaches suffer from low accuracy. Therefore, it is desirable to find new biomarkers that can bring about non-invasive methods for the detection of CRC or CRA with improved accuracy.

SUMMARY

According to an aspect of the present disclosure, a group of diagnostic biomarkers usable for diagnosis of colorectal cancer (CRC) or adenoma are provided. In some embodiments, the group of diagnostic biomarkers may include one or more metabolites listed in Table A.

TABLE A

| MASS(+/−) | Compound | Delta(ppm) |
|---|---|---|
| 329.233(−) | C18H34O5 | 1 |
| 329.233(−) | 9,12,18-TriHOME (12Z) | 1 |
| 420.807(+) | C42H80NO8P | 19 |
| 637.157(−) | C32H31O14 | 0 |
| 398.18(−) | C15H27NO4 | 1 |
| 353.212(−) | C23H29O3 | 0 |
| 368.169(−) | C19H23N5O3 | 10 |
| 355.228(−) | C46H64O6 | 0 |

In some embodiments, the plurality of metabolites may further include the metabolites of Table B. In some embodiments, the abundance of all eight metabolites in Table A and the abundance of at least one metabolite in Table B are quantified.

TABLE B

| MASS(+/−) | Compound | Delta(ppm) |
|---|---|---|
| 193.09(−) | C6H14OS | 2 |
| 380.033(−) | C15H15N3O5S2 | 13 |
| 289.164(+) | C15H22O5 | 4 |
| 750.519(+) | C39H76NO10P | 12 |
| 357.228(−) | C15H30N6O4 | 7 |
| 637.105(+) | C23H22F7N4O6P | 1 |
| 612.425(+) | C37H54O6 | 1 |
| 512.336(−) | C27H45NO | 1 |
| 543.376(+) | C35H52O3 | 9 |
| 490.686(+) | C80H152O17P2 | 3 |
| 483.297(−) | C26H44O8 | 1 |
| 319.264(−) | C21H36O2 | 1 |
| 447.312(−) | C27H44O5 | 1 |
| 279.233(−) | C18H32O2 | 0 |
| 578.25(+) | C28H37N5O7 | 15 |
| 572.415(+) | C29H60NO7P | 21 |
| 461.196(+) | C26H30O6 | 6 |
| 475.116(−) | C19H24O14 | 14 |
| 513.363(+) | C32H48O5 | 11 |
| 502.015(+) | C16H22BrN3O7S | 21 |
| 384.259(+) | C22H35NO3 | 21 |
| 197.068(−) | C7H10N4O3 | 0 |
| 584.729(+) | C43H74N7O17P3S | 15 |

In some embodiments, the plurality of metabolites may further include the metabolites of Table C. In some embodiments, the abundance of all eight metabolites in Table A and the abundance of all metabolites in Table C may be quantified.

TABLE C

| MASS(+/−) | Compound | Delta(ppm) |
|---|---|---|
| 193.09(−) | C11H14O3 | 15 |
| 223.134(−) | C13H20O3 | 0 |
| 289.106(−) | C16H18O5 | 7 |
| 355.227(+) | C21H32O3 | 7 |
| 382.183(+) | C20H25NO6 | 3 |
| 386.067(−) | C14H15NO9 | 15 |
| 398.179(−) | C22H29N3S2 | 15 |
| 447.311(−) | C27H44O5 | 1 |
| 461.195(+) | C28H28O6 | 2 |
| 462.141(−) | C19H20FN5O5 | 4 |
| 471.005(+) | C16H16O11S2 | 5 |
| 476.011(+) | C10H16N5O11P3 | 5 |
| 476.358(+) | C30H42O2 | 12 |
| 477.13(+) | C28H22O6 | 2 |
| 483.368(+) | C30H52O2 | 17 |
| 494.68(+) | C83H150O17P2 | 11 |
| 495.024(+) | C21H12O14 | 30 |
| 504.692(+) | C12H6Br4O | 25 |
| 509.03(+) | C10H16N5O12P3 | 9 |
| 514.027(+) | C10H17N7O12S2 | 0 |
| 514.705(+) | C44H61N13O12S2 | 5 |
| 519.043(+) | C20H16O15 | 9 |
| 531.178(−) | C27H32O11 | 17 |
| 534.052(+) | C16H17N9O5S3 | 21 |
| 536.299(−) | C23H44NO7P | 1 |

TABLE C-continued

| MASS(+/−) | Compound | Delta(ppm) |
|---|---|---|
| 539.384(+) | C32H52O5 | 25 |
| 542.426(+) | C54H106NO10P | 2 |
| 543.378(+) | C35H52O3 | 5 |
| 549.062(+) | C22H22O14 | 4 |
| 563.068(+) | C30H20O9 | 10 |
| 567.155(−) | C28H28N2O11 | 12 |
| 568.075(+) | C21H18O14S | 1 |
| 587.088(+) | C25H24O13S | 9 |
| 597.091(+) | C26H22O15 | 10 |
| 616.463(+) | C37H58O6 | 9 |
| 629.391(+) | C40H56O7 | 11 |
| 631.103(−) | C28H24O17 | 14 |
| 646.473(+) | C35H68NO7P | 12 |
| 702.536(+) | C39H76NO7P | 10 |
| 732.546(+) | C41H76NO7P | 8 |
| 776.038(+) | C27H20O21S | 1 |
| 804.604(+) | C45H84NO8P | 7 |
| 877.609(+) | C44H85NO11S | 10 |
| 938.662(+) | C54H94NO8P | 1 |
| 950.698(+) | C54H97NO10P | 14 |
| 994.724(+) | C54H101NO13 | 8 |
| 1038.751(+) | C65H98O6 | 1 |
| 1040.729(+) | C56H107NO13 | 8 |
| 432.109(−) | C21H21O10 | 6 |
| 635.934(+) | C64H120N2O21 | 9 |
| 714.829(+) | C65H102O33 | 9 |

According to another aspect of the present disclosure, a method of detecting CRC/CRA in a subject is provided. In some embodiments, the method may include step a): quantifying the abundance of one or more components of a panel of a plurality of metabolites in a sample from the subject. The plurality of metabolites may include the metabolites listed in Table A, Table B, and/or Table C, as described earlier in the present disclosure. In some embodiments, the method may further include determining a sample score by processing the abundance of each of the metabolites quantified in step a). In some embodiments, the method may further include step c): detecting CRC/CRA in the subject by comparing the sample score to a cut-off score.

In some embodiments, the prediction model may be established by a logistic regression method.

In some embodiments, the prediction model may be established by a logistic regression method based on measurement of the abundance of the metabolites from samples with known normal, CRC, or CRA status.

In some embodiments, step (c) may further include detecting CRC/CRA in the subject if the sample score is equal to or greater than the cut-off score.

In some embodiments, for a receiver operating characteristic (ROC) curve, the method may have an area-under-the-curve (AUC) of more than 0.80, and both sensitivity and specificity of detecting CRC/CRA in the sample may be equal to or greater than 75%.

In some embodiments, for a ROC curve, the method may have an AUC of more than 0.85, and both sensitivity and specificity of detecting CRC/CRA in the sample are equal to or greater than 80%.

According to another aspect of the present disclosure, a method of detecting CRC/CRA in a subject is provided. In some embodiments, the method may include step a): quantifying the abundance of one or more components of a panel of a plurality of metabolites in a sample from the subject. The plurality of metabolites may include the metabolites listed in Table A, Table B, and/or Table C, as described earlier in the present disclosure. In some embodiments, the method may further include determining a sample score by processing the abundance of each of the metabolites quantified in step a). In some embodiments, the method may further include step c): detecting CRC/CRA in the subject by comparing the sample score to a cut-off score.

According to another aspect of the present disclosure, a method of detecting CRA in a subject is provided. The method may include step a): quantifying abundance of at least five components of a panel of a plurality of metabolites in a sample from the subject. The method may further include step b): determining a sample score by processing the abundance of each of the metabolites quantified in step a). The method may still further include step c): detecting CRA in the subject by comparing the evaluation value to a cut-off value. In some embodiments, the plurality of metabolites may include the metabolites listed in Table A, Table B, and/or Table C, as described earlier in the present disclosure.

According to yet another aspect of the present disclosure, a method of detecting stage I/II CRC in a subject is provided. The method may include (a) quantifying abundance of one or more components of a panel of a plurality of metabolites in a sample from the subject with mass spectrometry, wherein the plurality of metabolites include the metabolites of Table A; (b) determining a sample score by processing the concentration of each of the metabolites quantified in step (a); and (c) detecting stage I/II CRC in the subject by comparing the evaluation value to a cut-off value. In some embodiments, the plurality of metabolites may include the metabolites listed in Table A, Table B, and/or Table C, as described earlier in the present disclosure.

According to yet another aspect of the present disclosure, a method of detecting stage III/IV CRC in a subject is provided. The method may include (a) quantifying abundance of one or more components of a panel of a plurality of metabolites in a sample from the subject with mass spectrometry, wherein the plurality of metabolites include the metabolites of Table A; (b) determining a sample score by processing the concentration of each of the metabolites quantified in step (a); and (c) detecting stage III/IV CRC in the subject by comparing the evaluation value to a cut-off value. In some embodiments, the plurality of metabolites may include the metabolites listed in Table A, Table B, and/or Table C, as described earlier in the present disclosure.

According to still another aspect of the present disclosure, a method of treating CRC/CRA in a subject is provided. The method may include detecting CRC/CRA according to the methods described earlier in the present disclosure, and applying treatment to the subject for CRC/CRA.

In some embodiments, the method may further include verifying the CRC/CRA with colonoscopy.

In some embodiments, the treatment may further include colectomy or ostomy.

In some embodiments, the treatment may further include chemotherapy, radiation therapy, targeted drug therapy, or immunotherapy.

In some embodiments, the treatment may include palliative care.

According to still another aspect of the present disclosure, a method of identifying gut microbiome-associated (GMA) metabolites as biomarkers for a prediction panel for CRC/CRA is provided. In some embodiments, the method may include obtaining source data by conducting untargeted mass spectrometry to samples from CRC/CRA patients and control group of persons not having CRC/CRA. The method may further include identifying a first group of metabolites that are significantly altered in the CRC/CRA patients. A second group of metabolites may be identified from the first group by selecting metabolites that show significant correlation with gut microbiome. The method may further include selecting the GMA metabolites for the prediction panel from the second group of metabolites using a selection model.

In some embodiments, the method may further include verifying the second group of metabolites with metagenome sequencing.

In some embodiments, the selection model may utilize a least absolute shrinkage and selection operator (LASSO) algorithm.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. It should be noted that the drawings are not to scale. These embodiments are non-limiting exemplary embodiments, in which like reference numerals represent similar structures throughout the several views of the drawings, and wherein.

DETAILED DESCRIPTION

Figure 1A:
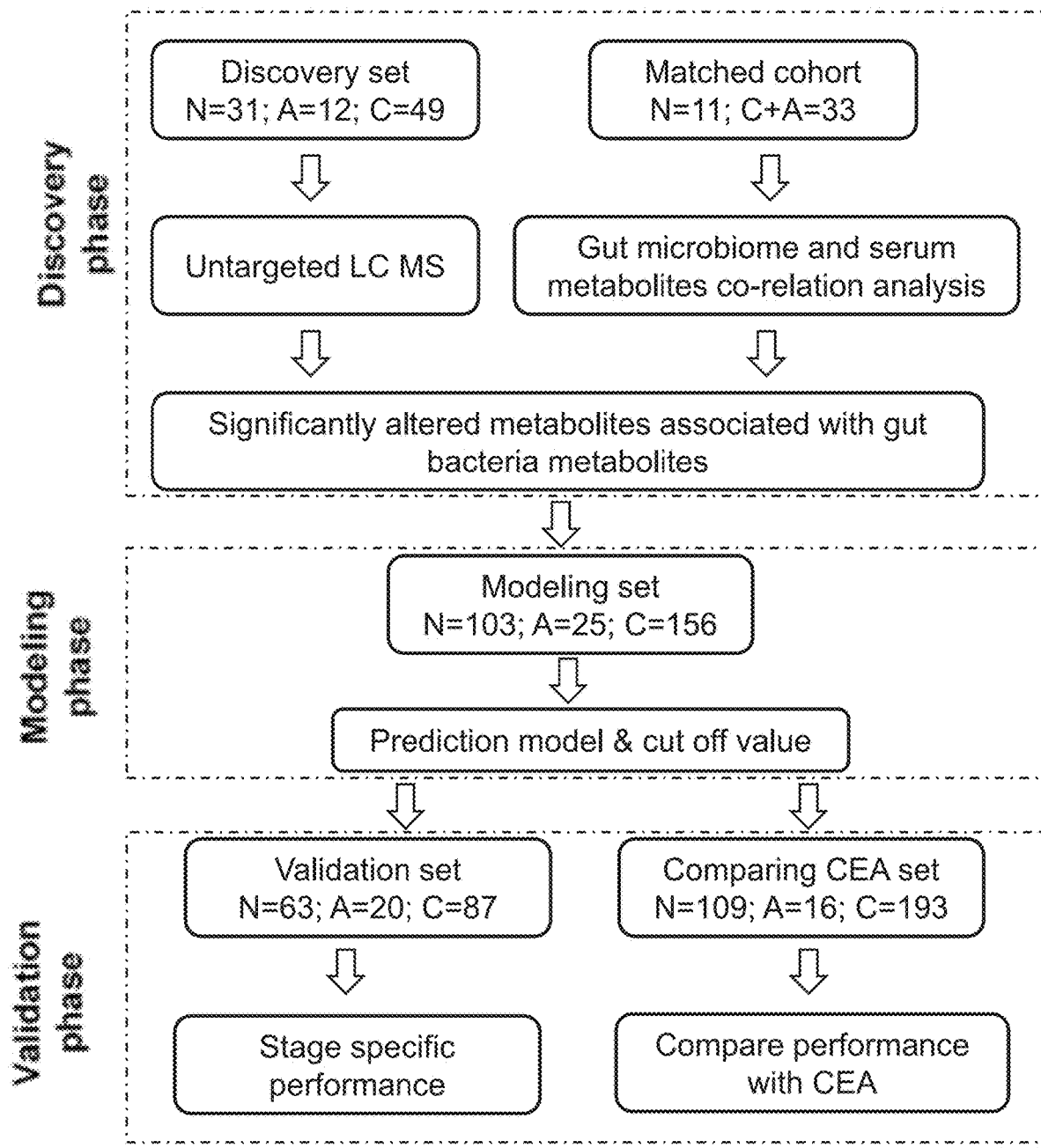
FIG. 1A is a schematic diagram illustrating overview of experimental design and analysis procedures according to some embodiments of the present disclosure.

The following description is presented to enable any person skilled in the art to make and use the present disclosure and is provided in the context of a particular application and its requirements. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown but is to be accorded the widest scope consistent with the claims.

The terminology used herein is to describe particular example embodiments only and is not intended to be limiting. As used herein, the singular forms "a," "an," and "the" may be intended to include the plural forms as well, unless the context clearly indicates otherwise. It will be further understood that the terms "comprises," "comprising," "includes," and/or "including" when used in this specification, specify the presence of stated features, integers, steps, operations, elements, and/or components, but do not preclude the presence or addition of one or more other features, integers, steps, operations, elements, components, and/or groups thereof.

These and other features, and characteristics of the present disclosure, as well as the methods of operation and functions of the related elements of structure and the combination of parts and economies of manufacture, may become more apparent upon consideration of the following description with reference to the accompanying drawing(s), all of which form a part of this specification. It is to be expressly understood, however, that the drawing(s) is for the purpose of illustration and description only and are not intended to limit the scope of the present disclosure. It is understood that the drawings are not to scale.

The present disclosure provides a group of diagnostic biomarkers usable for diagnosis of colorectal cancer or colorectal adenoma. A method for detecting colorectal cancer or colorectal adenoma using the group of diagnostic biomarkers is also provided. For example, the method provided by the present disclosure is a non-invasive approach that utilizes body fluid or other sample (e.g., serum samples, fecal samples) for detecting colorectal cancer. Moreover, the method for detecting colorectal cancer may detect colorectal cancer of different stages (e.g., pre-cancer stage, early stage, middle stage, late stage). The detection of early stage or pre-cancer stage colorectal cancer in a subject effectively improve the survival rate for CRC patients. As compared with conventional methods for detecting colorectal cancer (e.g., a method using CEA biomarker), the methods for detecting colorectal cancer provided by the present disclosure are more accurate, and effectively distinguishing subjects having CRC/CRA from normal subjects.

As used herein, the term "subject" of the present disclosure refers to any human or non-human animal. Exemplary non-human animal may include Mammalia (such as chimpanzees and other apes and monkey species), farm animals (such as cattle, sheep, pigs, goats, and horses), domestic mammals (such as dogs and cats), laboratory animals (such as mice, rats, and guinea pigs), or the like. In some embodiments, the subject is a human.

According to an aspect of the present disclosure, a group of diagnostic biomarkers usable for diagnosis of colorectal cancer (CRC) or adenoma are provided. In some embodiments, the adenoma includes colorectal adenoma (CRA), which is also referred to as adenomatous polyp. The term "CRC/CRA" in the present disclosure refers to either CRC or CRA, being distinct from normal conditions.

In some embodiments, the group of diagnostic biomarkers may include one or more metabolites correlated with CRC/CRA. The one or more metabolites may be produced or affected by gut bacteria and may be conveyed to different portions of the body of a subject for performing various functions such as regulatory functions. As used herein, the phrase "affected by gut bacteria" means that the abundance of a metabolite may be altered (e.g., increased or reduced) under the effect of gut bacteria.

In some embodiments, the abundance of the metabolite(s) in a sample obtained from a normal subject may be different from the abundance of the metabolite(s) in a sample obtained from a subject that has CRC/CRA. As used herein, the term "abundance" refers to the quantity or amount of a substance in a certain sample. The sample may be a solid sample, a fluid sample, a gas sample, or the like, or any combination thereof. The solid sample may include, for example, feces, earwax, etc. The fluid sample may include the body fluid of the subject, such as blood, serum, saliva, urine, sweat, or the like, or any combination thereof. The gas sample may include flatus, breath, etc. Merely by way of example, the one or more metabolites may be present in the serum and may be referred to as "serum metabolites". In some embodiments, to measure the abundance of a metabolite, the concentration or amount of the metabolite in a fluid sample (e.g., serum), a solid sample, or a gas sample (e.g., flatus) may be measured. In some embodiments, the abundance of a metabolite may be a normalized value or a relative value with respect to a control. In this case, the abundance of the metabolite is also referred to as the "relative abundance". For instance, the abundance of a metabolite may reflect a z-score that is based on a measured value of the metabolite and a combined measured value of all the metabolites in a sample. In some embodiments, the measured value may be obtained by mass spectrometry, chromatography (e.g., HPLC), and any other techniques. In some embodiments, the control may be the precise concentration or amount of a set of chemicals that are artificially added into a subject, such as spike-in control. Alternatively, the control may be the concentration or amount of the same metabolite of a sample obtained from a pool of subjects who do not have CRC/CRA and is considered physically healthy.

Table 1 shows an exemplary group of metabolites that can be used for the diagnosis of CRC/CRA. Each of the metabolites, which are biomarkers, has shown strong and faithful correlation with the presence of CRC/CRA. In some embodiments, the group of diagnostic biomarkers provided by the present disclosure may include one or more metabolites of Table 1. In some embodiments, the group of diagnostic biomarkers may include at least one of the metabolites of Table 1. In some embodiments, the group of diagnostic biomarkers may include at least two of the metabolites of Table 1. In some embodiments, the group of diagnostic biomarkers may include at least three of the metabolites of Table 1. In some embodiments, the group of diagnostic biomarkers may include at least four of the metabolites of Table 1. In some embodiments, the group of diagnostic biomarkers may include at least five of the metabolites of Table 1. In some embodiments, the group of diagnostic biomarkers may include at least six of the metabolites of Table 1. In some embodiments, the group of diagnostic biomarkers may include at least seven of the metabolites of Table 1. As another example, the group of diagnostic biomarkers may include all of the metabolites of Table 1.

TABLE 1

| No. | MASS(+/−) | Compound | Delta(ppm) |
|---|---|---|---|
| 1 | 329.233(−) | C18H34O5 | 1 |
| 2 | 329.233(−) | 9,12,18-TriHOME (12Z) | 1 |

TABLE 1-continued

| No. | MASS(+/−) | Compound | Delta(ppm) |
|---|---|---|---|
| 3 | 420.807(+) | C42H80NO8P | 19 |
| 4 | 637.157(−) | C32H31O14 | 0 |
| 5 | 398.18(−) | C15H27NO4 | 1 |
| 6 | 353.212(−) | C23H29O3 | 0 |
| 7 | 368.169(−) | C19H23N5O3 | 10 |
| 8 | 355.228(−) | C46H64O6 | 0 |

In some embodiments, the metabolites shown in Table 1 can be used for detecting CRC/CRA in the subject, and can be further used in facilitating the treatment of CRC/CRA. For example, mass spectrometry (or other techniques) may be used to quantify the abundance of one or more metabolites in a panel of a plurality of metabolites in a sample. The abundance of each metabolite that has been quantified can be processed and used to detect CRC/CRA and/or facilitate the treatment of CRC/CRC in the subject. In some embodiments, any one of the metabolites in Table 1 can be quantified and used for these purposes. In some embodiments, any two, three, or four metabolites in Table 1 can be quantified and used for these purposes. In some embodiments, any five, six, or seven metabolites in Table 1 can be quantified and used for these purposes. In some embodiments, all eight metabolites in Table 1 can be quantified and used for these purposes.

In some embodiments, the metabolites in Table 1 can be quantified and identified by mass spectrometry. A metabolite shown in Table 1 may correspond to one or more isomeride forms. Table 2 shows some exemplary compounds corresponding to the metabolites shown in Table 1, after annotation and inferring. The abundance of one or more of these compounds, or biomarkers, can be quantified, e.g., by mass spectrometry or any other techniques, and used for detecting CRC/CRA in the subject, and/or to facilitate the treatment of CRC/CRA in the subject. In some embodiments, each of the metabolites in Table 1 or Table may be associated with gut microbiome.

TABLE 2

| No. | Metabolite |
|---|---|
| 1 | 9,12,13-TriHOME |
| 2 | 9,12,18-TriHOME |
| 3 | culinariside |
| 4 | [(6-{[5,7-dihydroxy-2-(4-oxocyclohexa-2,5-dien-1-ylidene)-2H-chromen-3-yl]oxy}-3,4,5-trihydroxyoxan-2-yl)methyl][1-hydroxy-3-(4-hydroxyphenyl)prop-2-en-1-ylidene]oxidanium |
| 5 | 2-octenoylcarnitine |
| 6 | (E)-2-(4,8-dimethylnona-3,7-dien-1-yl)-5-hydroxy-2,7-dimethyl-2H-chromene-8-carbaldehyde |
| 7 | N,O-Bis-(trimethylsilyl)phenylalanine |
| 8 | 14-HDoHE |

In some embodiments, the group of diagnostic biomarkers (metabolites) that can be quantified and used for detecting CRC/CRA and/or facilitating the treatment of CRC/CRA may include 9,12,13-TriHOME. In some embodiments, the group of diagnostic biomarkers that can be quantified and used for these purposes that can be quantified and used for these purposes may include 9,12,18-TriHOME. In some embodiments, the group of diagnostic biomarkers that can be quantified and used for these purposes may include culinariside. In some embodiments, the group of diagnostic biomarkers that can be quantified and used for these purposes may include [(6-{[5,7-dihydroxy-2-(4-oxocyclohexa-2,5-dien-1-ylidene)-2H-chromen-3-yl]oxy}-3,4,5-trihydroxyoxan-2-yl)methyl][1-hydroxy-3-(4-hydroxyphenyl)prop-2-en-1-ylidene]oxidanium. In some embodiments, the group of diagnostic biomarkers that can be quantified and used for these purposes may include 2-octenoylcarnitine. In some embodiments, the group of diagnostic biomarkers that can be quantified and used for these purposes may include (E)-2-(4,8-dimethylnona-3,7-dien-1-yl)-5-hydroxy-2,7-dimethyl-2H-chromene-8-carbaldehyde. In some embodiments, the group of diagnostic biomarkers that can be quantified and used for these purposes may include N,O-Bis-(trimethylsilyl)phenylalanine. In some embodiments, the group of diagnostic biomarkers that can be quantified and used for these purposes may include 14-HDoHE.

In some embodiments, the group of diagnostic biomarkers that can be quantified and used for detecting CRC/CRA and/or facilitating the treatment of CRC/CRA may include one or more metabolites of Table 2. In some embodiments, the group of diagnostic biomarkers that can be quantified and used for these purposes may include at least one of the metabolites of Table 2. In some embodiments, the group of diagnostic biomarkers that can be quantified and used for these purposes may include at least two of the metabolites of Table 2. In some embodiments, the group of diagnostic biomarkers that can be quantified and used for these purposes may include at least three of the metabolites of Table 2. In some embodiments, the group of diagnostic biomarkers that can be quantified and used for these purposes may include at least four of the metabolites of Table 2. In some embodiments, the group of diagnostic biomarkers that can be quantified and used for these purposes may include at least five of the metabolites of Table 2. In some embodiments, the group of diagnostic biomarkers that can be quantified and used for these purposes may include at least six of the metabolites of Table 2. In some embodiments, the group of diagnostic biomarkers that can be quantified and used for these purposes may include at least seven of the metabolites of Table 2. As another example, the group of diagnostic biomarkers that can be quantified and used for these purposes may include all of the metabolites of Table 2.

In some embodiments, the group of diagnostic biomarkers that can be quantified and used for these purposes may include at least two metabolites listed in Table 2. In some embodiments, the at least two metabolites may include 9,12,13-TriHOME and 2-octenoylcarnitine. In some embodiments, the at least two metabolites may include 9,12,13-TriHOME and (E)-2-(4,8-dimethylnona-3,7-dien-1-yl)-5-hydroxy-2,7-dimethyl-2H-chromene-8-carbaldehyde. In some embodiments, the at least two metabolites may include culinariside and 2-octenoylcarnitine. In some embodiments, the at least two metabolites may include culinariside and N,O-Bis-(trimethylsilyl)phenylalanine. In some embodiments, the at least two metabolites may include [(6-{[5,7-dihydroxy-2-(4-oxocyclohexa-2,5-dien-1-ylidene)-2H-chromen-3-yl]oxy}-3,4,5-trihydroxyoxan-2-yl)methyl][1-hydroxy-3-(4-hydroxyphenyl)prop-2-en-1-ylidene]oxidanium and 2-octenoylcarnitine. In some embodiments, the at least two metabolites may include 2-octenoylcarnitine and N,O-Bis-(trimethylsilyl)phenylalanine. In some embodiments, the at least two metabolites may include 2-octenoylcarnitine and 14-HDoHE. In some embodiments, the at least two metabolites may include (E)-2-(4,8-dimethylnona-3,7-dien-1-yl)-5-hydroxy-2,7-dimethyl-2H-chromene-8-carbaldehyde and N,O-Bis-(trimethylsilyl)phenylalanine.

In some embodiments, the group of diagnostic biomarkers that can be quantified and used for these purposes may include at least three metabolites listed in Table 3. In some embodiments, the group of diagnostic biomarkers that can be quantified and used for these purposes may include 9,12,13-TriHOME, 9,12,18-TriHOME, and N,O-Bis-(trimethylsilyl)phenylalanine. In some embodiments, the group of diagnostic biomarkers that can be quantified and used for these purposes may include 9,12,13-TriHOME, culinariside, and 2-octenoylcarnitine. In some embodiments, the group of diagnostic biomarkers that can be quantified and used for these purposes may include 9,12,13-TriHOME, [(6-{[5,7-dihydroxy-2-(4-oxocyclohexa-2,5-dien-1-ylidene)-2H-chromen-3-yl]oxy}-3,4,5-trihydroxyoxan-2-yl)methyl][1-hydroxy-3-(4-hydroxyphenyl)prop-2-en-1-ylidene]oxidanium, and 2-octenoylcarnitine. In some embodiments, the group of diagnostic biomarkers that can be quantified and used for these purposes may include 9,12,13-TriHOME, (E)-2-(4,8-dimethylnona-3,7-dien-1-yl)-5-hydroxy-2,7-dimethyl-2H-chromene-8-carbaldehyde, and N,O-Bis-(trimethylsilyl)phenylalanine. In some embodiments, the group of diagnostic biomarkers that can be quantified and used for these purposes may include 9,12,13-TriHOME, (E)-2-(4,8-dimethylnona-3,7-dien-1-yl)-5-hydroxy-2,7-dimethyl-2H-chromene-8-carbaldehyde, and N,O-Bis-(trimethylsilyl)phenylalanine. In some embodiments, the group of diagnostic biomarkers that can be quantified and used for these purposes may include 9,12,18-TriHOME, culinariside, and 2-octenoylcarnitine. In some embodiments, the group of diagnostic biomarkers that can be quantified and used for these purposes may include 9,12,18-TriHOME, culinariside, and (E)-2-(4,8-dimethylnona-3,7-dien-1-yl)-5-hydroxy-2,7-dimethyl-2H-chromene-8-carbaldehyde. In some embodiments, the group of diagnostic biomarkers that can be quantified and used for these purposes may include 9,12,18-TriHOME, [(6-{[5,7-dihydroxy-2-(4-oxocyclohexa-2,5-dien-1-ylidene)-2H-chromen-3-yl]oxy}-3,4,5-trihydroxyoxan-2-yl)methyl][1-hydroxy-3-(4-hydroxyphenyl)prop-2-en-1-ylidene]oxidanium, and 2-octenoylcarnitine. In some embodiments, the group of diagnostic biomarkers that can be quantified and used for these purposes may include 9,12,18-TriHOME, [(6-{[5,7-dihydroxy-2-(4-oxocyclohexa-2,5-dien-1-ylidene)-2H-chromen-3-yl]oxy}-3,4,5-trihydroxyoxan-2-yl)methyl][1-hydroxy-3-(4-hydroxyphenyl)prop-2-en-1-ylidene]oxidanium, and (E)-2-(4,8-dimethylnona-3,7-dien-1-yl)-5-hydroxy-2,7-dimethyl-2H-chromene-8-carbaldehyde. In some embodiments, the group of diagnostic biomarkers that can be quantified and used for these purposes may include 9,12,18-TriHOME, 2-octenoylcarnitine, and (E)-2-(4,8-dimethylnona-3,7-dien-1-yl)-5-hydroxy-2,7-dimethyl-2H-chromene-8-carbaldehyde. In some embodiments, the group of diagnostic biomarkers that can be quantified and used for these purposes may include 9,12,18-TriHOME, 2-octenoylcarnitine, and 14-HDoHE. In some embodiments, the group of diagnostic biomarkers that can be quantified and used for these purposes may include 9,12,18-TriHOME, (E)-2-(4,8-dimethylnona-3,7-dien-1-yl)-5-hydroxy-2,7-dimethyl-2H-chromene-8-carbaldehyde, and N,O-Bis-(trimethylsilyl)phenylalanine. In some embodiments, the group of diagnostic biomarkers that can be quantified and used for these purposes may include 9,12,18-TriHOME, N,O-Bis-(trimethylsilyl)phenylalanine, and 14-HDoHE. In some embodiments, the group of diagnostic biomarkers that can be quantified and used for these purposes may include culinariside, [(6-{[5,7-dihydroxy-2-(4-oxocyclohexa-2,5-dien-1-ylidene)-2H-chromen-3-yl]oxy}-3,4,5-trihydroxyoxan-2-yl)methyl][1-hydroxy-3-(4-hydroxyphenyl)prop-2-en-1-ylidene]oxidanium, and 2-octenoylcarnitine. In some embodiments, the group of diagnostic biomarkers that can be quantified and used for these purposes may include culinariside, [(6-{[5,7-dihydroxy-2-(4-oxocyclohexa-2,5-dien-1-ylidene)-2H-chromen-3-yl]oxy}-3,4,5-trihydroxyoxan-2-yl)methyl][1-hydroxy-3-(4-hydroxyphenyl)prop-2-en-1-ylidene]oxidanium, and 14-HDoHE. In some embodiments, the group of diagnostic biomarkers that can be quantified and used for these purposes may include culinariside, 2-octenoylcarnitine, and N,O-Bis-(trimethylsilyl)phenylalanine. In some embodiments, the group of diagnostic biomarkers that can be quantified and used for these purposes may include culinariside, 2-octenoylcarnitine, and 14-HDoHE. In some embodiments, the group of diagnostic biomarkers that can be quantified and used for these purposes may include [(6-{[5,7-dihydroxy-2-(4-oxocyclohexa-2,5-dien-1-ylidene)-2H-chromen-3-yl]oxy}-3,4,5-trihydroxyoxan-2-yl)methyl][1-hydroxy-3-(4-hydroxyphenyl)prop-2-en-1-ylidene]oxidanium, 2-octenoylcarnitine, and (E)-2-(4,8-dimethylnona-3,7-dien-1-yl)-5-hydroxy-2,7-dimethyl-2H-chromene-8-carbaldehyde.

In some embodiments, the group of diagnostic biomarkers that can be quantified and used for these purposes may include [(6-{[5,7-dihydroxy-2-(4-oxocyclohexa-2,5-dien-1-ylidene)-2H-chromen-3-yl]oxy}-3,4,5-trihydroxyoxan-2-yl)methyl][1-hydroxy-3-(4-hydroxyphenyl)prop-2-en-1-ylidene]oxidanium, 2-octenoylcarnitine, and N,O-Bis-(trimethylsilyl)phenylalanine.

In some embodiments, the group of diagnostic biomarkers that can be quantified and used for these purposes may include [(6-{[5,7-dihydroxy-2-(4-oxocyclohexa-2,5-dien-1-ylidene)-2H-chromen-3-yl]oxy}-3,4,5-trihydroxyoxan-2-yl)methyl][1-hydroxy-3-(4-hydroxyphenyl)prop-2-en-1-ylidene]oxidanium, 2-octenoylcarnitine, and 14-HDoHE. In some embodiments, the group of diagnostic biomarkers that can be quantified and used for these purposes may include [(6-{[5,7-dihydroxy-2-(4-oxocyclohexa-2,5-dien-1-ylidene)-2H-chromen-3-yl]oxy}-3,4,5-trihydroxyoxan-2-yl)methyl][1-hydroxy-3-(4-hydroxyphenyl)prop-2-en-1-ylidene]oxidanium, (E)-2-(4,8-dimethylnona-3,7-dien-1-yl)-5-hydroxy-2,7-dimethyl-2H-chromene-8-carbaldehyde, and N,O-Bis-(trimethylsilyl)phenylalanine. In some embodiments, the group of diagnostic biomarkers that can be quantified and used for these purposes may include [(6-{[5,7-dihydroxy-2-(4-oxocyclohexa-2,5-dien-1-ylidene)-2H-chromen-3-yl]oxy}-3,4,5-trihydroxyoxan-2-yl)methyl][1-hydroxy-3-(4-hydroxyphenyl)prop-2-en-1-ylidene]oxidanium, 2-octenoylcarnitine, and 14-HDoHE.

In some embodiments, the group of diagnostic biomarkers that can be quantified and used for these purposes may include 2-octenoylcarnitine, (E)-2-(4,8-dimethylnona-3,7-dien-1-yl)-5-hydroxy-2,7-dimethyl-2H-chromene-8-carbaldehyde, and 14-HDoHE. In some embodiments, the group of diagnostic biomarkers that can be quantified and used for these purposes may include 2-octenoylcarnitine, N,O-Bis-(trimethylsilyl)phenylalanine, and 14-HDoHE.

The metabolites (biomarkers) listed in Table 1 provide a panel that can be used for detecting CRC/CRA and/or facilitating the treatment of CRC/CRA. Nevertheless, in some embodiments, the group of diagnostic biomarkers provided by the present disclosure may include one or more other metabolites that are not listed in Table 1. For example, the group of diagnostic biomarkers provided by the present disclosure may include at least one metabolite of Table 3. Each of the metabolites in Table 3 may be associated with gut microbiome. Each of the metabolites in Table 3 is found to be closely correlated with the presence of CRC/CRA. In some embodiments, one or more of the metabolites in Table 3 may be used, independently from the metabolites listed in Table 1 or Table 2, for detecting and/or facilitating the treatment of CRC/CRA in the subject. In some embodiments, one or more of the metabolites in Table 3 may be used, addition to the metabolites listed in Table 1 or Table 2, for detecting and/or facilitating the treatment of CRC/CRA in the subject. In some embodiments, the abundance of one or more metabolites in Table 3 may be quantified, e.g., with mass spectrometry, and processed for detecting CRC/CRA and/or facilitating the treatment of CRC/CRA. In some embodiments, the abundance of one or more metabolites in Table 3 may be quantified, e.g., with mass spectrometry, grouped with the quantified abundance of one or more metabolites of Table 1 or Table 2, and processed for detecting CRC/CRA and/or facilitating the treatment of CRC/CRA. In some embodiments, the abundance of only 1, 2, 3, 4, 5, 6, 7, 8, 9, 10, 11, 12, 13, 14, 15, 16, 17, 18, 19, 20, 21 or 22 metabolites of the metabolites in Table 3 are quantified. In some embodiments, the abundance of all 23 metabolites of the metabolites in Table 3 are quantified. As indicated, the quantified abundance of the metabolites of Table 3 can be used independently of the quantified abundance of the metabolites of Table 1 or Table 2, or can be grouped together with the quantified abundance of the metabolites of Table 1 or Table 2.

In certain embodiments, all eight metabolites of Table 1 or Table 2, as well as only one metabolite of Table 3, are quantified, grouped together, processed, and used for detecting CRC/CRA and/or facilitating the treatment of CRC/CRA in the subject. In certain embodiments, all eight metabolites of Table 1 or Table 2, as well as only 2, 3, 4, 5, 6, 7, 8, 9, 10, 11, 12, 13, 14, 15, 16, 17, 18, 19, 20, 21 or 22 metabolites of Table 3, are quantified, grouped together, processed, and used for detecting CRC/CRA and/or facilitating the treatment of CRC/CRA in the subject. In certain embodiments, all eight metabolites of Table 1 or Table 2, as well as all 23 metabolites of Table 3, are quantified, grouped together, processed, and used for detecting CRC/CRA and/or facilitating the treatment of CRC/CRA in the subject.

In certain embodiments, only 1, 2, 3, 4, 5, 6, or 7 metabolites of Table 1 or Table 2, as well as only one metabolite of Table 3, are quantified, grouped together, processed, and used for detecting CRC/CRA and/or facilitating the treatment of CRC/CRA in the subject. In certain embodiments, 1, 2, 3, 4, 5, 6, or 7 metabolites of Table 1 or Table 2, as well as only 2, 3, 4, 5, 6, 7, 8, 9, 10, 11, 12, 13, 14, 15, 16, 17, 18, 19, 20, 21 or 22 metabolites of Table 3, are quantified, grouped together, processed, and used for detecting CRC/CRA and/or facilitating the treatment of CRC/CRA in the subject. In certain embodiments, 1, 2, 3, 4, 5, 6, or 7 metabolites of Table 1 or Table 2, as well as all 23 metabolites of Table 3, are quantified, grouped together, processed, and used for detecting CRC/CRA and/or facilitating the treatment of CRC/CRA in the subject.

TABLE 3

| No. | MASS(+/−) | Compound | Delta(ppm) |
|---|---|---|---|
| 1 | 193.09(−) | C6H14OS | 2 |
| 2 | 380.033(−) | C15H15N3O5S2 | 13 |
| 3 | 289.164(+) | C15H22O5 | 4 |
| 4 | 750.519(+) | C39H76NO10P | 12 |
| 5 | 357.228(−) | C15H30N6O4 | 7 |
| 6 | 637.105(+) | C23H22F7N4O6P | 1 |
| 7 | 612.425(+) | C37H54O6 | 1 |
| 8 | 512.336(−) | C27H45NO | 1 |
| 9 | 543.376(+) | C35H52O3 | 9 |
| 10 | 490.686(+) | C80H152O17P2 | 3 |
| 11 | 483.297(−) | C26H44O8 | 1 |
| 12 | 319.264(−) | C21H36O2 | 1 |
| 13 | 447.312(−) | C27H44O5 | 1 |
| 14 | 279.233(−) | C18H32O2 | 0 |
| 15 | 578.25(+) | C28H37N5O7 | 15 |
| 16 | 572.415(+) | C29H60NO7P | 21 |
| 17 | 461.196(+) | C26H30O6 | 6 |
| 18 | 475.116(−) | C19H24O14 | 14 |
| 19 | 513.363(+) | C32H48O5 | 11 |
| 20 | 502.015(+) | C16H22BrN3O7S | 21 |
| 21 | 384.259(+) | C22H35NO3 | 21 |
| 22 | 197.068(−) | C7H10N4O3 | 0 |
| 23 | 584.729(+) | C43H74N7O17P3S | 15 |

As yet another example, the group of diagnostic biomarkers provided by the present disclosure may include one or more metabolites of Table 4. In some embodiments, the group of diagnostic biomarkers provided by the present disclosure may further include all the metabolites of Table 4. Each of the metabolites in Table 4 may be associated with gut microbiome. Each of the metabolites in Table 4 is found to be correlated with the presence of CRC/CRA. In some embodiments, one or more of the metabolites in Table 4 may be used, independently from the metabolites listed in Table 1, Table 2, or Table 3, for detecting and/or facilitating the treatment of CRC/CRA in the subject. In some embodiments, one or more of the metabolites in Table 4 may be used, addition to the metabolites listed in Table 1 or Table 2, for detecting and/or facilitating the treatment of CRC/CRA in the subject. In some embodiments, one or more of the metabolites in Table 4 may be used, addition to the metabolites listed in Table 1, Table 2, and Table 3, for detecting and/or facilitating the treatment of CRC/CRA in the subject. In some embodiments, the abundance of only 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 metabolites of the metabolites in Table 4 are quantified. In some embodiments, the abundance of all 51 metabolites of the metabolites in Table 4 are quantified. As indicated, the quantified abundance of the metabolites of Table 4 can be used independently of the quantified abundance of the metabolites of Table 1 or Table 2, and Table 3, or can be grouped together with the quantified abundance of the metabolites of Table 1 or Table 2, and Table 3.

In certain embodiments, all eight metabolites of Table 1 or Table 2, as well as only one metabolite of Table 4, are quantified, grouped together, processed, and used for detecting CRC/CRA and/or facilitating the treatment of CRC/CRA in the subject. In certain embodiments, all eight metabolites of Table 1 or Table 2, as well as only 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 metabolites of Table 4, are quantified, grouped together, processed, and used for detecting CRC/CRA and/or facilitating the treatment of CRC/CRA in the subject. In certain embodiments, all eight metabolites of Table 1 or Table 2, as well as all 51 metabolites of Table 4, are quantified, grouped together, processed, and used for detecting CRC/CRA and/or facilitating the treatment of CRC/CRA in the subject.

In certain embodiments, only 1, 2, 3, 4, 5, 6, or 7 metabolites of Table 1 or Table 2, as well as only one metabolite of Table 4, are quantified, grouped together, processed, and used for detecting CRC/CRA and/or facilitating the treatment of CRC/CRA in the subject. In certain embodiments, 1, 2, 3, 4, 5, 6, or 7 metabolites of Table 1 or Table 2, as well as only 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 metabolites of Table 4, are quantified, grouped together, processed, and used for detecting CRC/CRA and/or facilitating the treatment of CRC/CRA in the subject. In certain embodiments, 1, 2, 3, 4, 5, 6, or 7 metabolites of Table 1 or Table 2, as well as all 51 metabolites of Table 4, are quantified, grouped together, processed, and used for detecting CRC/CRA and/or facilitating the treatment of CRC/CRA in the subject.

TABLE 4

| No. | MASS(+/−) | Compound | Delta(ppm) |
|---|---|---|---|
| 1 | 193.09(−) | C11H14O3 | 15 |
| 2 | 223.134(−) | C13H20O3 | 0 |
| 3 | 289.106(−) | C16H18O5 | 7 |
| 4 | 355.227(+) | C21H32O3 | 7 |
| 5 | 382.183(+) | C20H25NO6 | 3 |
| 6 | 386.067(−) | C14H15NO9 | 15 |
| 7 | 398.179(−) | C22H29N3S2 | 15 |
| 8 | 447.311(−) | C27H44O5 | 1 |
| 9 | 461.195(+) | C28H28O6 | 2 |
| 10 | 462.141(−) | C19H20FN5O5 | 4 |
| 11 | 471.005(+) | C16H16O11S2 | 5 |
| 12 | 476.011(+) | C10H16N5O11P3 | 5 |
| 13 | 476.358(+) | C30H42O2 | 12 |
| 14 | 477.13(+) | C28H22O6 | 2 |
| 15 | 483.368(+) | C30H52O2 | 17 |
| 16 | 494.68(+) | C83H150O17P2 | 11 |
| 17 | 495.024(+) | C21H12O14 | 30 |
| 18 | 504.692(+) | C12H6Br4O | 25 |
| 19 | 509.03(+) | C10H16N5O12P3 | 9 |
| 20 | 514.027(+) | C10H17N7O12S2 | 0 |
| 21 | 514.705(+) | C44H61N13O12S2 | 5 |
| 22 | 519.043(+) | C20H16O15 | 9 |
| 23 | 531.178(−) | C27H32O11 | 17 |
| 24 | 534.052(+) | C16H17N9O5S3 | 21 |
| 25 | 536.299(−) | C23H44NO7P | 1 |
| 26 | 539.384(+) | C32H52O5 | 25 |
| 27 | 542.426(+) | C54H106NO10P | 2 |

TABLE 4-continued

| No. | MASS(+/−) | Compound | Delta(ppm) |
|---|---|---|---|
| 28 | 543.378(+) | C35H52O3 | 5 |
| 29 | 549.062(+) | C22H22O14 | 4 |
| 30 | 563.068(+) | C30H20O9 | 10 |
| 31 | 567.155(−) | C28H28N2O11 | 12 |
| 32 | 568.075(+) | C21H18O14S | 1 |
| 33 | 587.088(+) | C25H24O13S | 9 |
| 34 | 597.091(+) | C26H22O15 | 10 |
| 35 | 616.463(+) | C37H58O6 | 9 |
| 36 | 629.391(−) | C40H56O7 | 11 |
| 37 | 631.103(−) | C28H24O17 | 14 |
| 38 | 646.473(+) | C35H68NO7P | 12 |
| 39 | 702.536(+) | C39H76NO7P | 10 |
| 40 | 732.546(+) | C41H76NO7P | 8 |
| 41 | 776.038(+) | C27H20O21S | 1 |
| 42 | 804.604(+) | C45H84NO8P | 7 |
| 43 | 877.609(+) | C44H85NO11S | 10 |
| 44 | 938.662(+) | C54H94NO8P | 1 |
| 45 | 950.698(+) | C54H97NO10P | 14 |
| 46 | 994.724(+) | C54H101NO13 | 8 |
| 47 | 1038.751(+) | C65H98O6 | 1 |
| 48 | 1040.729(+) | C56H107NO13 | 8 |
| 49 | 432.109(−) | C21H21O10 | 6 |
| 50 | 635.934(+) | C64H120N2O21 | 9 |
| 51 | 714.829(+) | C65H102O33 | 9 |

The AUC, specificity, and sensitivity of the prediction model utilizing the abundance of at least one of the metabolites listed in Table 1, Table 2, Table 3, and/or Table 4 are relatively high, indicating that the prediction model utilizing the abundance of these metabolites may effectively distinguish subjects with CRC/CRA from normal subjects.

Table 5 shows some information of the metabolites listed in Table 1. The feature of the metabolites in Table 5 refers to the mass-to-charge ratio, which can be measured, for example, using mass spectrometry. The term "Fold change" in Table 5 refers to a parameter describing how much a quantity changes between an original and a subsequent measurement. The term "P-value" in Table 5 refers to the probability, under the null hypothesis about the unknown distribution of the test statistic, to have observed a value as extreme or more extreme than the value actually observed.

TABLE 5

| No. | Metabolite | Mass-to-charge ratio | Fold Change | p-value |
|---|---|---|---|---|
| 1 | 9,12,13-TriHOME | 331.240/285.222-2 | 1.19 | 9.16E−02 |
| 2 | 9,12,18-TriHOME | 331.240/285.222-4 | 0.51 | 2.49E−09 |
| 3 | culinariside | 420.807/376.259 | 0.87 | 4.24E−01 |
| 4 | [(6-{[5,7-dihydroxy-2-(4-oxocyclohexa-2,5-dien-1-ylidene)-2H-chromen-3-yl]oxy}-3,4,5-trihydroxyoxan-2-yl)methyl][1-hydroxy-3-(4-hydroxyphenyl)prop-2-en-1-ylidene]oxidanium | 637.157/253.072 | 0.80 | 4.42E−03 |
| 5 | 2-octenoylcarnitine | 398.180/150.002 | 10.83 | 1.67E−07 |
| 6 | (E)-2-(4,8-dimethylnona-3,7-dien-1-yl)-5-hydroxy-2,7-dimethyl-2H-chromene-8-carbaldehyde | 353.212/177.092 | 3.34 | 4.37E−10 |
| 7 | N,O-Bis-(trimethylsilyl)phenylalanine | 368.169/150.002 | 8.02 | 4.39E−10 |
| 8 | 14-HDoHE | 355.228/163.113 | 2.98 | 9.86E−08 |

It should be noted that one or more of the metabolites listed in Table 1, 3, or 4 may have one or more isomeride forms, which are included in the scope of the group of diagnostic biomarkers provided by the present disclosure.

According to another aspect of the present disclosure, a method of detecting CRC/CRA in a subject is provided. In some embodiments, the method may include step a): quantifying the abundance of one or more components of a panel of a plurality of metabolites in a sample from the subject. The plurality of metabolites may include the metabolites listed in Table 1, Table 2, Table 3, and/or Table 4, as described earlier in the present disclosure. In some embodiments, the method may further include determining a sample score by processing the abundance of each of the metabolites quantified in step a). In some embodiments, the method may further include step c): detecting CRC/CRA in the subject by comparing the sample score to a cut-off score.

In some embodiments, the abundance of the one or more components of the panel of the plurality of metabolites may be measured using mass spectrometry (MS; e.g., liquid chromatography-mass spectrometry (LC-MS), gas chromatography-mass spectrometry (GC-MS); matrix-assisted laser desorption/ionization time-of-flight mass spectrometry (MALDI-TOF MS)), ultraviolet spectrometry, or the like.

In some embodiments, the determination of the sample score may be implemented on a computing device. The computing device may obtain a prediction model for determining the sample score. The abundance of each of the metabolites quantified in step a) may be inputted into the prediction model. The prediction model may process the abundance of each of the metabolites quantified in step a) and output the sample score. The sample score may indicate a probability that the subject has CRC/CRA.

Merely by way of example, the abundance of each of the metabolites quantified in step a) may be quantified by measuring the concentration of each of the metabolites. In some embodiments, the measured concentration may be normalized. For instance, the measured concentration may be divided by a total concentration of all metabolites in the sample.

In some embodiments, the prediction model may be a trained model. A preliminary model may be obtained and trained using a plurality of training datasets. Each of the plurality of training datasets may include a concentration of a sample metabolite of a sample subject and a label indicating whether the sample subject has CRC/CRA or is normal. The plurality of sample subjects may include a plurality of normal subjects who do not CRC/CRA, a plurality of subjects having CRC, and a plurality of subjects having CRA. Merely by way of example, the label may be a value between 0-1. If a sample subject is normal, the value of the corresponding label may be designated as 0. If a sample subject has CRC/CRA, the value of the corresponding label may be designated as 1. Accordingly, the sample score outputted by the prediction model may be a value between 0 and 1. The closer the sample score is to 1, the higher the probability that the subject has CRC/CRA is.

In some embodiments, the prediction model may be established by a logistic regression method, a method based on support vector machine (SVM), a method based on Bayes classifier, a method based on K-nearest neighbors (KNN), a decision tree method, or the like, or any combination thereof.

In step c), the sample score is compared to a cut-off score related to the prediction model. As used herein, the term "cut-off value" refers to a dividing point on measuring scales where test results are divided into different categories. In some embodiments, when the sample score is equal to or greater than the cut-off score, the computing device may determine that the subject has CRC/CRA. The cut-off value may be determined based on the performance of the prediction model. In some embodiments, the cut-off value may be a value between 0.35-0.65. In some embodiments, the cut-off value may be a value between 0.40-0.60. In some embodiments, the cut-off value may be a value between 0.45-0.55. For example, the cut-off value may be 0.48, 0.50, 0.52, 0.541, 0.55, etc.

In some embodiments, a receiver operating characteristic (ROC) curve may be used to evaluate the performance of the prediction model. The ROC curve may illustrate the diagnostic ability of the prediction model as its cut-off value is varied. The ROC curve is usually generated by plotting the sensitivity against the specificity. An area-under-the-curve (AUC) may be determined based on the ROC curve. The AUC may indicate the probability that a classifier (i.e., the prediction model) will rank a randomly chosen positive instance higher than a randomly chosen negative one.

In some embodiments, the AUC of the prediction model provided by the present disclosure is more than 0.7. In some embodiments, the AUC of the prediction model provided by the present disclosure is more than 0.75. In some embodiments, the AUC of the prediction model provided by the present disclosure is more than 0.77. In some embodiments, the AUC of the prediction model provided by the present disclosure is more than 0.8. In some embodiments, the AUC of the prediction model provided by the present disclosure is more than 0.85. In some embodiments, the AUC of the prediction model provided by the present disclosure is more than 0.9. In some embodiments, the AUC of the prediction model provided by the present disclosure is more than 0.95.

In some embodiments, the sensitivity of the prediction model for detecting CRC/CRA is equal to or greater than 70%. In some embodiments, the sensitivity of the prediction model for detecting CRC/CRA is equal to or greater than 75. In some embodiments, the sensitivity of the prediction model for detecting CRC/CRA is equal to or greater than 80%. In some embodiments, the sensitivity of the prediction model for detecting CRC/CRA is equal to or greater than 85%. In some embodiments, the sensitivity of the prediction model for detecting CRC/CRA is equal to or greater than 90%. In some embodiments, the sensitivity of the prediction model for detecting CRC/CRA is equal to or greater than 95%.

In some embodiments, the specificity of the prediction model for detecting CRC/CRA is equal to or greater than 70%. In some embodiments, the specificity of the prediction model for detecting CRC/CRA is equal to or greater than 75. In some embodiments, the specificity of the prediction model for detecting CRC/CRA is equal to or greater than 80%. In some embodiments, the specificity of the prediction model for detecting CRC/CRA is equal to or greater than 85%. In some embodiments, the specificity of the prediction model for detecting CRC/CRA is equal to or greater than 90%. In some embodiments, the specificity of the prediction model for detecting CRC/CRA is equal to or greater than 95%.

Figure 3A:
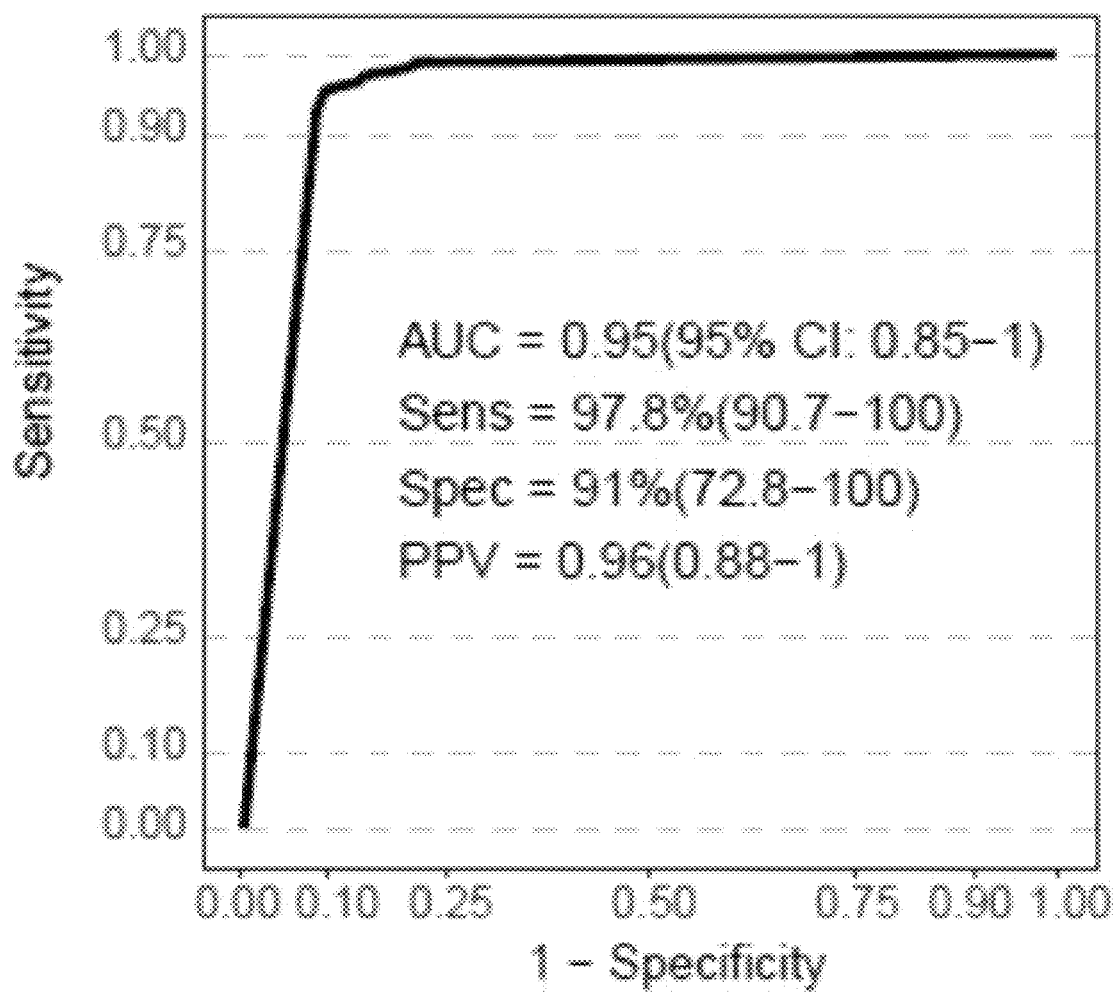
FIG. 3A is a ROC for a prediction model utilizing the abundance of the 8 metabolites listed in Table A according to a validation set.

FIG. 3A is a ROC for a prediction model utilizing the abundance of the 8 metabolites listed in Table 1 according to a validation set based on an untargeted metabolomics analysis. Specifically, the ROC in FIG. 3A relates to an exemplary prediction model which utilizes the abundance of the 8 metabolites listed in Table 1 to determine the sample score. It should be noted that the prediction model provided by the present disclosure may utilize the abundance of at least one of the 8 metabolites listed in Table 1. The ROC in FIG. 3A is only provided for illustration purposes. As shown in FIG. 3A, the AUC is about 0.95, the sensitivity is about 95.4%, and the specificity is about 94%. As used herein, the term "about" means that a value can vary within a relatively small range (e.g., ±0.02 or ±0.05%).

Figure 4A:
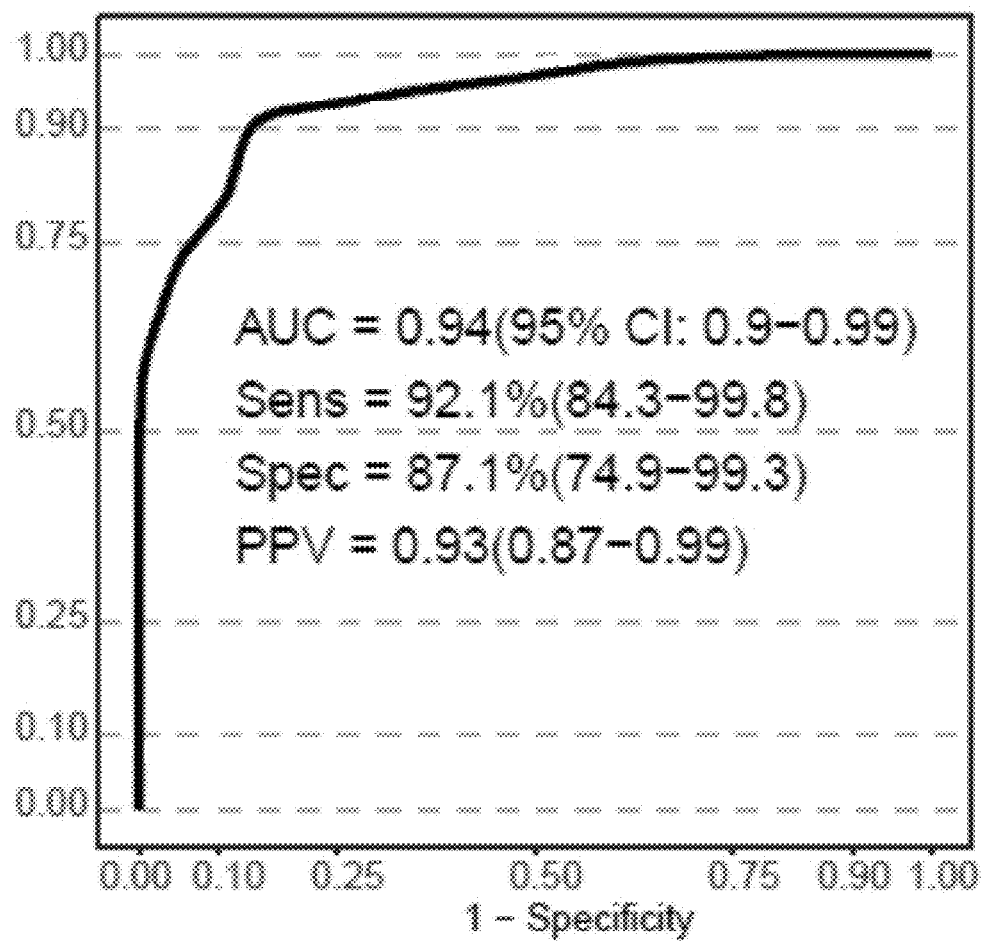
FIG. 4A is an analytical diagram illustrating a ROC curve showing discriminate efficiencies of GMSM panel in the modeling group according to some embodiments of the present disclosure.
Figure 4B:
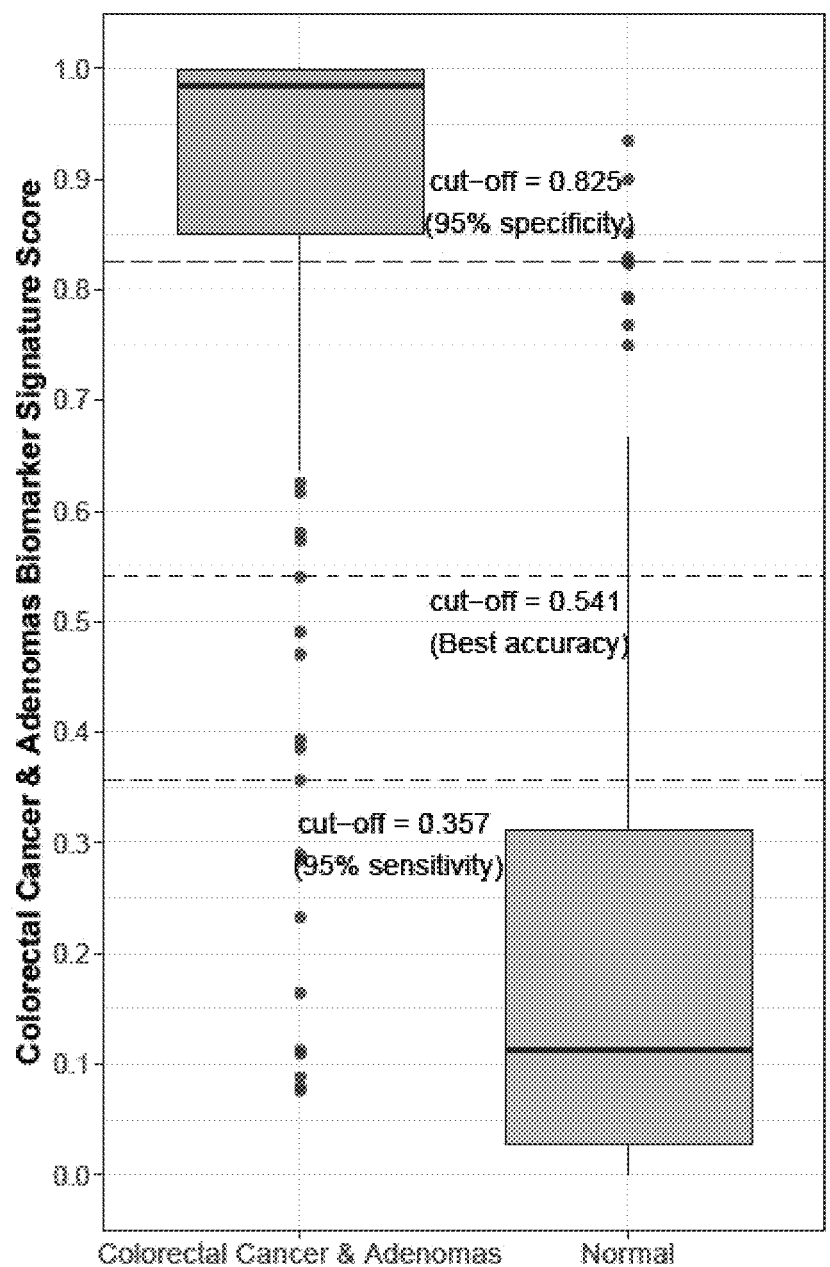
FIG. 4B is an analytical diagram illustrating CRC and adenomas biomarker signature scores of normal and colorectal abnormal subjects in modeling group according to some embodiments of the present disclosure.
Figure 4C:
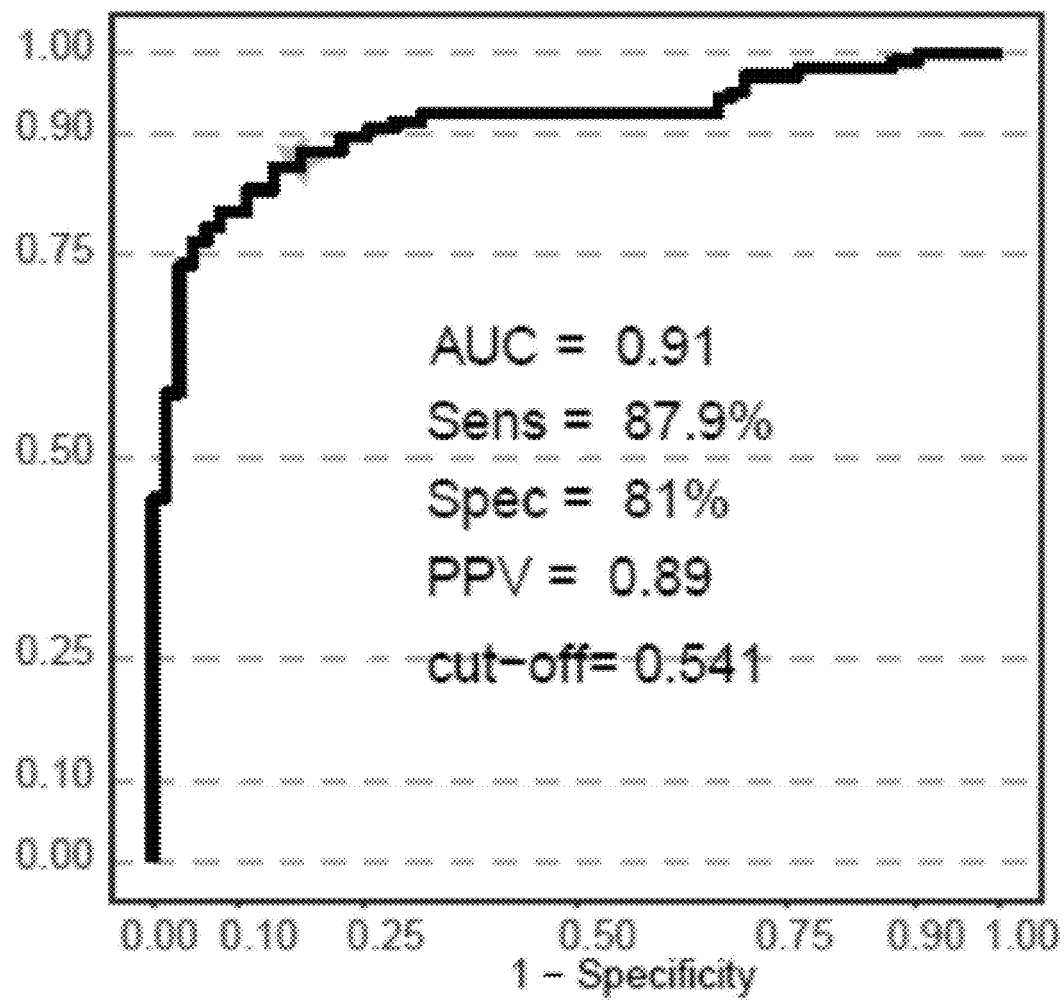
FIG. 4C illustrates a ROC curve showing discriminate efficiencies of the prediction model in the validation group under the cut-off score of 0.541 according to some embodiments of the present disclosure.

FIG. 4C illustrates a ROC curve showing discriminate efficiencies of the prediction model in the validation group under the cut-off score of 0.541. As shown in FIG. 4C, the prediction model reached an AUC of 0.91, a sensitivity of 87.9%, and a specificity of 81% in this validation set.

More description regarding the discriminate efficiency of the prediction model utilizing various groups of diagnostic biomarkers may be found elsewhere in the present disclosure, for example, in Example 7 and Example 8. As shown in these Examples, the AUC, specificity, and sensitivity of the prediction model are relatively high, indicating that the prediction model utilizing the abundance of these metabolites may effectively distinguish subjects with CRC/CRA from normal subjects.

In some embodiments, the method for detecting CRC/CRA may further include verifying the CRC/CRA using other approaches, such as colonoscopy, a biopsy test, a computerized tomography (CT) scan, a magnetic resonance imaging (MRI) scan, or the like, or any combination thereof.

According to another aspect of the present disclosure, a method of detecting CRA in a subject is provided. The method may include step a): quantifying abundance of at least five components of a panel of a plurality of metabolites in a sample from the subject. The method may further include step b): determining a sample score by processing the abundance of each of the metabolites quantified in step a). The method may still further include step c): detecting CRA in the subject by comparing the evaluation value to a cut-off value. In some embodiments, the plurality of metabolites may include the metabolites listed in Table 1, Table 2, Table 3, and/or Table 4, as described earlier in the present disclosure.

In some embodiments, step b) may further include normalizing the abundance of each of the metabolites quantified in step (a), and determining the sample score by processing the normalized abundance with a prediction model. The prediction model may be established using a plurality of training datasets. For example, each of the plurality of training datasets may include a concentration of a sample metabolite of a sample subject and a label indicating whether the sample subject has CRC or is normal. The plurality of sample subjects may include a plurality of normal subjects who do not have CRC and a plurality of subjects having CRC.

In some embodiments, the prediction model may be used to distinguishing normal people from CRC patients in different stages. In some embodiments, the plurality of sample subjects having CRC may include a plurality of subjects having a pre-cancer stage (stage 0) CRC. In some embodiments, the plurality of sample subjects having CRC may include a plurality of subjects having an early stage (stage I) CRC. In some embodiments, the plurality of sample subjects having CRC may include a plurality of subjects having a middle stage (stage II) CRC. In some embodiments, the plurality of sample subjects having CRC may include a plurality of subjects having a late stage (stage III and IV) CRC. In some embodiments, the prediction model for detecting CRC may be established in a manner similar to the prediction model for detecting CRC/CRA as described earlier in the present disclosure.

In some embodiments, the sensitivity of the prediction model for detecting CRC is equal to or greater than 65%. In some embodiments, the sensitivity of the prediction model for detecting CRC is equal to or greater than 70%. In some embodiments, the sensitivity of the prediction model for detecting CRC is equal to or greater than 75%. In some embodiments, the sensitivity of the prediction model for detecting CRC is equal to or greater than 80%. In some embodiments, the sensitivity of the prediction model for detecting CRC/CRA is equal to or greater than 85%. In some embodiments, the sensitivity of the prediction model for detecting CRC is equal to or greater than 90%.

In some embodiments, the specificity of the prediction model for detecting CRC is equal to or greater than 70%. In some embodiments, the specificity of the prediction model for detecting CRC is equal to or greater than 75%. In some embodiments, the specificity of the prediction model for detecting CRC is equal to or greater than 80%. In some embodiments, the specificity of the prediction model for detecting CRC is equal to or greater than 85%. In some embodiments, the specificity of the prediction model for detecting CRC is equal to or greater than 90%.

For instance, as will be described in Example 6, a prediction model for detecting CRC was used for distinguishing subjects having stage 0/I CRC from normal subjects and had an AUC of 0.85, a sensitivity of 82.1%, and a specificity of 81% (see, e.g., FIG. 6B). The prediction model for detecting CRC was also used for distinguishing subjects having stage II CRC from normal subjects and had an AUC of 0.89, a sensitivity of 88.9%, and a specificity of 81% (see, e.g., FIG. 6C). The prediction model for detecting CRC was also used for distinguishing subjects having stage III/IV CRC from normal subjects and had an AUC of 0.91, a sensitivity of 85%, and a specificity of 81%.

According to yet another aspect of the present disclosure, a method of detecting stage I/II CRC in a subject is provided. The method may include (a) quantifying abundance of one or more components of a panel of a plurality of metabolites in a sample from the subject with mass spectrometry, wherein the plurality of metabolites include the metabolites of Table 1; (b) determining a sample score by processing the concentration of each of the metabolites quantified in step (a); and (c) detecting stage I/II CRC in the subject by comparing the evaluation value to a cut-off value. In some embodiments, the plurality of metabolites may include the metabolites listed in Table 1, Table 2, Table 3, and/or Table 4, as described earlier in the present disclosure.

In some embodiments, step b) may further include normalizing the abundance of each of the metabolites quantified in step (a), and determining the sample score by processing the normalized abundance with a prediction model. The prediction model may be established using a plurality of training datasets. For example, each of the plurality of training datasets may include a concentration of a sample metabolite of a sample subject and a label indicating whether the sample subject has a stage I/II CRC or is normal. The plurality of sample subjects may include a plurality of normal subjects who do not have CRC and a plurality of subjects having a stage I/II CRC.

According to yet another aspect of the present disclosure, a method of detecting stage III/IV CRC in a subject is provided. The method may include (a) quantifying abundance of one or more components of a panel of a plurality of metabolites in a sample from the subject with mass spectrometry, wherein the plurality of metabolites include the metabolites of Table 1; (b) determining a sample score by processing the concentration of each of the metabolites quantified in step (a); and (c) detecting stage III/IV CRC in the subject by comparing the evaluation value to a cut-off value. In some embodiments, the plurality of metabolites may include the metabolites listed in Table 1, Table 2, Table 3, and/or Table 4, as described earlier in the present disclosure.

In some embodiments, step b) may further include normalizing the abundance of each of the metabolites quantified in step (a), and determining the sample score by processing the normalized abundance with a prediction model. The prediction model may be established using a plurality of training datasets. For example, each of the plurality of training datasets may include a concentration of a sample metabolite of a sample subject and a label indicating whether the sample subject has a stage III/IV CRC or is normal. The plurality of sample subjects may include a plurality of normal subjects who do not have CRC and a plurality of subjects having a stage III/IV CRC.

According to still another aspect of the present disclosure, a method of treating CRC/CRA in a subject is provided. The method may include detecting CRC/CRA according to the methods described earlier in the present disclosure, and applying treatment to the subject for CRC/CRA.

In some embodiments, the method for treating CRC/CRA may further include verifying the CRC/CRA using other approaches, such as colonoscopy, a biopsy test, a computerized tomography (CT) scan, a magnetic resonance imaging (MRI) scan, or the like, or any combination thereof. In some embodiments, the process of the present disclosure may further include ordering the verification of the CRC/CRA with colonoscopy, a biopsy test, a computerized tomography (CT) scan, a magnetic resonance imaging (MRI) scan, or the like, or any combination thereof. In certain embodiments, these approaches can be used to distinguish between CRC and CRA, so that proper treatment can be applied.

In some embodiments, the treatment may include chemotherapy, radiation therapy, targeted drug therapy, immunotherapy, or the like, or any combination thereof. In some embodiments, the treatment may include palliative care. For instance, when the subject is diagnosed with late stage CRC and other treatment approaches turn out to be ineffective, palliative care may be provided for the subject to mitigate the pain and stress of the subject. "Treatment of CRC/CRA," or "treatment of CRC," as used herein, refers to partially or totally inhibiting, delaying, or preventing the progression of colorectal cancer including cancer metastasis; inhibiting, delaying, or preventing the recurrence of cancer including cancer metastasis; or preventing the onset or development of cancer (chemoprevention) in a mammal, for example, a human. In addition, the methods of the present invention may be practiced for the treatment of human patients with cancer. However, it is also likely that the methods would also be effective in the treatment of cancer in other mammals.

According to still another aspect of the present disclosure, a method of identifying gut microbiome-associated (GMA) metabolites as biomarkers for a prediction panel for CRC/CRA is provided. In some embodiments, the method may include obtaining source data by conducting untargeted mass spectrometry to samples from CRC/CRA patients and control group of persons not having CRC/CRA. The method may further include identifying a first group of metabolites that are significantly altered in the CRC/CRA patients. A second group of metabolites may be identified from the first group by selecting metabolites that show a significant correlation with gut microbiome. The method may further include selecting the GMA metabolites for the prediction panel from the second group of metabolites using a selection model.

In some embodiments, a metabolomics profiling analysis may be performed using the source data to identify the first group of metabolites.

In some embodiments, the second group of metabolites may be selected from the first group of metabolites through a correlation analysis. For example, a Pearson correlation coefficient analysis may be carried out within the CRC/CRA patients to profile gut microbiome species with relative abundance higher than a first threshold and metabolites with abundance higher than a second threshold. For instance, the relative abundance of a specific gut microbiome species may be determined based on a ratio of the amount of microbiome species to the amount of all microbiome species in a sample. The relative abundance of the metabolites may be determined based on total of count for MS/MS detected fragments corresponding metabolites. For example, the first threshold may be a value between 0.01%-1%, such as 0.01%, 0.05%, 0.1%, 0.5%, etc. As another example, the second threshold may be a value between 1000-20000, such as 1000, 3000, 5000, 10000, 12000, 15000, 18000, 20000, etc.

In some embodiments, the gut microbiome species and their abundance may be detected using fecal samples from CRC/CRA patients and the control group of persons not having CRC/CRA. The gut microbiome species and their abundance in the fecal samples may be detected using metagenome sequencing. For example, nucleic acid may be extracted from the fecal samples for metagenome sequencing.

In some embodiments, the GMA metabolites for the prediction panel may be selected from the second group of metabolites using a selection model. For instance, the selection model may be a model based on a regression algorithm. The regression algorithm may include but not limited to a Least Absolute Shrinkage and Selection Operator (LASSO) algorithm, a Linear Regression algorithm, a Polynomial Regression algorithm, a ridge regression algorithm, an ElasticNet Regression algorithm, or the like, or any combination thereof.

In some embodiments, to determine the GMA metabolites for the prediction panel, the stability of diagnostic efficiency of the metabolites selected using the selection model may be further evaluated. For example, if a metabolite exhibits consistent up or down-regulation trend in untargeted and targeted detection, the diagnostic efficiency of the metabolite is considered to be stable. Additionally or alternatively, if the metabolite can be stably measured using different approaches (e.g., targeted LC-MS detection, untargeted metabolome), the diagnostic efficiency of the metabolite is considered to be stable.

The methods and metabolite biomarkers provided by the present disclosure are further described according to the following examples, which should not be construed as limiting the scope of the present disclosure.

EXAMPLES

Methods

Serum Cohort for CRC Metabolomics Profiling

A serum cohort was established by randomly selecting 512 subjects aged between 45 to 75 between 2017 to 2019 Subjects who received preoperative radiation or chemotherapy treatment or had a past history of CRC were excluded. The serum cohort was divided into three sets, namely a discovery set, a modeling set, and a validation set. The discovery set included 92 subjects classified into three groups, named as a normal group, an adenoma group, and a colorectal cancer group. The normal group (or N in short) included 31 subjects. The adenoma group (or A in short) included 12 subjects. The colorectal cancer group (or C in short) included 49 subjects. The modeling set included 265 subjects, of which 97 subjects were normal and 168 subjects were colorectal abnormal patients. 30% of subjects in the modeling set were randomly selected into a training set and the rest was selected into a testing set. The validation set included 189 subjects, including 69 normal subjects, and 120 colorectal abnormal patients. Pathological diagnosis and stage were determined based on the tumor-node-metastasis (TNM) staging system maintained by the American Joint Committee on Cancer and the International Union for Cancer Control. Blood of subjects in the three sets was sampled before treatment.

Fecal-Serum Matched Cohort

A fecal-serum matched cohort (or referred to as matched cohort) included 55 subjects was established, of which 16 subjects were normal and 39 subjects were patients with colorectal cancer or adenoma. Both stool and serum were collected from the same subjects. Stool samples were snap frozen by liquid nitrogen and stored at −80° C. until further usage.

Metabolite Extraction for Untargeted Metabolomics Detection

For metabolite extraction in untargeted metabolomics detection, 240 ml of acetonitrile/isopropanol (3:1, by volume) was added to 60 ml of previously thawed serum samples, reaching a serum solution in a volume of 300 ml. To precipitate serum proteins, 60 μL of ammonium formate (0.5 g/ml) was added to the serum solution along with 6 μL of internal standard solution (containing 100 ug/ml of L-tyrosine-(phenyl-3,5-d2), Sigma-Aldrich; 10 ug/ml of 13C-cholic acid, Cambridge Isotope Laboratories; 60 ug/ml of doxercalciferol, MedChem Express) to obtain a mixed serum solution. The internal standard solution included 100 ug/ml of L-tyrosine-(phenyl-3,5-d2) (Sigma-Aldrich), 10 ug/ml of $^{13}$C-cholic acid (Cambridge Isotope Laboratories), and 60 ug/ml of doxercalciferol (MedChem Express). The mixed serum solution was vortexed for 4 min and centrifugated at 13,000 rpm (or 17,949 g) for 5 min. Then, 200 μl supernatants containing all metabolites of the mixed serum solution were transferred to another tube and dried by centrivap cold-trap centrifugation to obtain dried metabolite extracts. Lastly, the dried metabolite extracts were reconstituted with 75 μL of 55% methanol (Thermo Fisher) containing 0.1% of formic acid (Thermo Fisher) for further analysis.

Metabolite Extraction for Targeted Metabolomics Detection

For metabolite extraction in targeted metabolomics detection, the similar method described above was used except following modification. 6 μL of an internal standard solution including 5 μg/mL of $^{13}$C-cholic acid was added to 60 μL of serum along with 240 μL of acetonitrile and isopropanol (in ratio of 4:1, Thermo Fisher) and 60 μL of ammonium formate (0.5 g/ml) to obtain a mixed solution. The mixed solution was centrifugated at 13,000 rpm (17,949 g) for 5 min. Then, 80 μL of supernatants of the mixed solution was diluted with 200 μL water before use.

Preparation of QC Samples

Serums derived from each normal subject and each CRC subject in the discovery set were pooled respectively as a C-pool and a N-pool (total volume of 10 ml for each pooled sample). A serial of 7 additional quality control (QC) samples were prepared by mixing 10%, 20%, 30%, 40%, 50%, 75%, and 90% of the C-pool with N-pool by volume. The QC samples were used for semi-quantitively untargeted metabolomic profiling.

Untargeted Metabolite Profiling

Metabolites extracted from the discovery set in the serum cohort and the fecal-serum matched cohort were analyzed by a Q Exactive or a Q Exactive mass spectrometer, which was coupled to UltiMate3000 UPLC (ThermoFisher). Data were acquired over a mass/charge ratio (m/z) range of 130 to 1200 Da at a resolution of 70,0000 in a full MS-scan mode. The electrospray source conditions were set as follows: sheath gas, 40 psi; capillary temperature, 320° C.; spray voltage, 3 kV (positive HESI) and 3.2 kV (negative HESI). A CORTECS (Waters) C18 column (1.6 μm, 2.1*100 mm) was used with an oven temperature maintained at 35° C. A flow rate was set at 0.3 mL/min and 5 μL of each sample was injected. Mobile phase A (e.g., acetonitrile containing 0.1% of formic acid) was applied as a gradient (e.g., from 5% to 45% at 0.5-14 min, 75% at 32 min, 80% at 42 min, 100% at 50-55 min and back to 5% in next 5 mins). Mobile phase B was Merck Millipore water containing 0.1% of formic acid. The resulting mass spectra were exported into Progenesis QI Software (Nonlinear Dynamics, Durham, N.C., USA) for further processing.

Metabolite Annotation and Inferring

Metabolite annotation was performed with the following modifications. In brief, MS-DIAL 4.24 was applied for annotation. First, QC MS1/MS2 were spectrum searched against a public spectra library, including HMDB, MoNA, and MassBank. Then lipid blast was further performed by lipidomics function. Default similarity score cutoff was applied. Finally, a manual check with a reference database was performed for confirming and distinguishing similar readouts. For those metabolites whose MS/MS can't be reliably acquired under the current condition, their MZ were searched against HMDB and Bio-ML databases to infer their potential identities. The confidence level for metabolite annotation was set as: the MS/MS from referencing compounds in the current chromgrapy and MS condition>MS/MS from library>MZ matching.

Metagenome Sequencing and Taxonomic Profiling

Fecal samples of the 55 subjects involved in the matched cohort were used for DNA extraction by QIAamp DNA Stool Mini Kit (QIAGEN), among which 44 DNA samples passed the quality control. Whole-genome shotgun metagenome sequencing was used for taxonomy and function analysis of the gut microbiome. Libraries preparation and subsequent metagenomic sequencing were carried out on the HiSeq 4000 platform (Illumina) with 150 base pairs, pairedend reads at Shanghai OE Biotech Co. Ltd, targeting larger than 10 Gb of sequence per sample.

Raw sequencing data was processed using Trimmomatic V0.36, including adapter trimming, depleting low quality reads or base pairs, as well as removing host contaminations by mapping against the human genome (hg19) with Bowtie 2. Afterwards, clean reads were constructed and further taxonomically profiled using MetaPhlAn2 version 2.2.0 with default parameters. In total, 12445 microbiome species were profiled and among them, only 640 species with relative abundances more than 0.1% in at least 1 subject were considered for further microbiome-metabolome co-relation analysis.

Targeted Metabolite Profiling

The ExionLC AC system was connected to a 6500 QTrap Mass Spectrometer (Sciex) run in separate ion modes (positive and negative). The mobile phase and the column for reversed-phase liquid chromatographic were the same as those of the untargeted metabolite profiling. The injection volume of each sample was 10 µl. The dwell time for each transition was 10 ms with medium collison gas, the curtain gas was 40, the ion spray voltage was 5,000 V and −4,500V, and the source temperature was 450° C. Metabolites were eluted from the column at a flow rate of 0.3 mL/min with initial 12% of mobile phase B, followed by increasing to 60% of mobile phase B for 2.5 minutes. A linear 60%-85% and 85%-100% of mobile phase B were set at 6 min and 8.5 min, respectively. The quality control sample of targeted analysis was pooled as follows: control group (252 samples), cancer group (261 samples) and control group: cancer group (1:1). Declustering potentials and collision energies were optimized from the quality control sample of the control group. Metabolite peaks were integrated using Sciex Analyst 1.6.3 software.

Air-Flow Assisted Desorption Electrospray Ionization Mass Spectrometry Imaging (AFADESI-MSI) Analysis of CRC and Adjacent Normal Tissue For mass spectrometry imaging, a total of 9 pairs of human colorectal tissue samples including advanced adenoma or CRC and matched adjacent noncancerous tissue were collected. Those samples were freshly frozen with liquid nitrogen immediately after biopsy and then transferred to cryogenic vials and stored at −80° C. Sectioning at 10 µm was performed using a CM 1860 UV cryostat microtome (Leica). Adjacent sections were thaw-mounted onto microscope slides for conventional H-E staining and mass spectrometry imaging.

ADADESI-MSI analysis was performed using a Q-Exactive mass spectrometer (Thermo Scientific) within the range of 70 to 1,000 m/z at 70,000 mass resolution in both positive and negative ion mode. In brief, the ADAESI-MSI conditions were as follows. Spray solvent, a mixture of acetonitrile and water (8:2, volume ratio), was applied at a flow rate of 5 µL/min during ionization. The sprayer and transport tube voltages were set at 7,500 and 2,000 V respectively in the positive ion mode and at −5,500 and −1,500 V respectively in the negative ion mode. The extracting gas flow rate was 45 L/min, and the capillary temperature was 350° C. ADAESI-MSI scanning was set along the longer edge of microscope slide (X-axis of scanning) at a constant rate of 200 µm/s, and a 200-µm vertical step separated adjacent lines in the Y-axis. The scanning started at the upper left corner of the microscope slide and ended at the lower right corner of the microscope slide.

Data Analysis

Data preprocessing, statistical analysis, and predictive model building were conducted using The R (v3.6.1).

Metabolomic Data Preprocessing

Peak extraction and alignment were performed using Progenesis QI software. To acquire more reliable peaks, the retention time had 1 decimal place, m/z had the abundance of 3 decimal places to aggregate the metabolites. To filter out background signals, metabolites with abundances less than 5000, or with abundances equal to zero in more than 85% subjects were left out. To eliminate batch-to-batch differences, the R pre-process Core software package (v1.47.1) was used for robust multiarray averaging (RMA) normalization and the abundance ratios of metabolites were calculated.

Statistics

Using Anova with Tukey honestly significant difference (HSD) test, metabolites with p-values less than 0.005 were selected as significantly altered metabolites. Based on this result, metabolites with fold changes of colorectal abnormal subjects and normal subjects less than 1.2 and more than 0.8 were filtered. Metabolites with differences greater than 15% among batches were deleted.

Gut Microbiome-Serum Metabolome Correlation Analysis

Pairwise correlation coefficients using Pearson's correlation coefficients between gut microbiome species and serum metabolites were carried out on the 33 colorectal abnormal subjects in the matched cohort. The pairwise correlation coefficient and p value for each species-metabolite pair were calculated and considered significantly associated with the cut off of p value equal to or less than 1E-3.

Example 1

Figure 1B:
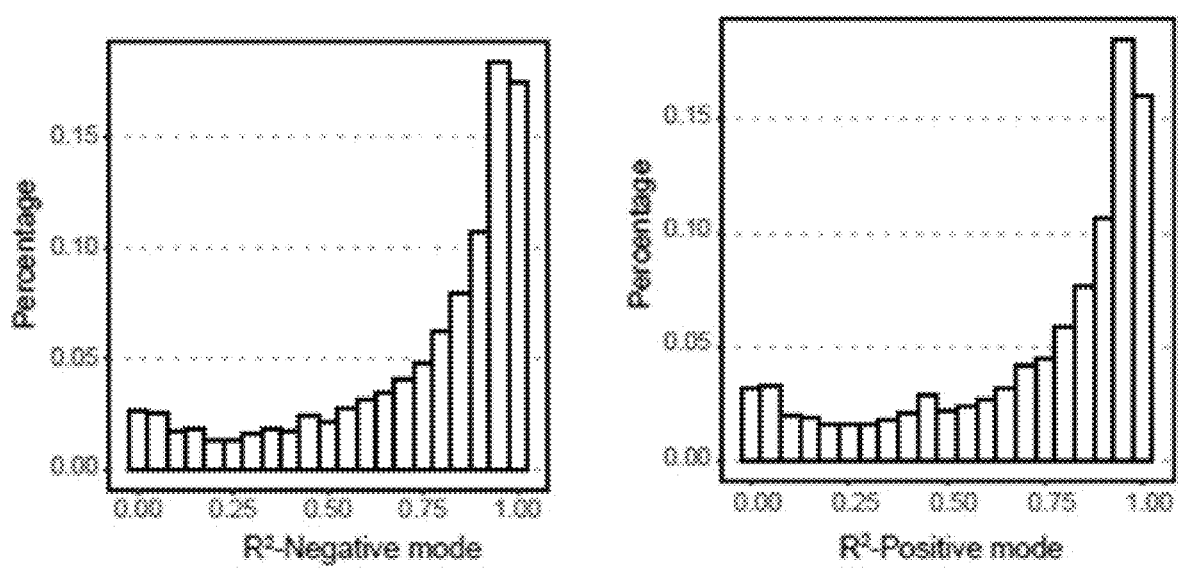
FIG. 1B is an analytical diagram illustrating a distribution diagram of $R^2$ values of untargeted LC-MS features in a negative ion mode and a positive ion mode according to some embodiments of the present disclosure.

Semi-Quantitative Untargeted Metabolomics Profiling in Serum from the Discovery Set Revealed Significantly Altered Metabolites in Both CRC and Adenoma Patients A relationship between the serum metabolome and colorectal adenoma or colorectal cancer was determined by performing untargeted metabolome profiles on the discovery set via LCMS. FIG. 1A is a schematic diagram illustrating an overview of experimental design and analysis procedures. As shown in FIG. 1A, the discovery set was divided into the normal group, the adenoma group, and the colorectal cancer group. Low abundance signals (e.g., mean abundance<5000 in all of the three groups) were filtered out at first. To further assess precision and linearity of the untargeted metabolomics data, a series of QC samples was run by mixing 10%, 20%, 30%, 40%, 50%, and 75% of C-pool with N-pool by volume as described above. The accuracy of 13666 metabolites in the negative ion mode and 14758 metabolites in the positive ion mode, whose normalized relative abundances were above background blank cut-off, was estimated by comparing their mixing ratios derived from measured abundances with the expected mixing ratios between the C-pool and the N-pool. FIG. 1B is an analytical diagram illustrating a distribution diagram of $R^2$ values of untargeted LC-MS features in a negative ion mode and a positive ion mode. $R^2$ values of the linear regression model between the expected mixing ratio and measured mixing ratio for each metabolite detected in either negative and positive ion modes were displayed in FIG. 1B, respectively. As shown in FIG. 1B, $R^2$ values for more than 50% metabolites were larger than 0.9 in both negative and positive ion modes, indicating that the majority of metabolites can be measured with significant accuracy, and the relative abundances of these metabolites show robust linearity when ranging within 10% and 100% of difference between the pooled normal and CRC cancer group.

Figure 1C:
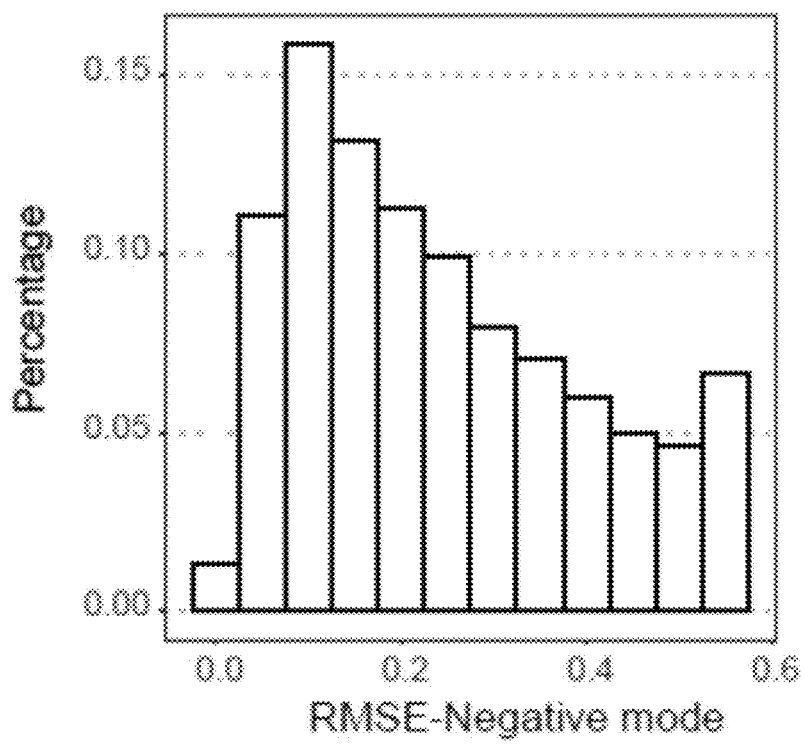
FIG. 1C is an analytical diagram illustrating distribution of the root mean squared error (RMSE) values for metabolite features in a negative ion mode according to some embodiments of the present disclosure.
Figure 1D:
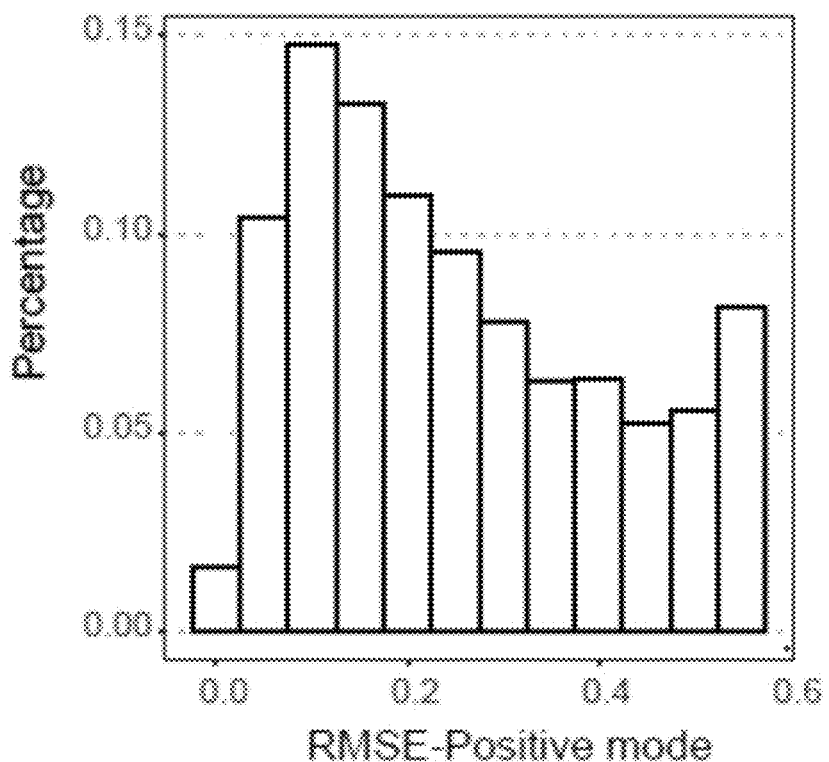
FIG. 1D is an analytical diagram illustrating distribution of the root mean squared error (RMSE) values for metabolite features in a positive ion mode according to some embodiments of the present disclosure.

FIG. 1C is an analytical diagram illustrating distribution of the root mean squared error (RMSE) values for metabolite features in a negative ion mode. FIG. 1D is an analytical diagram illustrating distribution of the root mean squared error (RMSE) values for metabolite features in a positive ion mode. The precision of above metabolite profiling was evaluated by the root mean squared error (RMSE) of their linear regression model. The distribution of RMSE values for all the metabolite features shows that more than 50% of metabolites with RMSE less than 0.2 for both negative and positive ion modes (see FIGS. 1C-1D). In conclusion, the metabolite profiling can be precisely and repeatedly measured in a semi-quantitative manner with significant accuracy.

Figure 1E:
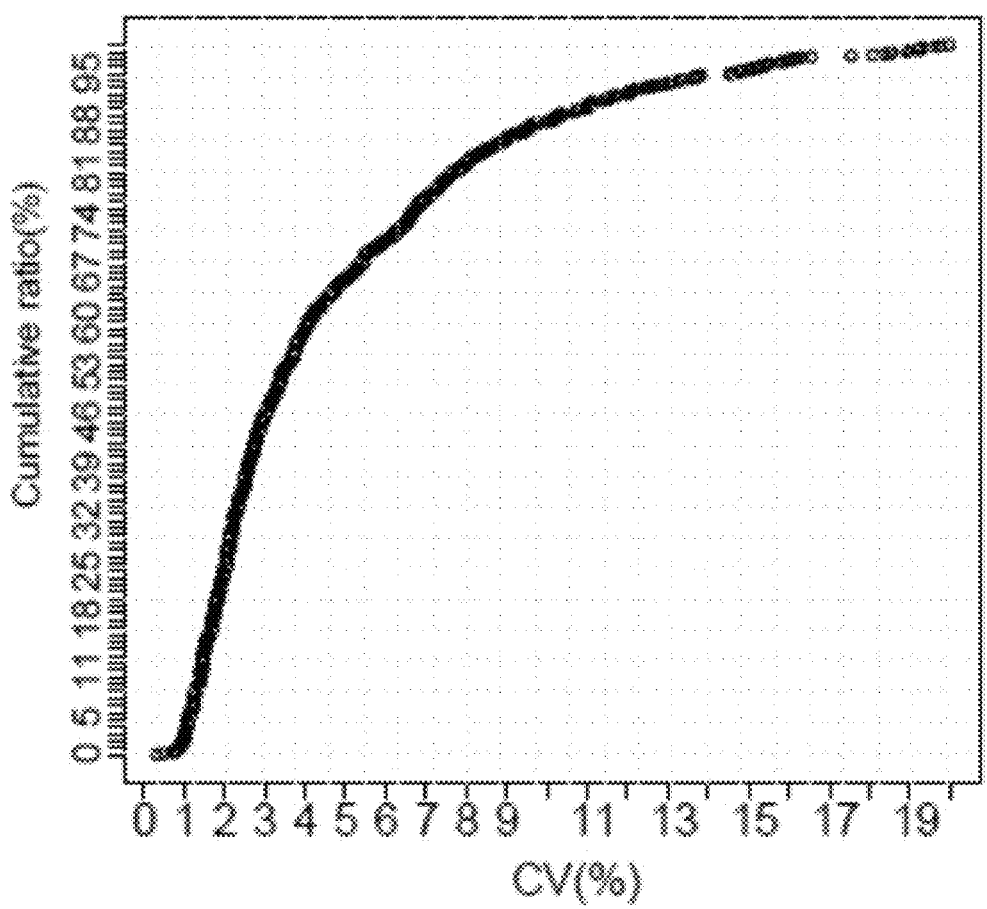
FIG. 1E is an analytical diagram illustrating a distribution diagram of coefficient of variance (CV %) of untargeted LC-MS features in all pooled CRC samples according to some embodiments of the present disclosure.

FIG. 1E is an analytical diagram illustrating a distribution diagram of coefficient of variance (CV %) of untargeted LC-MS features in all pooled CRC samples. Using pooled CRC samples as quality control, coefficient of variance (CV %) was determined for all metabolite features, revealing that CV % for more than 90% of these features were less than 15% (FIG. 1E), suggesting stability between different detection batches.

Figure 1F:
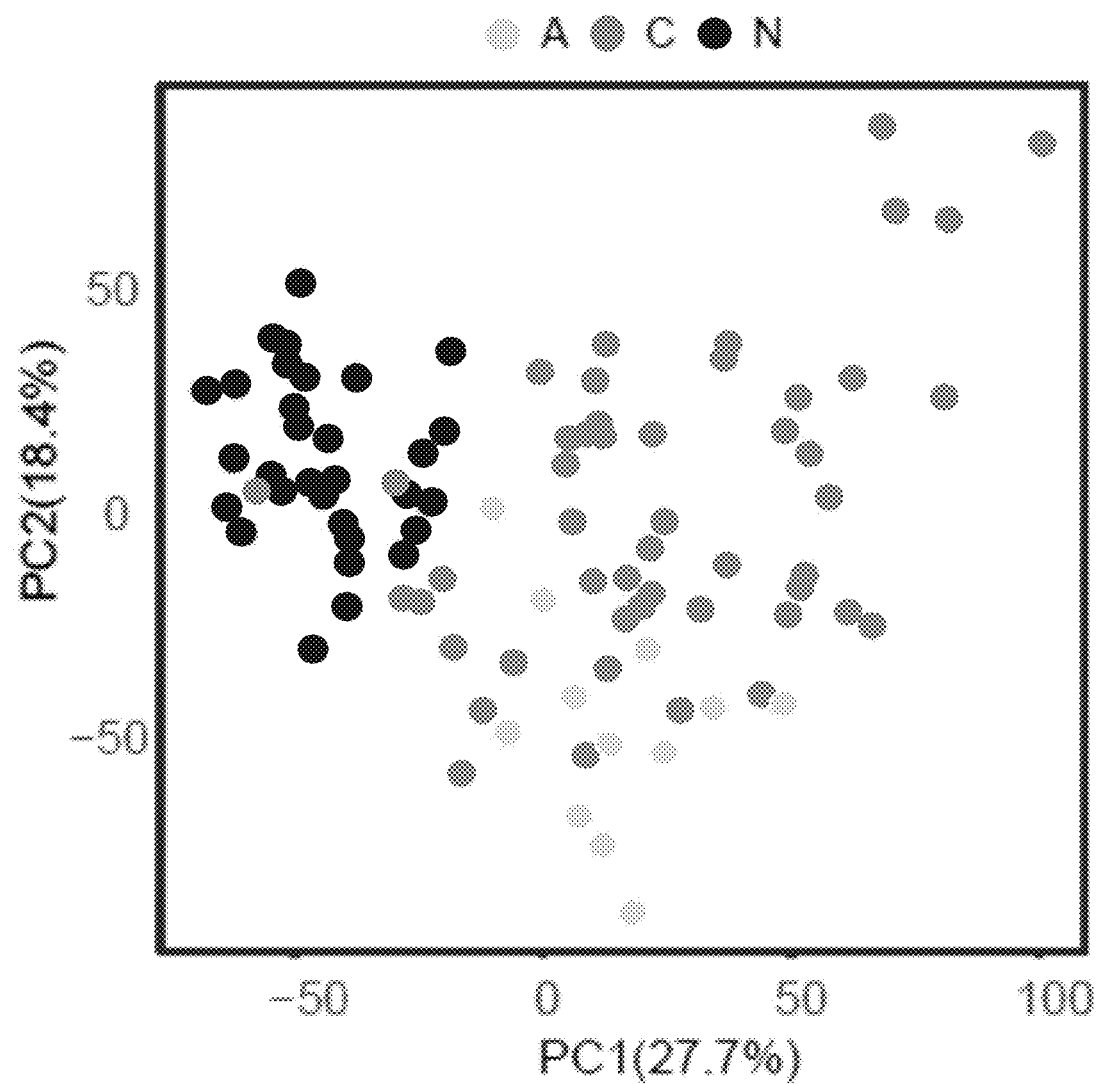
FIG. 1F is a principal component analysis (PCA) plot of the metabolites of all samples according to some embodiments of the present disclosure.
Figure 1G:
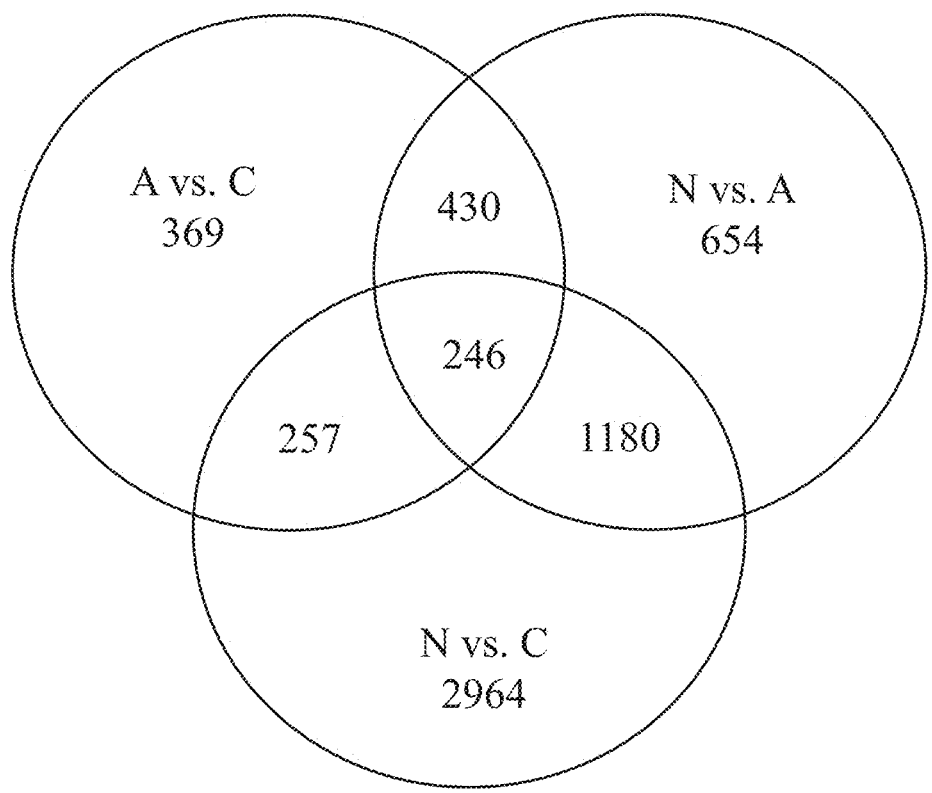
FIG. 1G is a comparison diagram of a count of significantly altered metabolites in normal group, the adenoma group, and the colorectal cancer group according to some embodiments of the present disclosure.
Figure 1H:
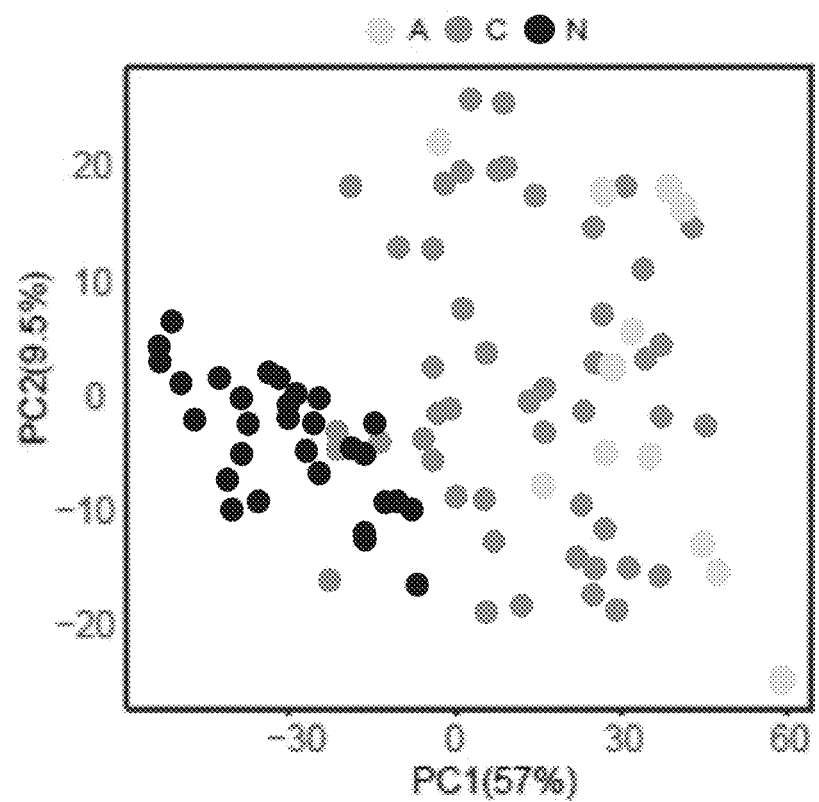
FIG. 1H is a PCA plot illustrating discriminations of serum metabolomic states of samples from normal subjects (N, blue), adenomas subjects (A, red) and colorectal cancer subjects (C, green) based on metabolites that showed significant alternation in both adenomas and colorectal cancer subjects compared to normal subjects according to some embodiments of the present disclosure.

Metabolites showed significantly different abundances between either pair of groups (p value<0.005, fold change >1.2 or <0.8). FIG. 1F is a principal component analysis (PCA) plot of the metabolites of all samples. As seen from FIG. 1F, the distribution of the adenoma group and the distribution of colorectal cancer group were similar, while the normal group could be clearly distinguished from these two groups. FIG. 1G is a comparison diagram of a count of significantly altered metabolites in normal group, the adenoma group, and the colorectal cancer group. As seen from FIG. 1G, N vs. C showed the greatest similarity with N vs. A, indicating that tumorigenesis had already induced significant serum metabolic changes in the adenoma stage. These metabolites that significantly altered both in the C vs. N group and the A vs. N group, termed as colorectal abnormal related metabolites, were used for further analysis since they exhibited both early and sustained alternations during tumor progression that favors early and consistent detection for both adenomas and colorectal cancer patients. In total, 1426 metabolite features were included. FIG. 1H is a PCA plot illustrating discriminations of serum metabolomic states of samples from normal subjects (N, blue), adenomas subjects (A, red), and colorectal cancer subjects (C, green) based on metabolites that showed significant alternation in both adenomas and colorectal cancer subjects compared to normal subjects. Similarly, based on these metabolites, a clear division between normal subjects and colorectal abnormal subjects (C&A) could also be achieved (see FIG. 1H).

Example 2

Figure 2A:
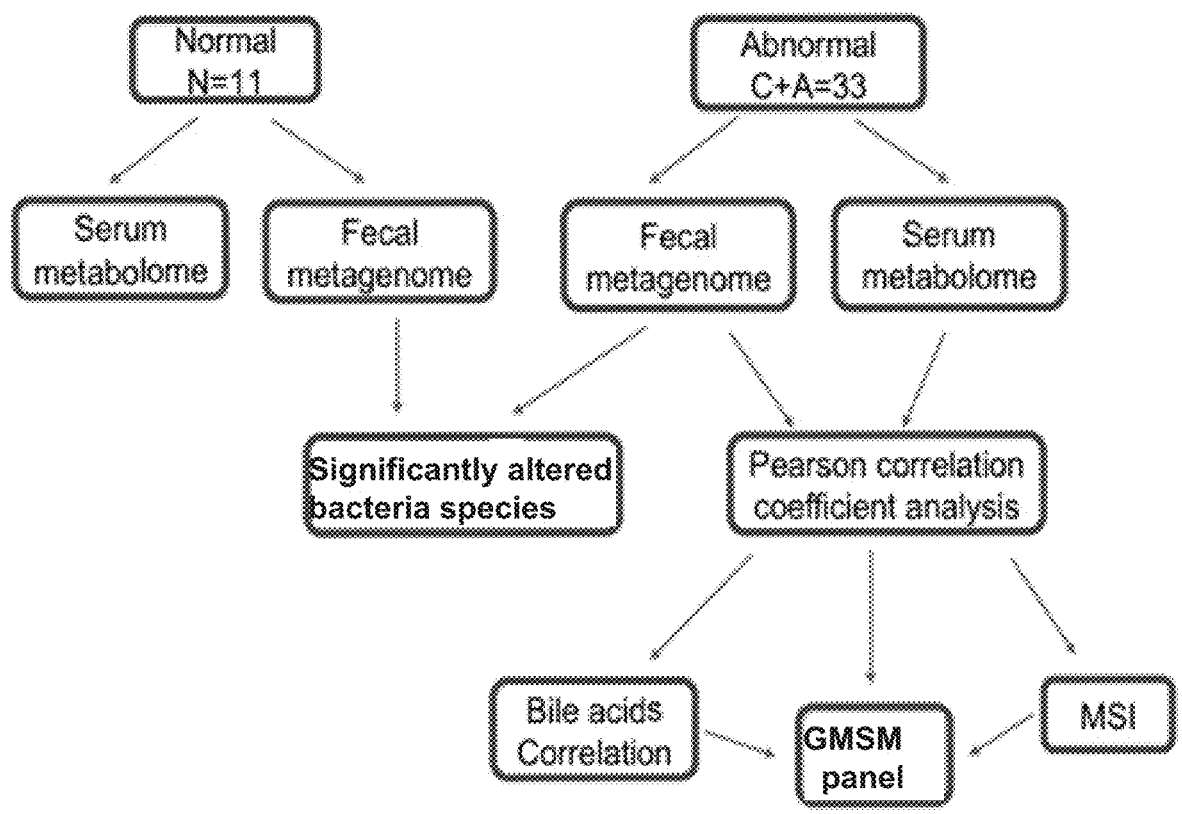
FIG. 2A is an analytical diagram illustrating the procedure of integrated analysis of fecal metagenome and serum metabolome in the matched cohort according to some embodiments of the present disclosure.
Figure 2B:
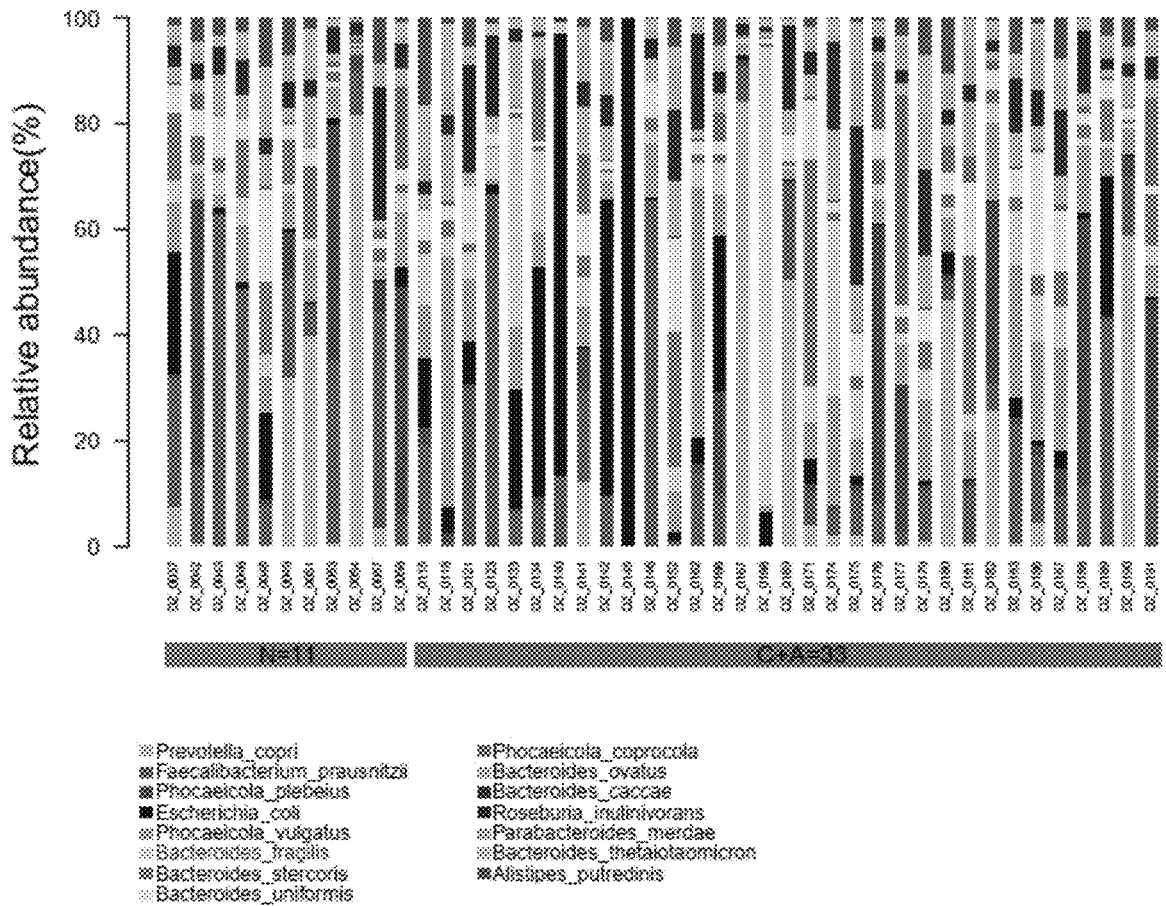
FIG. 2B is a bar chart showing 15 OUTs in each individual at species level according to some embodiments of the present disclosure.
Figure 2C:
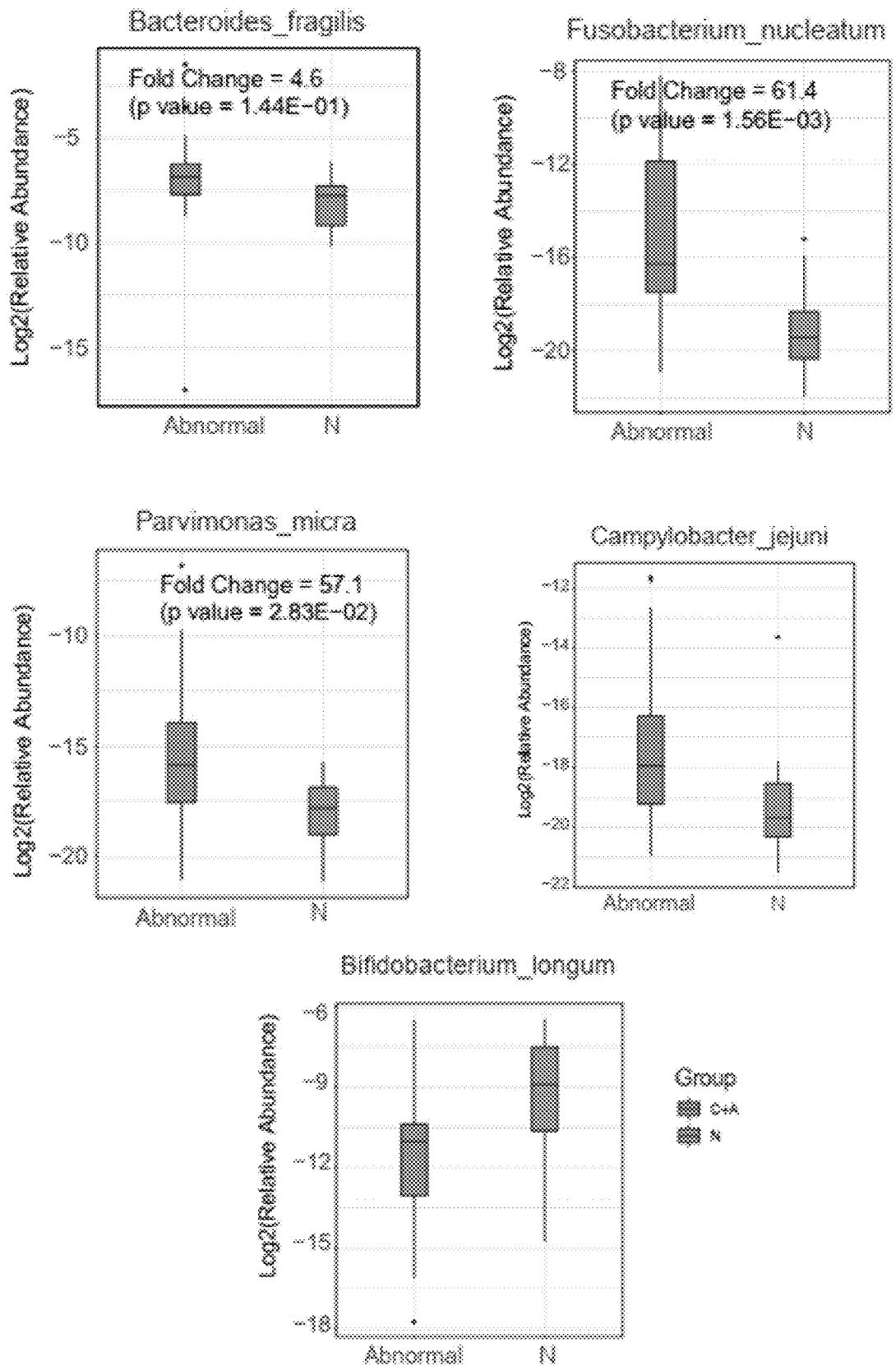
FIG. 2C is an analytical diagram illustrating relative abundances of several CRC associated gut microbiome species in normal and colorectal abnormal patients of the matched cohort according to some embodiments of the present disclosure.

Determination of Gut Microbiome Associated Serum Metabolites that are Significantly Altered in Colorectal Abnormal Patients FIG. 2A is an analytical diagram illustrating the procedure of integrated analysis of fecal metagenome and serum metabolome in the matched cohort. In total, data from 44 subjects (11 normal and 33 colorectal abnormal) in the matched cohort passed quality control. Taxonomic profiling of the metagenome data revealed 12455 microbiome species. FIG. 2B is a bar chart showing 15 OUTs in each individual at species level. Among the top 15 most abundant species, the elevation of the enterotoxigenic Bacteroides fragilis (ETBF) was observed, which has been proposed to be a keystone pathogen in CRC initiation. FIG. 2C is an analytical diagram illustrating relative abundances of several CRC associated gut microbiome species in normal and colorectal abnormal patients of the matched cohort. As shown in FIG. 2C, abundances of several other CRC promoting species, including *Fusobacterium nucleatum, Parvimonas micra*, and *Campylobacter jejuni* were all significantly upregulated in CRC patients, while probiotics like *Bifidobacterium longum* were downregulated. These results were well consistent with previous reports, further supporting the quality of the metagenome sequencing data.

Figure 2D:
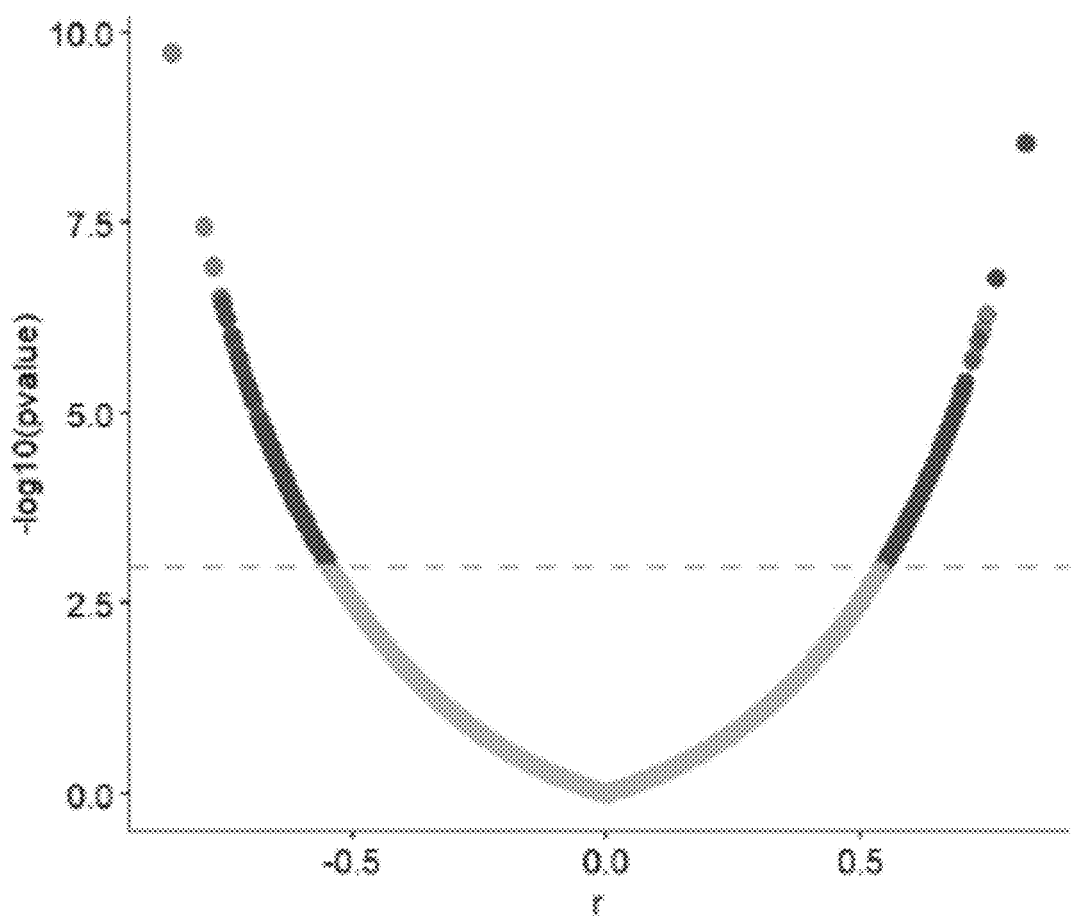
FIG. 2D is a co-relation map between gut microbiome and serum metabolites in colorectal abnormal subjects according to some embodiments of the present disclosure.
Figure 2E:
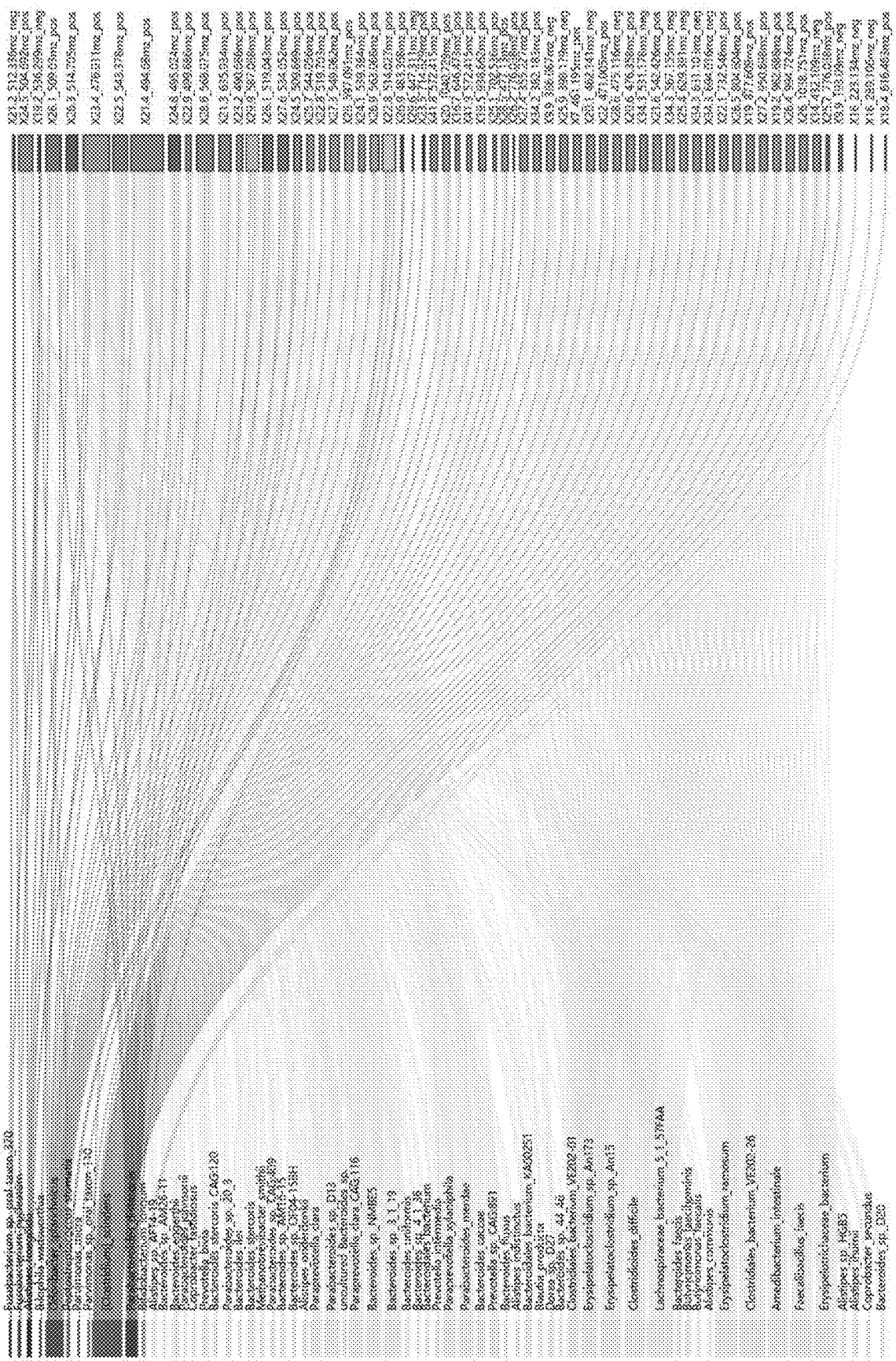
FIG. 2E is a Sankey diagram showing covariations between CRC associated gut microbes and their co-related serum metabolites according to some embodiments of the present disclosure.

Pearson correlation coefficient analysis was performed on the 33 colorectal abnormal subjects in the matched cohort to determine microbiome associated serum metabolites, using microbiome species with relative abundance higher than 0.1% in at least one subject and metabolites with abundance higher than 5000. FIG. 2D is a co-relation map between gut microbiome and serum metabolites in colorectal abnormal subjects. The cut-off of significant correlation was set at p-value of 1E-3, while a false discovery rate (FDR) at this point was 18% in FIG. 2D. Among the co-related species-metabolite pairs, 322 metabolite features within the 1426 previously described colorectal abnormal related metabolites exhibited significant associations with the gut microbiome. FIG. 2E is a Sankey diagram showing covariations between CRC associated gut microbes and their co-related serum metabolites. Associations with species that has been previously reported to be tumor-promoting in colorectal cancer, associations with antitumoral species, and associations of these metabolites with other bacteria species were shown in FIG. 2E. The gut microbiome included a series of bacteria species that have been reported to associate with CRC initiation and progression, such as CRC promoting *Fusobacterium nucleatum, Parvimonas micra, Alistipes finegoldii*, and *Odoribacter splanchnicus* as well as probiotics *Bifidobacterium longum* and *Parabacteroides distasonis*. By assessing the potential contributions of microbiome associated metabolites in predicting colorectal abnormality, it is observed that only by using the 63 metabolites associated with CRC related microbiome species could explain 87% of the total variance (mean out-of-sample $R^2=0.87$) between normal and colorectal abnormal metabolomes in the discovery cohort, while the total 1426 colorectal abnormality co-related metabolites explained 93% of the total variance (mean out-of-sample $R^2=0.93$). These observations strongly suggest that CRC related microbiome species could leads to alternations of serum metabolites, and the 63 gut microbiome-associated serum metabolites contributed significantly to detection of colorectal abnormality in the discovery cohort. Moreover, in addition to the previous characterized CRC related species, these metabolites also exhibited close associations with a huge number of other species with unknown associations with colorectal abnormality. Some of these species also showed significantly altered abundances between normal and colorectal abnormal subjects, such as *Bacteroifrd fluxus*, Dore asp. D27, *Bacteroidales bacterium* KA00251.

Example 3

Prediction of Colorectal Abnormality in the Discovery Cohort by a Panel Based on Gut Microbiome-Associated Serum Metabolites Based on these gut microbiome-associated serum metabolites described above, a LASSO algorithm was performed to seek for key metabolite biomarkers for colorectal abnormality. The LASSO algorithm with 10-fold cross validation (CV) was used for feature selection from serum metabolomics data and gut microbiome metabolomics which were determined previously. 322 metabolite features, which are significantly altered between the normal and the CRC or adenoma samples (adj p<5E-3), exhibited significant correlations with gut-microbiome (p<1E-3, FDR≤18%). Using panel voting approach, 32 metabolite features have been involved in more than 75% of the 200 times of LASSO run. Their chemical structure annotation, including MS2 ion pairs, if identifiable, was established by MS/MS spectrum matching as described previously. 8 metabolite features among 32 metabolite features are listed in Table 1, as described above. These 8 metabolites could be detected and showed consistent variances by MRM based targeted LC-MS detection using the same group of subjects with the discovery cohort, indicating that these metabolites could be stably measured using different approaches (See Table 6). The chemical characteristics of the 8 inferred metabolites were first evaluated by targeted LC-MS with the same sample set as from which the corresponding features were initially uncovered by the un-targeted LC-MS. 23 other metabolite features among the 32 metabolite features are listed in Table 3, as described above. These metabolites were also shown to be associated with gut microbiomes and demonstrated a significant correlation with CRC/CRA abnormality in the sample.

TABLE 6

Serum abundances and variances in untargeted and targeted metabolomics analysis

| Metabolites | Untargeted | | | | Targeted | | | |
|---|---|---|---|---|---|---|---|---|
| | feature | Fold change | p-value | C Pooled-CV(%) | feature | Fold change | p-value | C Pooled-CV(%) |
| 9,12,13-TriHOME (10) | X13_329.233mz_neg | 1.97 | 3.64E−07 | 2.17 | 331.240/285.222-2 | 1.19 | 9.16E−02 | 2.81 |
| 9,12,18-TriHOME (12Z) | X14.3_329.233mz_neg | 0.27 | 4.35E−10 | 2.73 | 331.240/285.222-4 | 0.51 | 2.49E−09 | 4.51 |
| Culinariside | X16.8_420.807mz_pos | 0.68 | 4.35E−10 | 1.66 | 420.807/376.259 | 0.87 | 4.24E−01 | 7.89 |
| [(6-{[5,7-dihydroxy-2-(4-oxocyclohexa-2,5-dien-1-ylidene)-2H-chromen-3-yl]oxy}-3,4,5-trihydroxyoxan-2-yl)methyl][1-hydroxy-3-(4-hydroxyphenyl)prop-2-en-1-ylidene]oxidanium | X16.9_637.157mz_neg | 0.54 | 4.36E−10 | 2.64 | 637.157/253.072 | 0.80 | 4.42E−03 | 5.65 |
| 2-Octenoylcarnitine | X26.2_398.18mz_neg | 9.18 | 4.35E−10 | 0.84 | 398.180/150.002 | 10.83 | 1.67E−07 | 1.55 |
| (E)-2-(4,8-dimethylnona-3,7-dien-1-yl)-5-hydroxy-2,7-dimethyl-2H-chromene-8-carbaldehyde | X27.8_353.212mz_neg | 4.79 | 4.35E−10 | 2.06 | 353.212/177.092 | 3.34 | 4.37E−10 | 3.17 |
| N,O-Bis-(trimethylsilyl)phenylalanine | X28.5_368.169mz_neg | 6.85 | 4.35E−10 | 1.07 | 368.169/150.002 | 8.02 | 4.39E−10 | 4.65 |
| 14-HDoHE | X24_355.228mz_neg | 2.84 | 4.56E−08 | 5.65 | 355.228/163.113 | 2.98 | 9.86E−10 | 9.87 |

The predictive efficiency of the 8 metabolites were evaluated in the discovery group. FIG. 3A is a ROC for a prediction model utilizing the abundance of the 8 metabolites listed in Table 1 according to a validation set. Based on abundances detected by untargeted metabolome, normal subjects and colorectal unhealthy patients in the discovery cohort could be efficiently discriminated, reaching to an AUC of 0.95 (95% CI: 0.85-1.00), with a sensitivity of 97.8% (95% CI: 90.7%-100%) and a specificity of 91% (95% CI: 72.8-100%) (as shown in FIG. 3A).

Figure 3B:
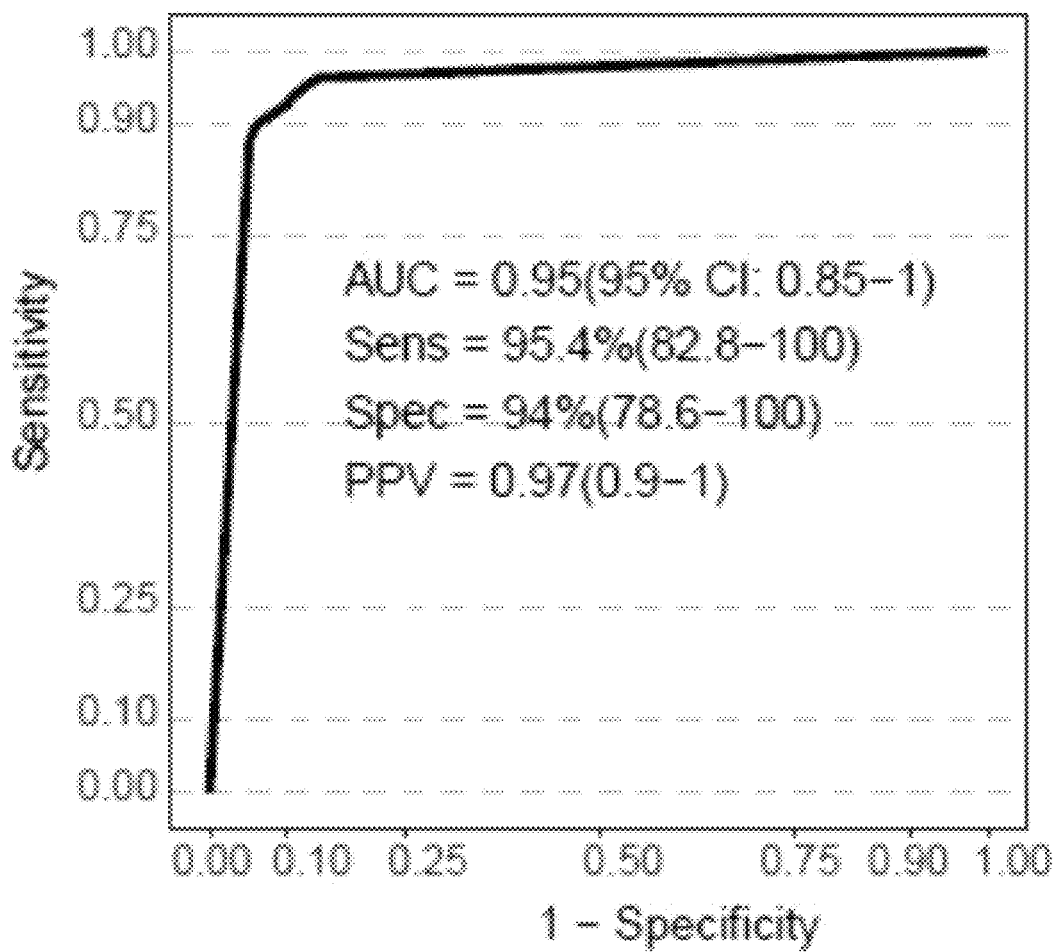
FIG. 3B is an analytical diagram illustrating a ROC for the 8 metabolites based on targeted metabolome according to some embodiments of the present disclosure.

The stability of predictive efficiency of these 8 metabolites was determined by using targeted metabolomics of the same subject set. All these 8 metabolites exhibited consistent up or down-regulation trend in both untargeted and targeted detection. FIG. 3B is an analytical diagram illustrating a ROC for the 8 metabolites based on targeted metabolome. Moreover, as seen from FIG. 3B, these metabolites by targeted metabolomics detection could also achieve an AUC of 0.95 (95% CI: 0.85-1.00), and the sensitivity and specificity was 95.4% (95% CI: 82.8-100%) and 94% (95% CI: 78.6-100%), respectively. The AUC of the ROC for the same sample set from the untargeted LC-MS is 0.95, the AUC of the ROC from the targeted LC-MS also reached this value, suggesting that the metabolites can stably distinguish normal subjects from CRC or adenoma subjects as the original features with corresponding rt/mz.

Figure 3C:
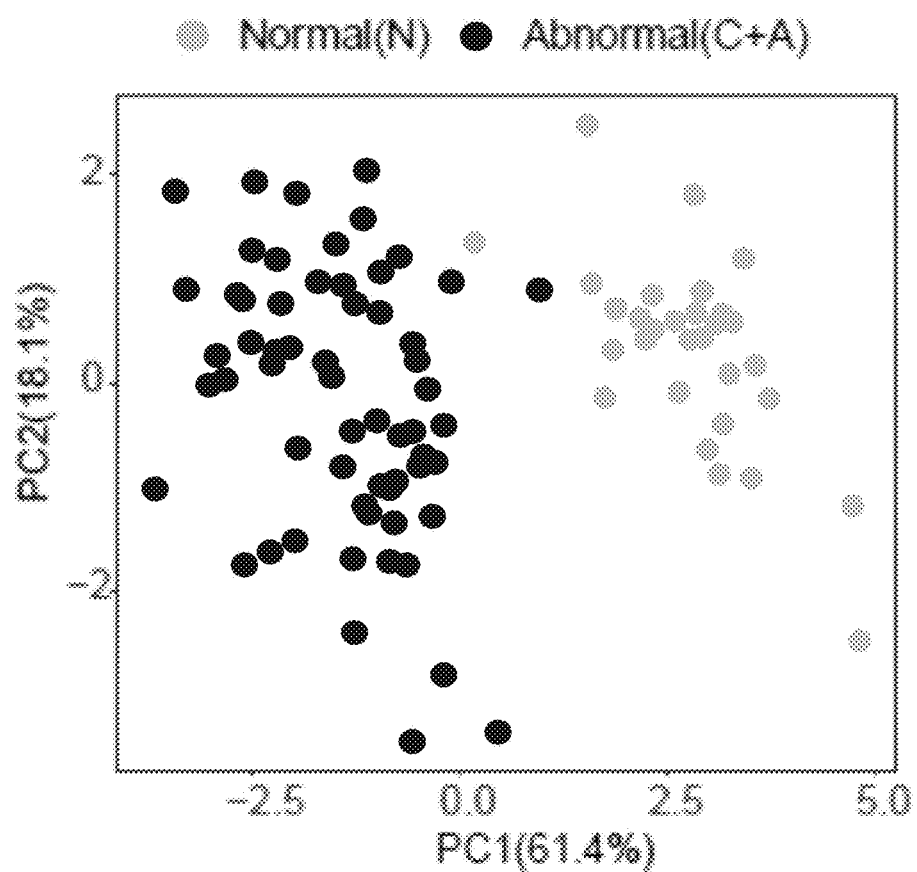
FIG. 3C is a PCA plot for the normal and colorectal unhealthy patients using untargeted metabolome analysis according to some embodiments of the present disclosure.
Figure 3D:
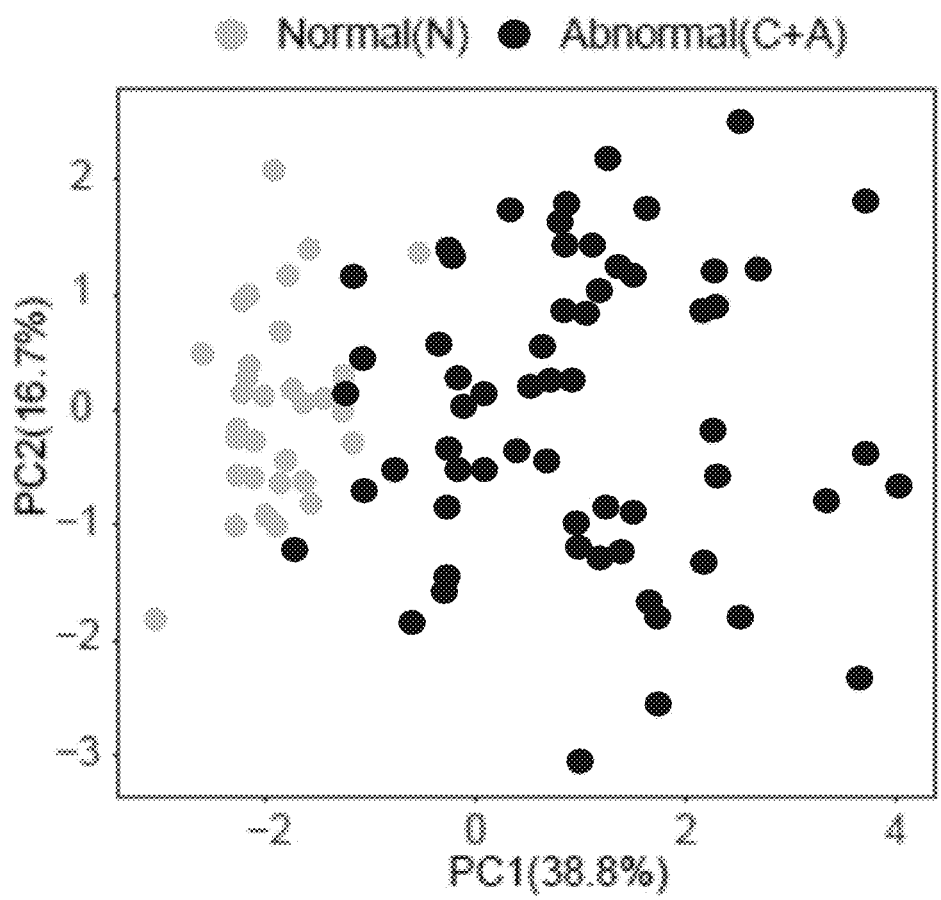
FIG. 3D illustrates a PCA plot for the normal and colorectal unhealthy patients using targeted metabolome analysis according to some embodiments of the present disclosure.
Figure 3E:
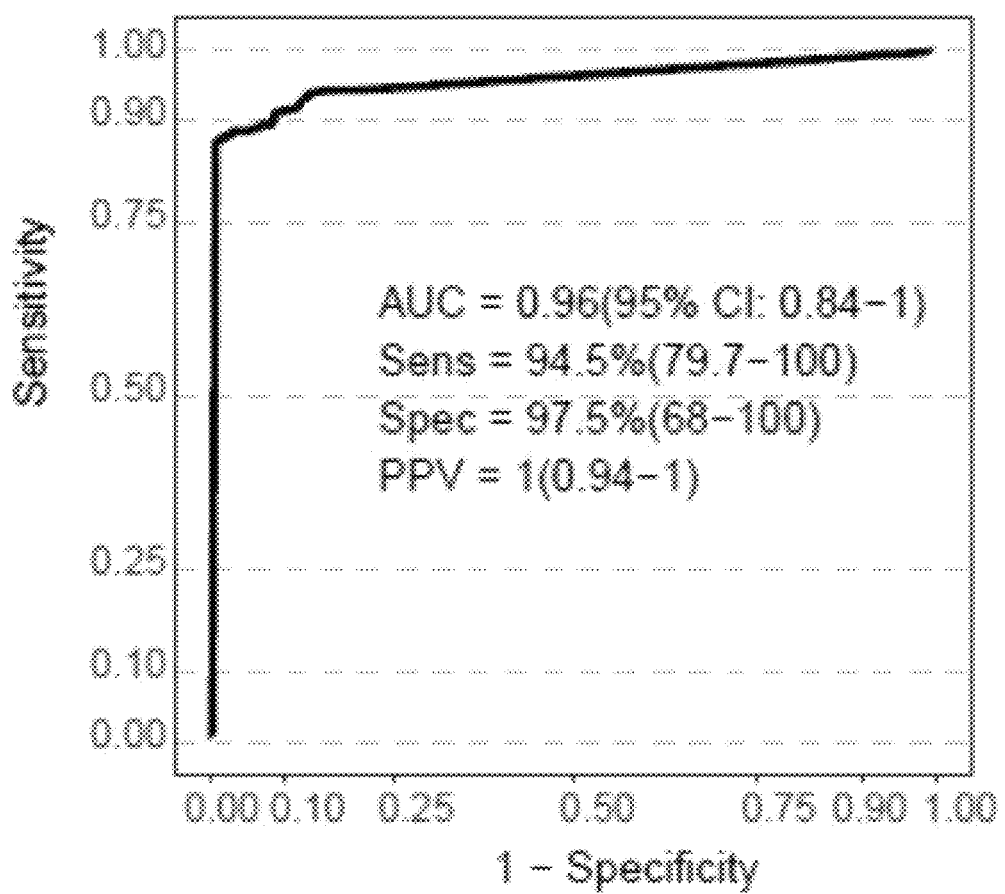
FIG. 3E is an analytical diagram illustrating a ROC curve of the CRC gut microbiome-associated serum metabolites (GMSM) panel for discrimination of normal and colorectal abnormal groups based on untargeted metabolomics analysis in matched cohort.
Figure 3F:
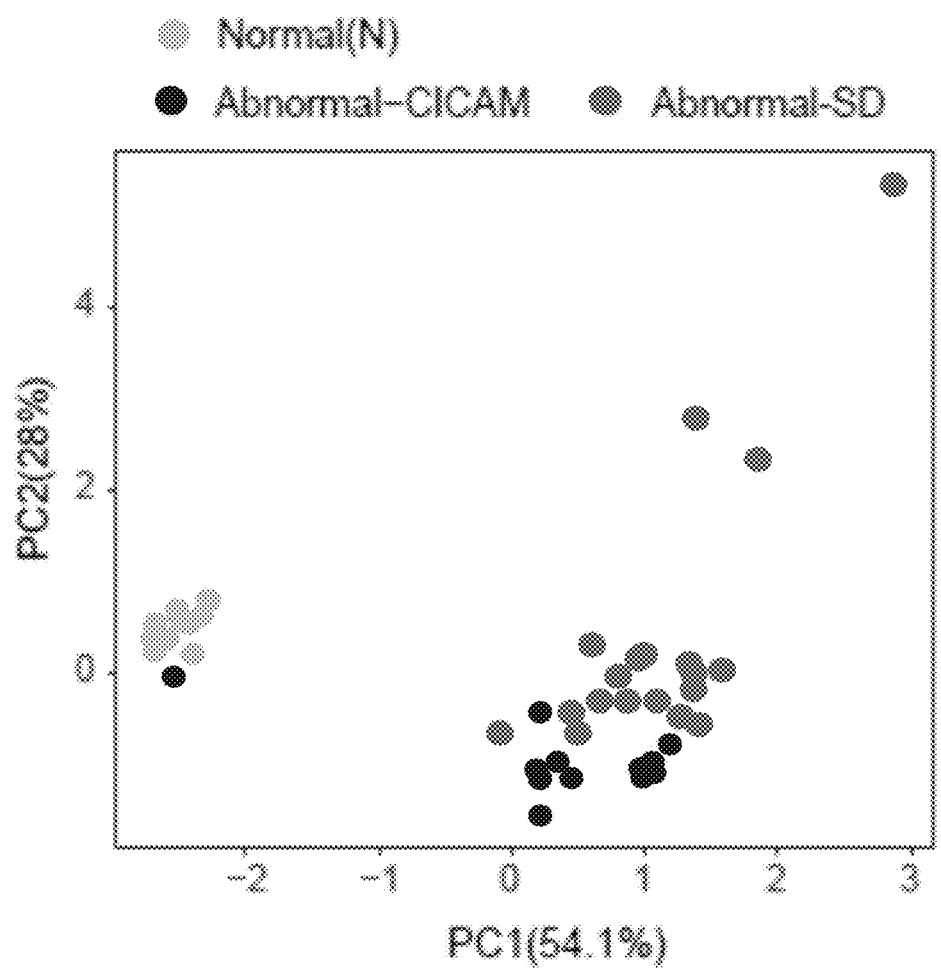
FIG. 3F is a PCA plot for the normal and colorectal unhealthy patients from CICAM and SD using metabolome analysis.

FIG. 3C is a PCA plot for the normal and colorectal unhealthy patients using untargeted metabolome analysis. FIG. 3D illustrates a PCA plot for the normal and colorectal unhealthy patients using targeted metabolome analysis. Using a PCA plot, normal and colorectal unhealthy patients by these metabolites can be separated clearly using both untargeted and targeted metabolome analysis (see FIG. 3C, D). FIG. 3E is an analytical diagram illustrating a ROC curve of the CRC GMSM panel for discrimination of normal and colorectal abnormal groups based on untargeted metabolomics analysis in the matched cohort. FIG. 3F is a PCA plot for the normal and colorectal unhealthy patients from CICAM and SD using metabolome analysis. Colorectal abnormal patients from two centers, CICAM and SD, were clustered together in the PCA plot, and both of them were clearly separated from normal subjects derived from CICAM. Additionally, in the independent feces-serum matched cohort, these metabolites also showed high diagnostic efficiency, with an AUC of 0.93 (95% CI: 0.76-1.00), and the sensitivity and specificity were 91.9% (95% CI: 77.7-100%) and 96.3% (95% CI: 60.3-100%), respectively. Thus, a panel including 8 gut microbiome associated serum metabolites (shown in Table 1, Table 2, and Table 6), also referred to as CRC GMSM panel, that could faithfully predict colorectal unhealthy patients. In addition, in the independent feces-serum matched cohort, a number of other metabolites also showed high diagnostic efficiency. 51 of these metabolites are listed in Table 4, as described above.

Example 4

Prediction Model Based on GMSM Panel Showing Diagnostic Value for Adenomas and CRC Patients in the Validation Cohort Based on this metabolites panel discovered in the discovery cohort, a prediction model was constructed using a modeling group, and its efficiency in colorectal abnormality was examined in an independent validation group. In total, 284 subjects obtained from CICAM were recruited in the modeling cohort, including 103 normal and 181 unhealthy patients, and targeted MRM method was used to measure relative abundances of the 8 GMSM metabolites. FIG. 4A is an analytical diagram illustrating a ROC curve showing discriminate efficiencies of GMSM panel in the modeling group. The prediction model was generated using a logic regression method and reached an AUC of 0.94 (95% CI: 0.90-0.99) in the testing set of the modeling group (see FIG. 4A). FIG. 4B is an analytical diagram illustrating CRC and adenomas biomarker signature scores of normal and colorectal abnormal subjects in modeling group. By plotting biomarker scores for normal and colorectal unhealthy subjects, significantly higher scores had been found in the adenomas and CRC group (see FIG. 4B). As shown in FIG. 4B, a cut-off value for the adenomas and CRC group was 0.825, and a cut-off value for the normal group was 0.375. To achieve the highest accuracy in the modeling group, the cut-off of the biomarker score was set at 0.541, leading to a sensitivity of 92.3% and a specificity of 87.4%.

Figure 4D:
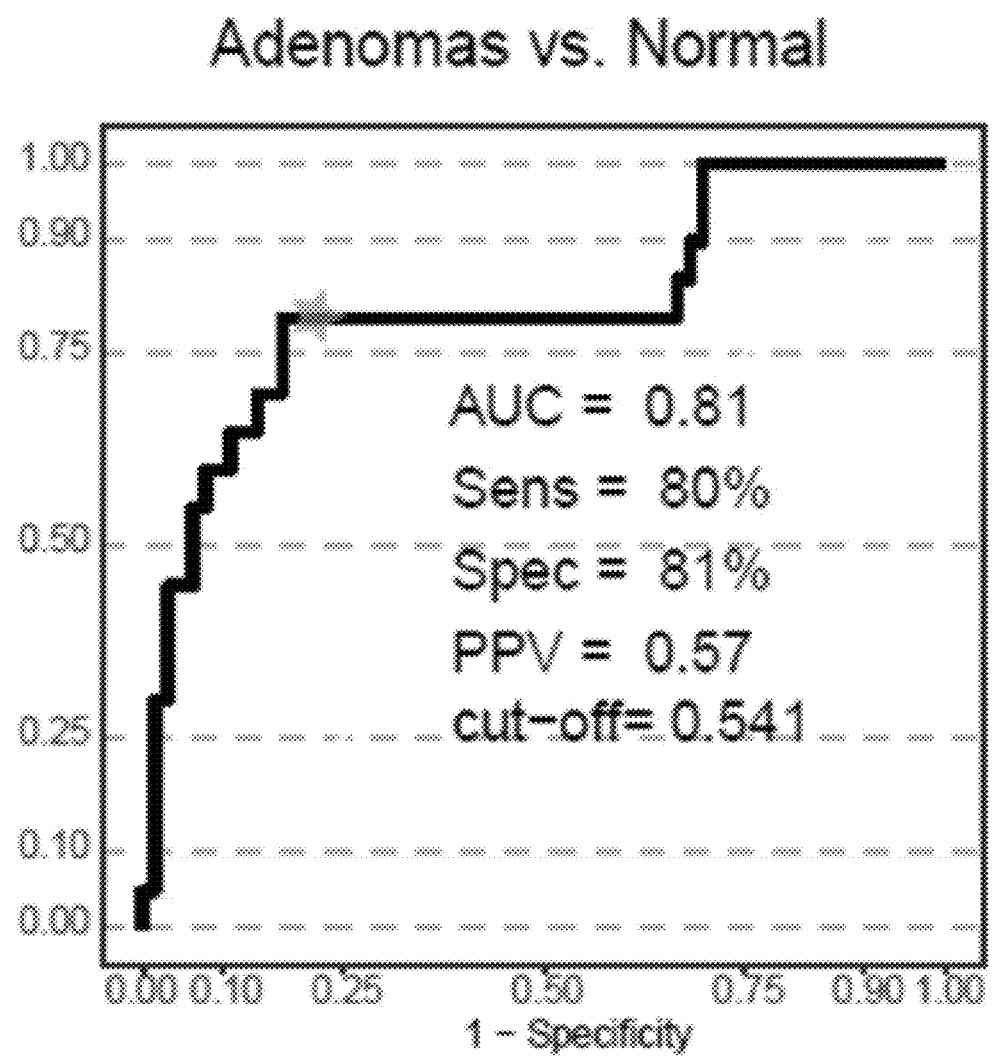
FIG. 4D illustrates ROC curves showing discriminate efficiencies of the CRC GMSM panel in validation group for adenomas patients and normal subjects according to some embodiments of the present disclosure.

Next, a diagnostic performance of the Prediction model was evaluated in an independent validation group, consisting 107 colorectal unhealthy patients and 63 normal subjects obtained from two separate sources, CICAM and ASCH (see, e.g., Table 7). FIG. 4C illustrates a ROC curve showing discriminate efficiencies of the prediction model in the validation group under the cut-off score of 0.541. By directly transferring the cut-off value derived from the modeling group, the GMSM prediction model reached an AUC of 0.91, with a sensitivity of 87.9% and a specificity of 81% in this validation set (see FIG. 4C). FIG. 4D illustrates ROC curves showing discriminate efficiencies of the CRC GMSM panel in the validation group for adenomas patients and normal subjects. Specific stage performances of this model were examined separately according to progression of colorectal abnormality from adenoma to late-stage cancer of colorectal unhealthy patients in the validation group, including adenomas, early/mid-stage (stage I/II), as well as late stage (stage III/IV) CRC patients. The results showed that the model distinguished normal with adenomas patients with an AUC of 0. 81, and a sensitivity of 80.0%. For early/mid-stage (stage I/II) patients, the AUC was 0.91, and a sensitivity of 88.2% while for late stage (stage III/IV) CRC patients, the sensitivity reached to 85% and its AUC was 0.91 (see FIG. 4D and table). These results indicate that the Prediction model exhibited promising efficiently in distinguishing normal subjects from those with colorectal adenoma and CRC, from as early as the pre-cancer stage through to late-stage surgically dissectible CRC patients.

TABLE 7

Performances for the biomarker panel in the testing and validation set (total and different stages, transferred cut-off 0.541)

| | | Validation set | | | |
|---|---|---|---|---|---|
| | Testing set | total | Adenomas | Stage I/II CRC | Stage III/IV CRC |
| Sensitivity | 92.3% | 87.9% | 80.0% | 88.2% | 85% |
| Specificity | 87.4% | 81.0% | 81.0% | 81.0% | 81.0% |

Example 5

Figure 5A:
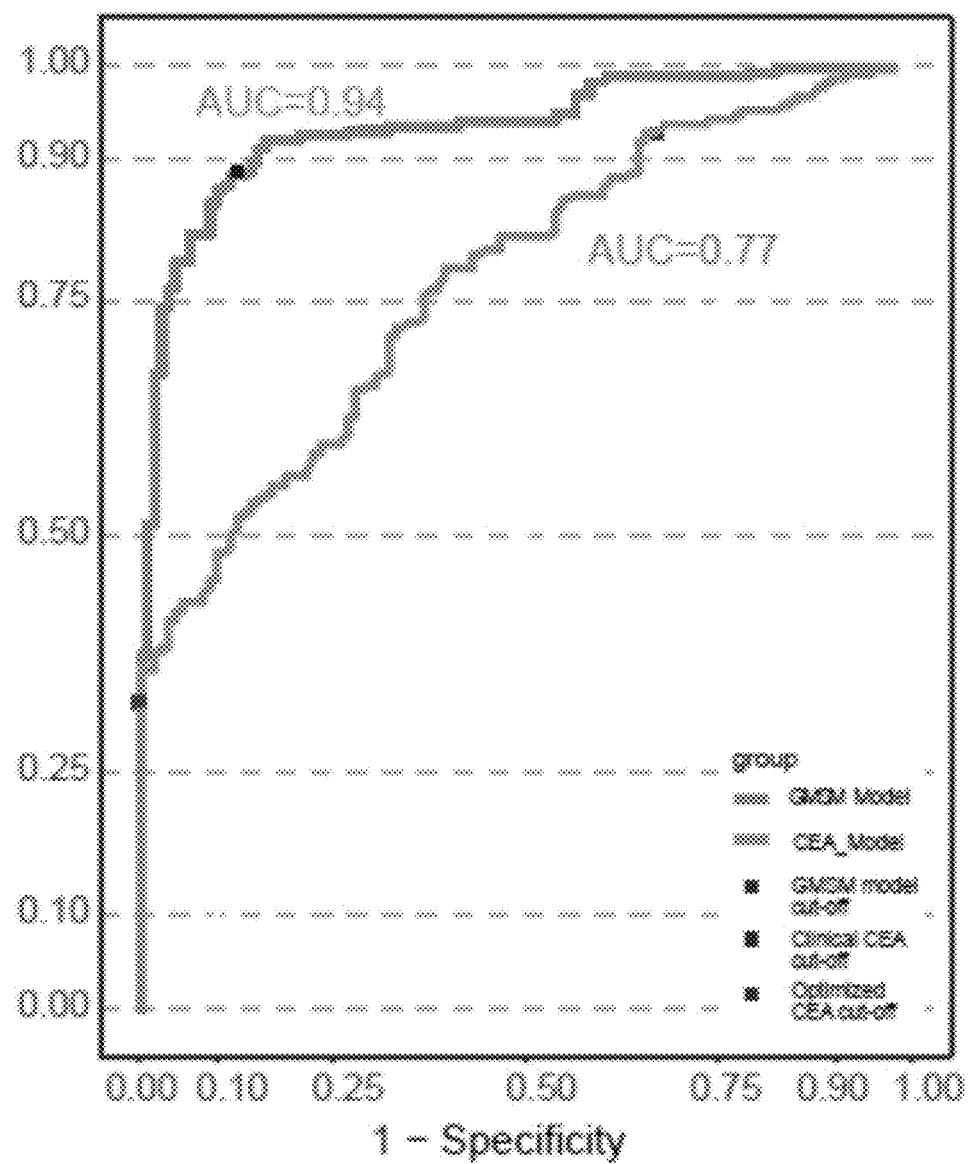
FIG. 5A illustrates a ROC curve showing discrimination efficiencies of CEA and the CRC Prediction model according to some embodiments of the present disclosure.
Figure 5B:
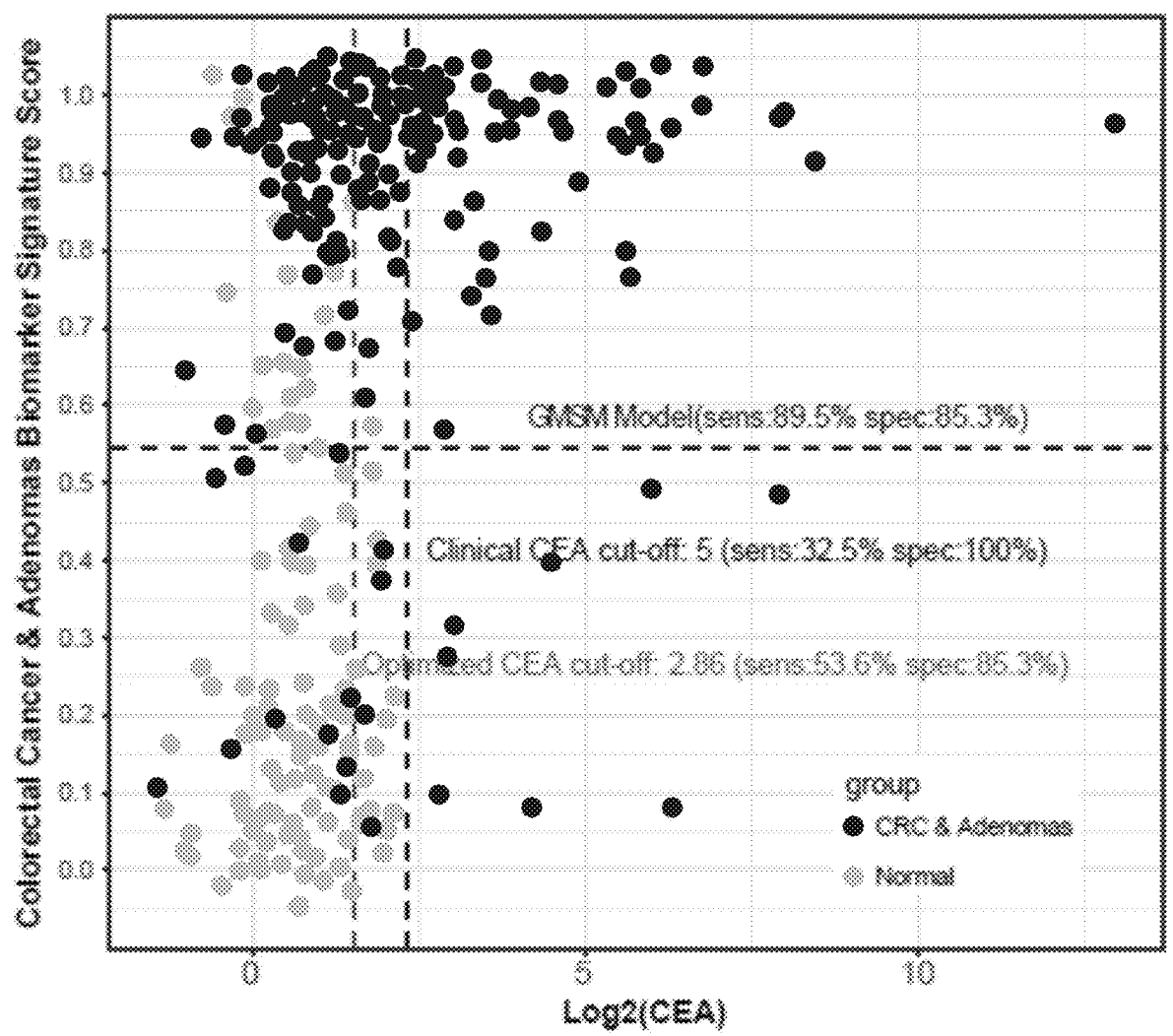
FIG. 5B illustrates a scatter plot for graphical comparison of the Prediction model and CEA efficiency in discriminating normal and colorectal abnormal patients according to some embodiments of the present disclosure.

Comparison of the Prediction Model with the Clinical Biomarker CEA in Discrimination of Colorectal Abnormality Serum CEA has been routinely used as a clinical biomarker for cancer detection, and a recent report also showed that combining the CEA with cell-free DNA (cfDNA) testing of mutants for a series of tumor-related genes could be applied to detect surgically dissectible cancer, including CRC. To compare the efficiencies of CEA and the predictive model of gut microbiome-associated serum metabolites for detection of CRC and adenomas patients, their performances in the CEA comparing cohort were assessed, consisting of all subjects with serum CEA score in both modeling and validation set. FIG. 5A illustrates a ROC curve showing discrimination efficiencies of CEA and the CRC Prediction model. Using CEA alone to diagnose colorectal abnormality leads to an AUC of 0.77, with a sensitivity of 32.5% and a specificity of 100% at the clinically used cut-off level of 5 U/ml, while setting the sensitivity at no less than 85% leads to a cut off of 2.86 U/ml, with a sensitivity of 53.6% and a specificity of 85.3%. These results indicate that the CEA marker showed an extremely low sensitivity, which was consistent with previous reports about the high false-negative rates of this biomarker in CRC discrimination. On the other hand, the Prediction model reached an AUC of 0.94 in this CEA comparing cohort, much higher than that of CEA, and a sensitivity of 89.5% and a specificity of 85.3% by directly transferring the cut-off value 0.541 to this group (see FIG. 5A). FIG. 5B illustrates a scatter plot for graphical comparison of the Prediction model (red dashed line) and CEA (clinical cut-off, blue dashed line; optimized cut-off, green dashed line) efficiency in discriminating normal (green spots) and colorectal abnormal patients (red spots). As shown in FIG. 5B, 187 among the 209 colorectal unhealthy patients could be detected by using the Prediction model, while this number decreased to only 68 by using CEA alone at the clinical cut off, leaving a large portion of CRC unhealthy patients undiagnosed. Thus, the Prediction model is superior to the clinical biomarker CEA in discrimination of colorectal abnormality.

Example 6

Figure 6A:
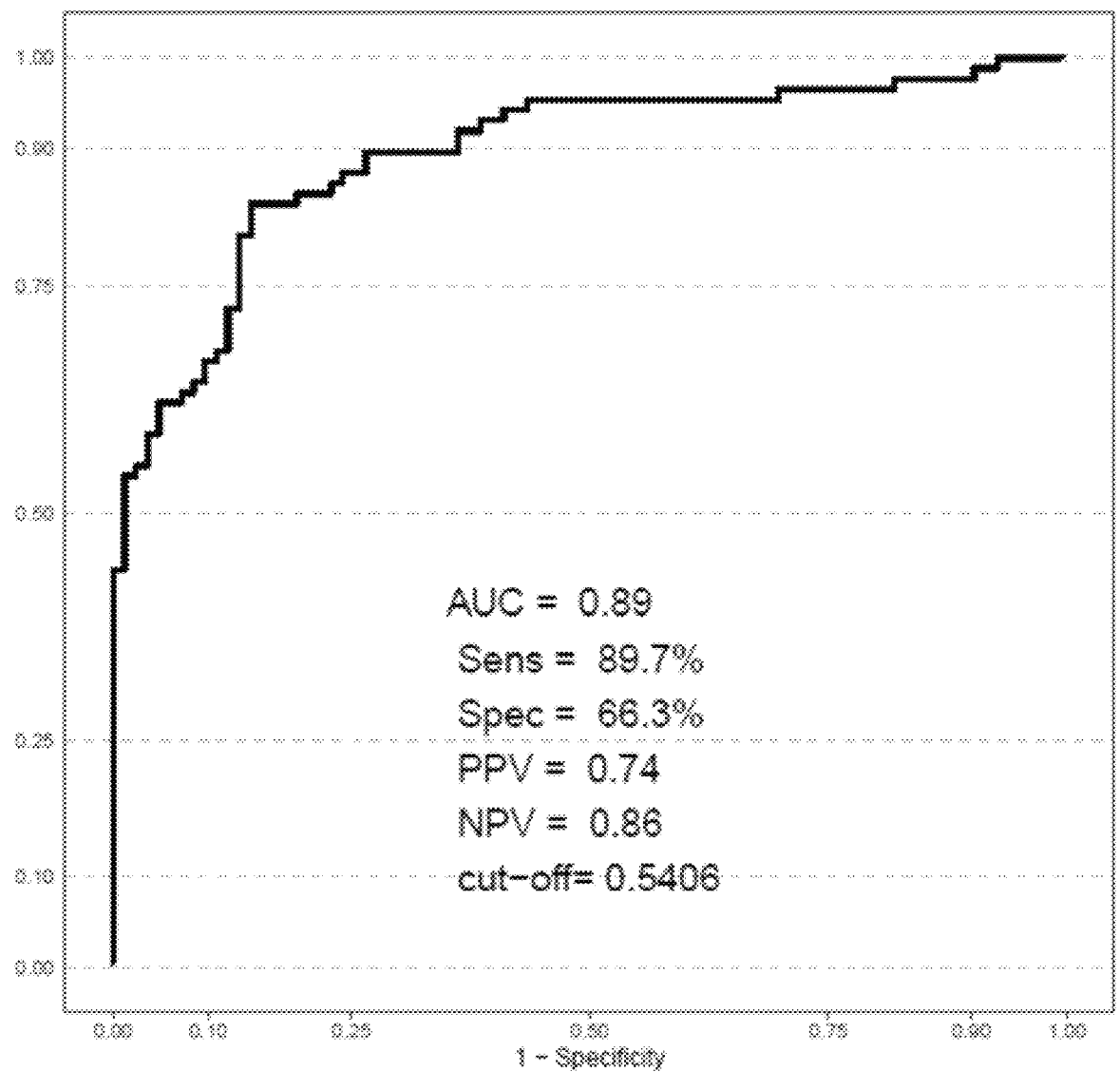
FIGS. 6A-6D are ROC curves illustrating the discrimination efficiencies of the CRC GMSM panel in a validation group.
Figure 6B:
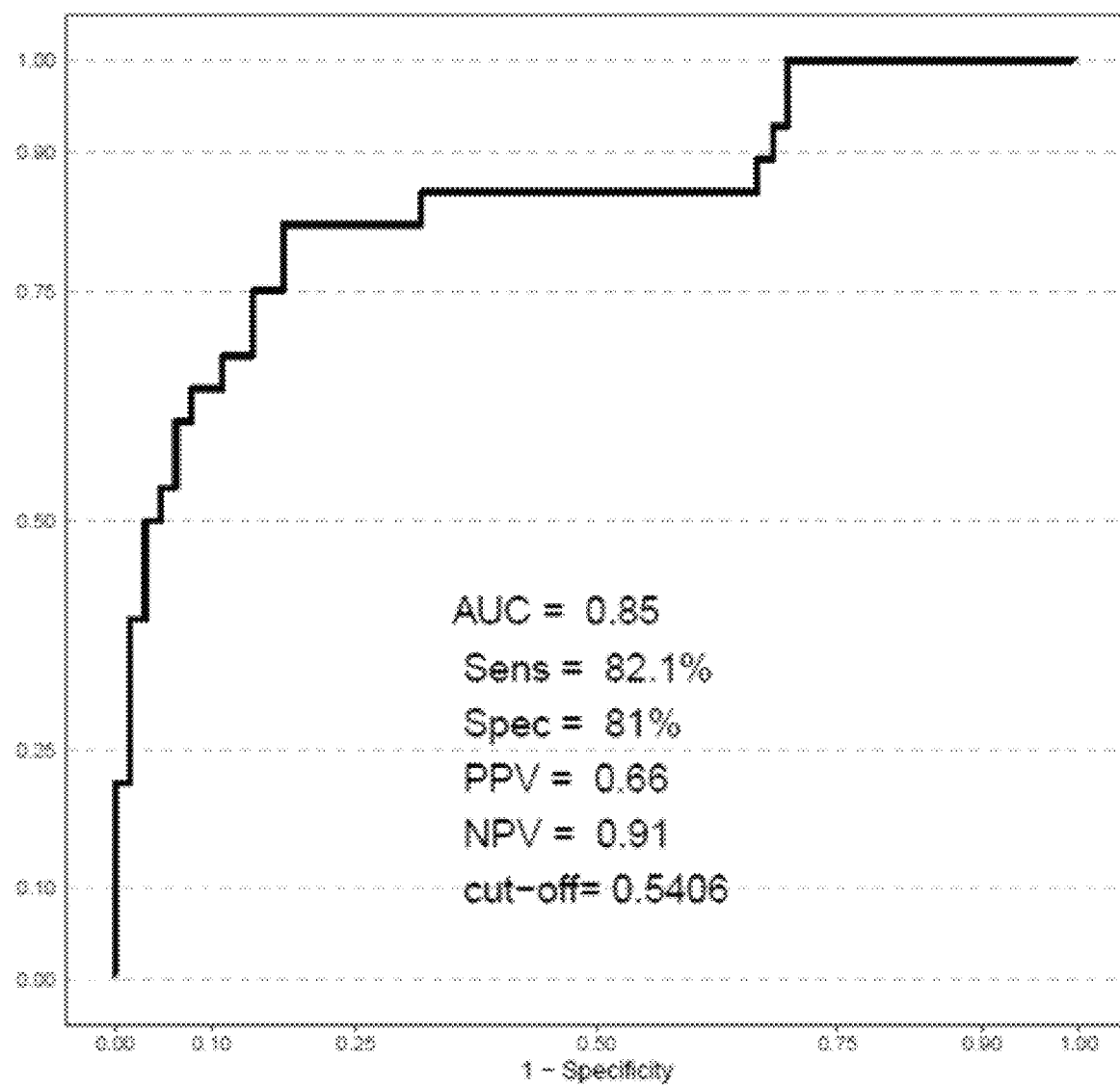
Figure 6C:
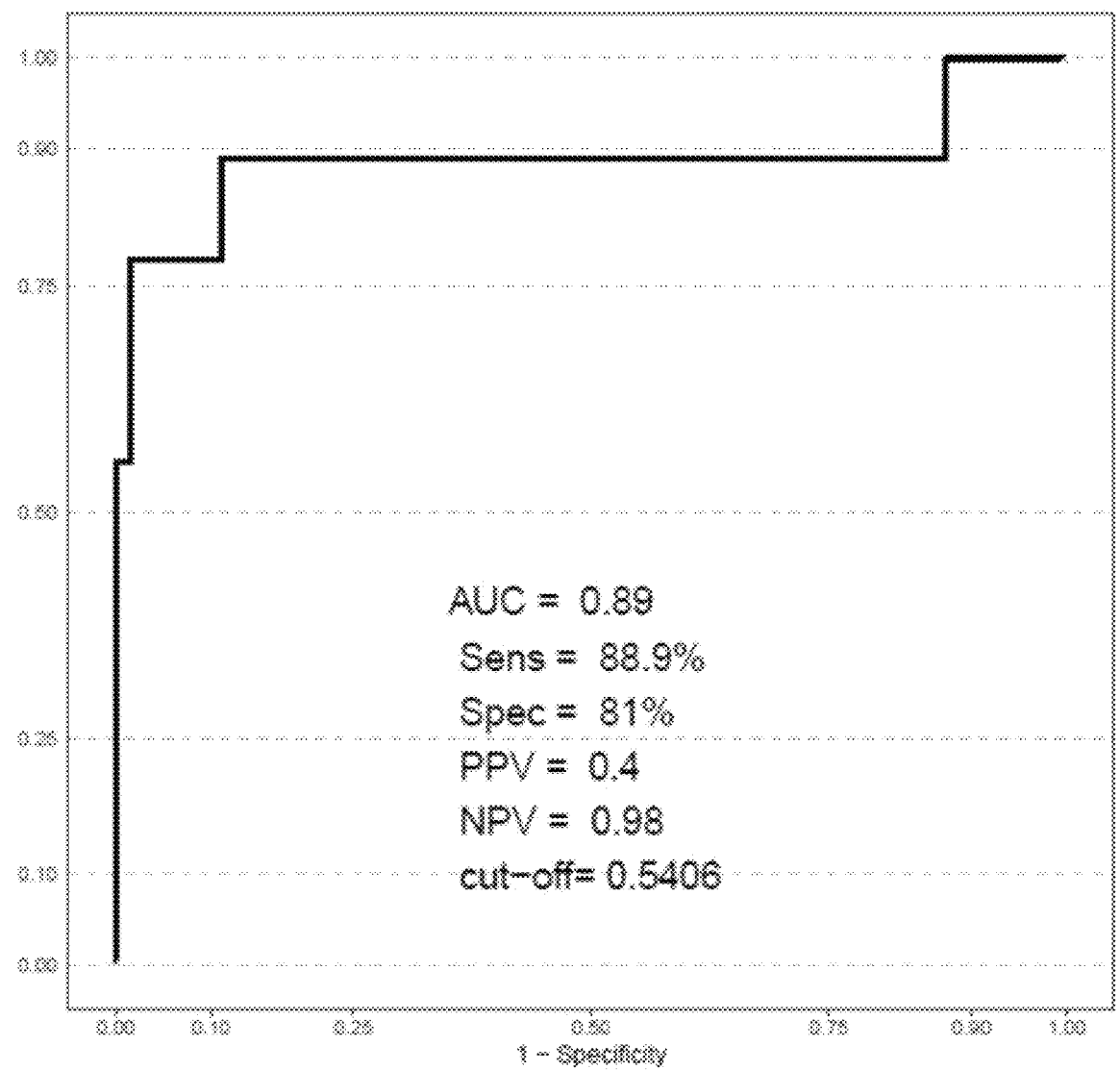
Figure 6D:
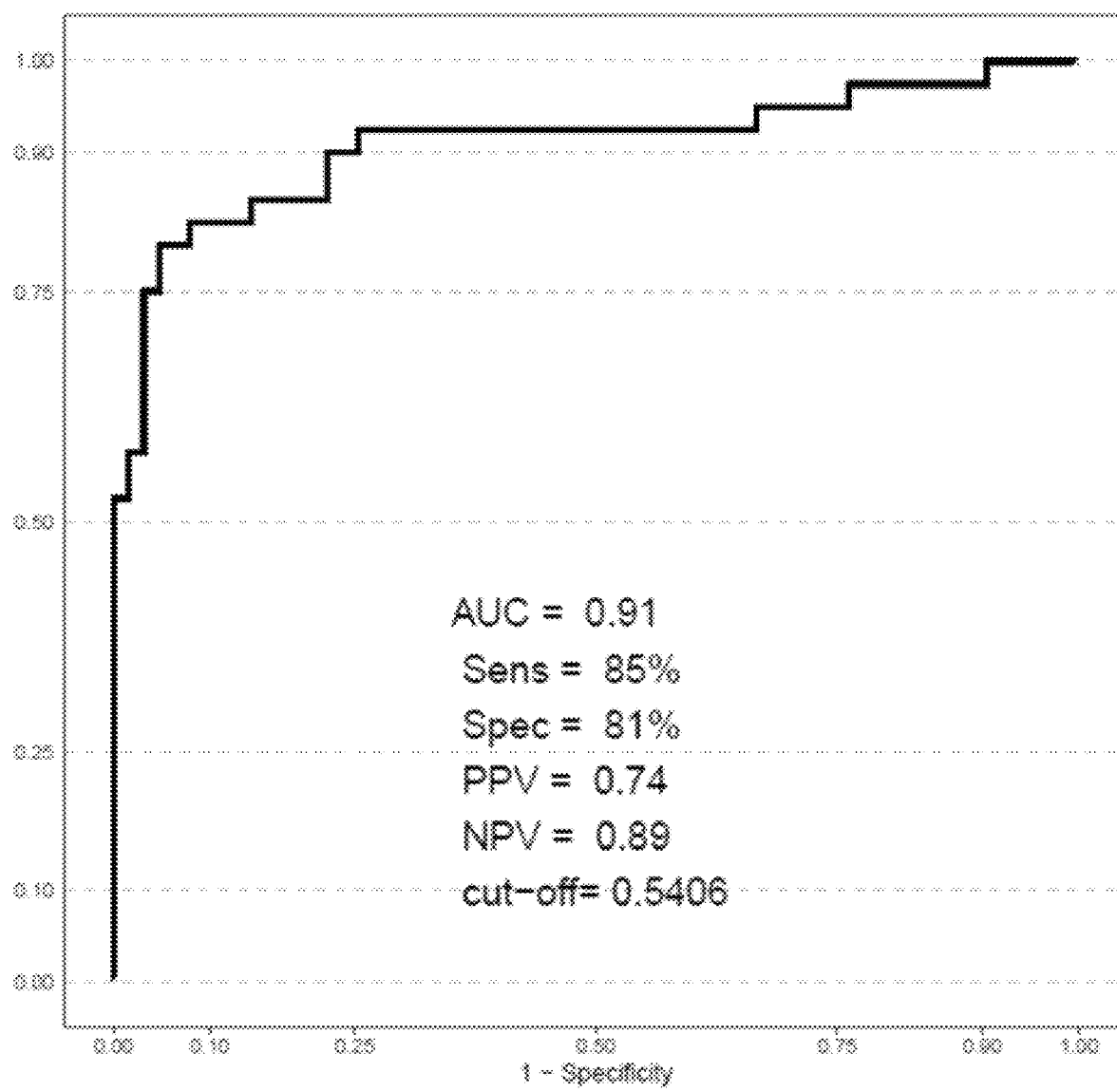

The Prediction Model can Distinguish Normal Subjects from Those with CRC in Different Stages FIGS. 6A-6D are ROC curves illustrating the discrimination efficiencies of the CRC GMSM panel in a validation group. Specific stage performances of this prediction model were examined separately according to the progression of colorectal abnormality from early stage to late-stage of colorectal unhealthy patients in the validation group. FIG. 6A showed that the prediction model distinguished normal subjects and patients with CRC, showing an AUC of 0. 89, and a sensitivity of 89.7%. FIG. 6B showed that the prediction model distinguished normal subjects with CRC patients in the early stage with an AUC of 0. 85, and a sensitivity of 82.1%, and a specificity of 81%. FIG. 6C showed that the prediction model distinguished normal subjects with CRC patients in the med-stage with an AUC of 0. 89, a sensitivity of 88.9%, and a specificity of 81%. FIG. 6D showed that the prediction model distinguished normal subjects with CRC patients in the late stage with an AUC of 0. 91, a sensitivity of 85%, and a specificity of 81%. These results indicate that the prediction model exhibited promising efficiency in distinguishing normal subjects and adenoma patients from those with CRC, and even distinguishing normal subjects from those with CRC in different stages, such as the early stage, the mid-stage, and the late stage.

This example indicates that the prediction model can be used to distinguish stage I/II/III/IV CRC in a subject.

Example 7

The Prediction Model can Distinguish Subjects with CRC/CRA from Normal Subjects Using the Abundance of at Least Two Metabolites Listed in Table 2

In some embodiments, the group of diagnostic biomarkers that can be quantified and used for detecting CRC/CRA and/or facilitating the treatment of CRC/CRA may include at least two metabolites listed in Table 2. Merely by way of example, exemplary groups of diagnostic biomarkers that can be quantified and used for these purposes are shown in Table 8. The corresponding performance of the prediction model utilizing these groups of diagnostic biomarkers is also evaluated. As shown in Table 8, the AUC, specificity, and sensitivity of the prediction model are relatively high, indicating that the prediction model utilizing the abundance of these metabolites may effectively distinguish subjects with CRC/CRA from normal subjects.

TABLE 8

| Metabolite1 | Metabolite2 | AUC | sensitivity | specificity |
|---|---|---|---|---|
| 9,12,13-TriHOME | 2-Octenoylcarnitine | 0.88 | 86.0% | 77.8% |
| 9,12,13-TriHOME | (E)-2-(4,8-dimethylnona-3,7-dien-1-yl)-5-hydroxy-2,7-dimethyl-2H-chromene-8-carbaldehyde | 0.84 | 80.4% | 79.4% |
| Culinariside | 2-Octenoylcarnitine | 0.89 | 85.0% | 81.0% |
| Culinariside | N,O-Bis-(trimethylsilyl)phenylalanine | 0.80 | 76.6% | 76.2% |
| [(6-{[5,7-dihydroxy-2-(4-oxocyclohexa-2,5-dien-1-ylidene)-2H-chromen-3-yl]oxy}-3,4,5-trihydroxyoxan-2-yl)methyl][1-hydroxy-3-(4-hydroxyphenyl)prop-2-en-1-ylidene]oxidanium | 2-Octenoylcarnitine | 0.93 | 90.7% | 82.5% |
| 2-Octenoylcarnitine | N,O-Bis-(trimethylsilyl)phenylalanine | 0.88 | 88.8% | 79.4% |
| 2-Octenoylcarnitine | 14-HDoHE | 0.88 | 86.9% | 81.0% |
| (E)-2-(4,8-dimethylnona-3,7-dien-1-yl)-5-hydroxy-2,7-dimethyl-2H-chromene-8-carbaldehyde | N,O-Bis-(trimethylsilyl)phenylalanine | 0.83 | 82.2% | 76.2% |

Example 8

The Prediction Model can Distinguish Subjects with CRC/CRA from Normal Subjects Using the Abundance of at Least Three Metabolites Listed in Table 2

In some embodiments, the group of diagnostic biomarkers that can be quantified and used for detecting CRC/CRA and/or facilitating the treatment of CRC/CRA may include at least three metabolites listed in Table 2. Merely by way of example, exemplary groups of diagnostic biomarkers that can be quantified and used for these purposes are shown in Table 9. The corresponding performance of the prediction model utilizing these groups of diagnostic biomarkers is also evaluated. As shown in Table 9, the AUC, specificity, and sensitivity of the prediction model are relatively high, indicating that the prediction model utilizing the abundance of these metabolites may effectively distinguish subjects with CRC/CRA from normal subjects.

TABLE 9

| Metabolite1 | Metabolite2 | Metabolite3 | AUC | sensitivity | specificity |
|---|---|---|---|---|---|
| 9,12,13-TriHOME | 9,12,18-TriHOME | N,O-Bis-(trimethylsilyl)phenylalanine | 0.82 | 78.5% | 76.2% |
| 9,12,13-TriHOME | Culinariside | 2-Octenoylcarnitine | 0.89 | 87.9% | 77.8% |
| 9,12,13-TriHOME | [(6-{[5,7-dihydroxy-2-(4-oxocyclohexa-2,5-dien-1-ylidene)-2H-chromen-3-yl]oxy}-3,4,5-trihydroxyoxan-2-yl)methyl][1-hydroxy-3-(4-hydroxyphenyl)prop-2-en-1-ylidene]oxidanium | 2-Octenoylcarnitine | 0.93 | 89.7% | 82.5% |
| 9,12,13-TriHOME | (E)-2-(4,8-dimethylnona-3,7-dien-1-yl)-5-hydroxy-2,7-dimethyl-2H-chromene-8-carbaldehyde | N,O-Bis-(trimethylsilyl)phenylalanine | 0.84 | 85.0% | 76.2% |
| 9,12,13-TriHOME | (E)-2-(4,8-dimethylnona-3,7-dien-1-yl)-5-hydroxy-2,7-dimethyl-2H-chromene-8-carbaldehyde | 14-HDoHE | 0.84 | 81.3% | 79.4% |
| 9,12,18-TriHOME | Culinariside | 2-Octenoylcarnitine | 0.89 | 85.0% | 79.4% |
| 9,12,18-TriHOME | Culinariside | (E)-2-(4,8-dimethylnona-3,7-dien-1-yl)-5-hydroxy-2,7-dimethyl-2H-chromene-8-carbaldehyde | 0.85 | 80.4% | 79.4% |
| 9,12,18-TriHOME | [(6-{[5,7-dihydroxy-2-(4-oxocyclohexa-2,5-dien-1-ylidene)-2H-chromen-3-yl]oxy}-3,4,5-trihydroxyoxan-2-yl)methyl][1-hydroxy-3-(4-hydroxyphenyl)prop-2-en-1-ylidene]oxidanium | 2-Octenoylcarnitine | 0.93 | 90.7% | 84.1% |
| 9,12,18-TriHOME | [(6-{[5,7-dihydroxy-2-(4-oxocyclohexa-2,5-dien-1-ylidene)-2H-chromen-3-yl]oxy}-3,4,5-trihydroxyoxan-2-yl)methyl][1-hydroxy-3-(4-hydroxyphenyl)prop-2-en-1-ylidene]oxidanium | (E)-2-(4,8-dimethylnona-3,7-dien-1-yl)-5-hydroxy-2,7-dimethyl-2H-chromene-8-carbaldehyde | 0.92 | 92.5% | 76.2% |

TABLE 9-continued

| Metabolite1 | Metabolite2 | Metabolite3 | AUC | sensitivity | specificity |
|---|---|---|---|---|---|
| 9,12,18-TriHOME | 2-Octenoylcarnitine | (E)-2-(4,8-dimethylnona-3,7-dien-1-yl)-5-hydroxy-2,7-dimethyl-2H-chromene-8-carbaldehyde | 0.89 | 86.9% | 77.8% |
| 9,12,18-TriHOME | 2-Octenoylcarnitine | 14-HDoHE | 0.88 | 86.0% | 77.8% |
| 9,12,18-TriHOME | (E)-2-(4,8-dimethylnona-3,7-dien-1-yl)-5-hydroxy-2,7-dimethyl-2H-chromene-8-carbaldehyde | N,O-Bis-(trimethylsilyl)phenylalanine | 0.84 | 80.4% | 76.2% |
| 9,12,18-TriHOME | N,O-Bis-(trimethylsilyl)phenylalanine | 14-HDoHE | 0.81 | 76.6% | 79.4% |
| Culinariside | [(6-{[5,7-dihydroxy-2-(4-oxocyclohexa-2,5-dien-1-ylidene)-2H-chromen-3-yl]oxy}-3,4,5-trihydroxyoxan-2-yl)methyl][1-hydroxy-3-(4-hydroxyphenyl)prop-2-en-1-ylidene]oxidanium | 2-Octenoylcarnitine | 0.93 | 90.7% | 82.5% |
| Culinariside | [(6-{[5,7-dihydroxy-2-(4-oxocyclohexa-2,5-dien-1-ylidene)-2H-chromen-3-yl]oxy}-3,4,5-trihydroxyoxan-2-yl)methyl][1-hydroxy-3-(4-hydroxyphenyl)prop-2-en-1-ylidene]oxidanium | 14-HDoHE | 0.89 | 84.1% | 79.4% |
| Culinariside | 2-Octenoylcarnitine | N,O-Bis-(trimethylsilyl)phenylalanine | 0.89 | 87.9% | 79.4% |
| Culinariside | 2-Octenoylcarnitine | 14-HDoHE | 0.89 | 88.8% | 79.4% |
| [(6-{[5,7-dihydroxy-2-(4-oxocyclohexa-2,5-dien-1-ylidene)-2H-chromen-3-yl]oxy}-3,4,5-trihydroxyoxan-2-yl)methyl][1-hydroxy-3-(4-hydroxyphenyl)prop-2-en-1-ylidene]oxidanium | 2-Octenoylcarnitine | (E)-2-(4,8-dimethylnona-3,7-dien-1-yl)-5-hydroxy-2,7-dimethyl-2H-chromene-8-carbaldehyde | 0.94 | 92.5% | 82.5% |
| [(6-{[5,7-dihydroxy-2-(4-oxocyclohexa-2,5-dien-1-ylidene)-2H-chromen-3-yl]oxy}-3,4,5-trihydroxyoxan-2-yl)methyl][1-hydroxy-3-(4-hydroxyphenyl)prop-2-en-1-ylidene]oxidanium | 2-Octenoylcarnitine | N,O-Bis-(trimethylsilyl)phenylalanine | 0.93 | 90.7% | 82.5% |

TABLE 9-continued

| Metabolite1 | Metabolite2 | Metabolite3 | AUC | sensitivity | specificity |
|---|---|---|---|---|---|
| [(6-{[5,7-dihydroxy-2-(4-oxocyclohexa-2,5-dien-1-ylidene)-2H-chromen-3-yl]oxy}-3,4,5-trihydroxyoxan-2-yl)methyl][1-hydroxy-3-(4-hydroxyphenyl)prop-2-en-1-ylidene]oxidanium | 2-Octenoylcarnitine | 14-HDoHE | 0.93 | 89.7% | 82.5% |
| [(6-{[5,7-dihydroxy-2-(4-oxocyclohexa-2,5-dien-1-ylidene)-2H-chromen-3-yl]oxy}-3,4,5-trihydroxyoxan-2-yl)methyl][1-hydroxy-3-(4-hydroxyphenyl)prop-2-en-1-ylidene]oxidanium | (E)-2-(4,8-dimethylnona-3,7-dien-1-yl)-5-hydroxy-2,7-dimethyl-2H-chromene-8-carbaldehyde | N,O-Bis-(trimethylsilyl)phenylalanine | 0.92 | 91.6% | 76.2% |
| [(6-{[5,7-dihydroxy-2-(4-oxocyclohexa-2,5-dien-1-ylidene)-2H-chromen-3-yl]oxy}-3,4,5-trihydroxyoxan-2-yl)methyl][1-hydroxy-3-(4-hydroxyphenyl)prop-2-en-1-ylidene]oxidanium | (E)-2-(4,8-dimethylnona-3,7-dien-1-yl)-5-hydroxy-2,7-dimethyl-2H-chromene-8-carbaldehyde | 14-HDoHE | 0.92 | 90.7% | 76.2% |
| 2-Octenoylcarnitine | (E)-2-(4,8-dimethylnona-3,7-dien-1-yl)-5-hydroxy-2,7-dimethyl-2H-chromene-8-carbaldehyde | 14-HDoHE | 0.89 | 86.0% | 77.8% |
| 2-Octenoylcarnitine | N,O-Bis-(trimethylsilyl)phenylalanine | 14-HDoHE | 0.88 | 86.9% | 81.0% |

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure and are within the spirit and scope of the exemplary embodiments of this disclosure.

Moreover, certain terminology has been used to describe embodiments of the present disclosure. For example, the terms "one embodiment," "an embodiment," and "some embodiments" mean that a particular feature, structure, or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures, or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "module," "unit," "component," "device," or "system." Furthermore, aspects of the present disclosure may take the form of a computer program product embodied in one or more computer-readable medium having computer readable program code embodied thereon.

Furthermore, the recited order of processing elements or sequences, or the use of numbers, letters, or other designations, therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software-only solution, e.g., an installation on an existing server or mobile device.

Similarly, it should be appreciated that in the foregoing description of embodiments of the present disclosure, various features are sometimes grouped together in a single embodiment, figure, or description thereof to streamline the disclosure aiding in the understanding of one or more of the various embodiments. This method of disclosure, however, is not to be interpreted as reflecting an intention that the claimed subject matter requires more features than are expressly recited in each claim. Rather, claim subject matter lie in less than all features of a single foregoing disclosed embodiment.

What is claimed is:

1. A method of detecting CRC/CRA in a subject and treating the subject, the method comprising:
   (a) quantifying the abundance of one or more metabolites in a panel of a plurality of metabolites in a sample from the subject, wherein the plurality of metabolites include the metabolites of Table A:

TABLE A

| MASS(+/−) | Compound | Delta(ppm) |
|---|---|---|
| 329.233(−) | C18H34O5 | 1 |
| 329.233(−) | 9,12,18-TriHOME (12Z) | 1 |
| 420.807(+) | C42H80NO8P | 19 |
| 637.157(−) | C32H31O14 | 0 |
| 398.18(−) | C15H27NO4 | 1 |
| 353.212(−) | C23H29O3 | 0 |
| 368.169(−) | C19H23N5O3 | 10 |
| 355.228(−) | C46H64O6 | 0 |

(b) determining a sample score by processing the abundance of each of the metabolites quantified in step (a);
   (c) detecting CRC/CRA by comparing the sample score to a cut-off score; and
   (d) applying treatment to the subject for CRC/CRA, wherein the treatment includes colectomy or ostomy.

2. The method of claim 1, wherein the sample is a blood serum sample.

3. The method of claim 1, wherein the subject is a human.

4. The method of claim 1, further comprising verifying the CRC/CRA with colonoscopy.

5. The method of claim 1, wherein the treatment further includes chemotherapy, radiation therapy, targeted drug therapy, or immunotherapy.

6. The method of claim 1, wherein the treatment further includes palliative care.

7. The method of claim 1, wherein the abundance of at least two, three, or four metabolites in Table A are quantified.

8. The method of claim 1, wherein the abundance of all eight metabolites in Table A are quantified.

9. The method of claim 1, wherein the plurality of metabolites further include the metabolites of Table B:

TABLE B

| MASS(+/−) | Compound | Delta(ppm) |
|---|---|---|
| 193.09(−) | C6H14OS | 2 |
| 380.033(−) | C15H15N3O5S2 | 13 |
| 289.164(+) | C15H22O5 | 4 |
| 750.519(+) | C39H76NO10P | 12 |
| 357.228(−) | C15H30N6O4 | 7 |
| 637.105(+) | C23H22F7N4O6P | 1 |
| 612.425(+) | C37H54O6 | 1 |
| 512.336(−) | C27H45NO | 1 |
| 543.376(+) | C35H52O3 | 9 |
| 490.686(+) | C80H152O17P2 | 3 |
| 483.297(−) | C26H44O8 | 1 |
| 319.264(−) | C21H36O2 | 1 |
| 447.312(−) | C27H44O5 | 1 |
| 279.233(−) | C18H32O2 | 0 |
| 578.25(+) | C28H37N5O7 | 15 |
| 572.415(+) | C29H60NO7P | 21 |
| 461.196(+) | C26H30O6 | 6 |
| 475.116(−) | C19H24O14 | 14 |
| 513.363(+) | C32H48O5 | 11 |
| 502.015(+) | C16H22BrN3O7S | 21 |
| 384.259(+) | C22H35NO3 | 21 |
| 197.068(−) | C7H10N4O3 | 0 |
| 584.729(+) | C43H74N7O17P3S | 15 | and wherein the abundance of all eight metabolites in Table A and the abundance of at least one metabolite in Table B are quantified.

10. The method of claim 1, wherein the plurality of metabolites further include the metabolites in Table C:

TABLE C

| MASS(+/−) | Compound | Delta(ppm) |
|---|---|---|
| 193.09(−) | C11H14O3 | 15 |
| 223.134(−) | C13H20O3 | 0 |
| 289.106(−) | C16H18O5 | 7 |
| 355.227(+) | C21H32O3 | 7 |
| 382.183(+) | C20H25NO6 | 3 |
| 386.067(−) | C14H15NO9 | 15 |
| 398.179(−) | C22H29N3S2 | 15 |
| 447.311(−) | C27H44O5 | 1 |
| 461.195(+) | C28H28O6 | 2 |
| 462.141(−) | C19H20FN5O5 | 4 |
| 471.005(+) | C16H16O11S2 | 5 |
| 476.011(+) | C10H16N5O11P3 | 5 |
| 476.358(+) | C30H42O2 | 12 |
| 477.13(+) | C28H22O6 | 2 |
| 483.368(+) | C30H52O2 | 17 |
| 494.68(+) | C83H150O17P2 | 11 |
| 495.024(+) | C21H12O14 | 30 |
| 504.692(+) | C12H6Br4O | 25 |
| 509.03(+) | C10H16N5O12P3 | 9 |
| 514.027(+) | C10H17N7O12S2 | 0 |
| 514.705(+) | C44H61N13O12S2 | 5 |
| 519.043(+) | C20H16O15 | 9 |
| 531.178(−) | C27H32O11 | 17 |
| 534.052(+) | C16H17N9O5S3 | 21 |
| 536.299(−) | C23H44NO7P | 1 |
| 539.384(+) | C32H52O5 | 25 |
| 542.426(+) | C54H106NO10P | 2 |
| 543.378(+) | C35H52O3 | 5 |
| 549.062(+) | C22H22O14 | 4 |
| 563.068(+) | C30H20O9 | 10 |
| 567.155(−) | C28H28N2O11 | 12 |
| 568.075(+) | C21H18O14S | 1 |
| 587.088(+) | C25H24O13S | 9 |
| 597.091(+) | C26H22O15 | 10 |
| 616.463(+) | C37H58O6 | 9 |
| 629.391(−) | C40H56O7 | 11 |
| 631.103(−) | C28H24O17 | 14 |
| 646.473(+) | C35H68NO7P | 12 |
| 702.536(+) | C39H76NO7P | 10 |
| 732.546(+) | C41H76NO7P | 8 |
| 776.038(+) | C27H20O21S | 1 |
| 804.604(+) | C45H84NO8P | 7 |
| 877.609(+) | C44H85NO11S | 10 |
| 938.662(+) | C54H94NO8P | 1 |
| 950.698(+) | C54H97NO10P | 14 |
| 994.724(+) | C54H101NO13 | 8 |
| 1038.751(+) | C65H98O6 | 1 |

TABLE C-continued

| MASS(+/−) | Compound | Delta(ppm) |
|---|---|---|
| 1040.729(+) | C56H107NO13 | 8 |
| 432.109(−) | C21H21O10 | 6 |
| 635.934(+) | C64H120N2O21 | 9 |
| 714.829(+) | C65H102O33 | 9 | and wherein the abundance of all eight metabolites in Table A and the abundance of all the metabolites in Table C are quantified.

11. The method of claim 1, wherein the sample score indicates a probability that the subject has CRC/CRA.

12. The method of claim 1, wherein step (b) includes:
normalizing the abundance of each of the metabolites quantified in step (a); and
determining the sample score by processing the normalized abundance with a prediction model.

13. The method of claim 12, wherein the prediction model is established by a logistic regression method.

14. The method of claim 12, wherein the prediction model is established by a logistic regression method based on measurement of the abundance of the metabolites from samples with known normal, CRC, or CRA status.

15. The method of claim 12, wherein the prediction model is established by the logistic regression method using a plurality of training datasets, wherein each of the plurality of training datasets may include a concentration of a sample metabolite of a sample subject and a label indicating whether the sample subject has CRC or CRA, or is normal.

16. The method of claim 1, wherein step (c) includes detecting CRC/CRA in the subject if the sample score is equal to or greater than the cut-off score.

17. The method of claim 1, wherein for a receiver operating characteristic (ROC) curve, the method has an area-under-the-curve (AUC) of more than 0.80, and both sensitivity and specificity of detecting CRC/CRA in the sample are equal to or greater than 75%.

18. The method of claim 1, wherein the CRC in the subject is early-stage CRC.

19. The method of claim 1, wherein the CRC in the subject is middle-stage CRC.

20. The method of claim 1, wherein the CRC in the subject is late-stage CRC.

* * * * *